United States Patent
Kim

(10) Patent No.: US 7,857,857 B2
(45) Date of Patent: Dec. 28, 2010

(54) DEVICES, SYSTEMS AND METHODS FOR AUGMENTING INTERVERTEBRAL DISCS

(75) Inventor: Daniel H. Kim, Houston, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/271,525

(22) Filed: Nov. 10, 2005

(65) Prior Publication Data

US 2006/0247784 A1    Nov. 2, 2006

Related U.S. Application Data

(63) Continuation-in-part of application No. 11/120,639, filed on May 2, 2005.

(51) Int. Cl.
*A61F 2/44* (2006.01)
(52) U.S. Cl. .................... 623/17.16; 623/17.11
(58) Field of Classification Search ............ 623/16.11, 623/17.11–17.16; 606/280, 281, 70, 71, 606/282–299
See application file for complete search history.

(56) References Cited

U.S. PATENT DOCUMENTS

| | | | |
|---|---|---|---|
| 4,164,559 A | 8/1979 | Miyata et al. | |
| 5,328,955 A | 7/1994 | Rhee et al. | |
| 5,433,739 A | 7/1995 | Sluijter et al. | |
| 5,456,720 A | 10/1995 | Schultz | |
| 5,545,178 A | 8/1996 | Kensey | |
| 5,702,454 A | 12/1997 | Baumgartner | |
| 5,800,549 A | 9/1998 | Bao | |
| 6,132,465 A | 10/2000 | Ray | |
| 6,200,347 B1 * | 3/2001 | Anderson et al. | 623/16.11 |
| 6,224,630 B1 | 5/2001 | Bao et al. | |
| 6,245,107 B1 | 6/2001 | Ferree | |
| 6,261,311 B1 | 7/2001 | Sharkey et al. | |
| 6,264,695 B1 | 7/2001 | Stoy | |
| 6,371,990 B1 | 4/2002 | Ferree | |
| 6,402,750 B1 | 6/2002 | Atkinson | |
| 6,408,839 B1 | 6/2002 | Hauser | |
| 6,425,919 B1 * | 7/2002 | Lambrecht | 623/17.16 |

(Continued)

FOREIGN PATENT DOCUMENTS

WO    WO 03/043535    5/2003

OTHER PUBLICATIONS

U.S. Appl. No. 11/359,754, filed Feb. 21, 2006, entitled "Fabrication and Use of Biocompatible Materials for Treating and Repairing Herniated Spinal Discs," Inventor: Daniel H. Kim et al., Non-Final Office Action executed Sep. 4, 2007 and mailed Sep. 6, 2007.

(Continued)

*Primary Examiner*—Eduardo C Robert
*Assistant Examiner*—Tara R Carter

(57) ABSTRACT

Devices, systems and methods are provided for augmenting intervertebral discs. The systems include implantable annulus repair and augmentation devices as well as implantable prosthetic materials for replacing a portion of or augmenting the annulus and/or the nucleus pulposus. The systems further include instruments for implanting the subject devices and materials in a minimally invasive manner. The methods are directed to the minimally invasive implantation of one or more of the subject annulus repair devices and the prosthetic materials to within the intervertebral disc.

36 Claims, 94 Drawing Sheets

U.S. PATENT DOCUMENTS

| | | |
|---|---|---|
| 6,425,923 B1 | 7/2002 | Stalcup |
| 6,428,576 B1 | 8/2002 | Haldiman |
| 6,443,988 B2 | 9/2002 | Felt et al. |
| 6,482,235 B1 * | 11/2002 | Lambrecht et al. ....... 623/17.16 |
| 6,508,839 B1 | 1/2003 | Lambrecht et al. |
| 6,517,568 B1 | 2/2003 | Sharkey et al. |
| 6,530,933 B1 | 3/2003 | Yeung |
| 6,562,028 B2 | 5/2003 | Nield |
| 6,579,291 B1 | 6/2003 | Keith |
| 6,592,625 B2 * | 7/2003 | Cauthen ................... 623/17.16 |
| 6,602,291 B1 | 8/2003 | Ray |
| 6,682,535 B2 | 1/2004 | Hoogland |
| 6,689,125 B1 | 2/2004 | Keith et al. |
| 6,712,853 B2 * | 3/2004 | Kuslich ................... 623/17.16 |
| 6,712,859 B2 | 3/2004 | Rousseau |
| 6,736,815 B2 | 5/2004 | Ginn |
| 6,755,867 B2 | 6/2004 | Rousseau |
| 6,783,554 B2 * | 8/2004 | Amara et al. ............ 623/23.76 |
| 6,805,695 B2 | 10/2004 | Keith |
| 6,805,715 B2 | 10/2004 | Reuter |
| 6,821,276 B2 | 11/2004 | Lambrecht et al. |
| 6,830,570 B1 | 12/2004 | Frey |
| 6,833,520 B1 | 12/2004 | Wong et al. |
| 6,835,205 B2 | 12/2004 | Atkinson et al. |
| 6,883,520 B2 | 4/2005 | Lambrecht |
| 6,932,843 B2 | 8/2005 | Smith et al. |
| 6,936,072 B2 | 8/2005 | Lambrecht |
| 6,960,215 B2 | 11/2005 | Olson, Jr. et al. |
| 6,962,979 B1 | 11/2005 | Rhee |
| 6,969,404 B2 | 11/2005 | Ferree |
| 6,984,247 B2 | 1/2006 | Cauthen |
| 6,997,956 B2 | 2/2006 | Cauthen |
| 7,004,970 B2 | 2/2006 | Cauthen, III et al. |
| 7,033,393 B2 | 4/2006 | Gainor et al. |
| 7,033,395 B2 | 4/2006 | Cauthen |
| 7,052,516 B2 | 5/2006 | Cauthen, III et al. |
| 7,056,345 B2 | 6/2006 | Kuslich |
| 7,094,258 B2 | 8/2006 | Lambrecht et al. |
| 7,128,746 B2 | 10/2006 | Singer et al. |
| 7,189,235 B2 | 3/2007 | Cauthen |
| 7,198,047 B2 | 4/2007 | Lambrecht et al. |
| 7,220,281 B2 | 5/2007 | Lambrecht et al. |
| 7,223,289 B2 | 5/2007 | Trieu et al. |
| 7,258,700 B2 | 8/2007 | Lambrecht et al. |
| 7,273,497 B2 | 9/2007 | Ferree |
| 7,326,200 B2 | 2/2008 | Trieu et al. |
| 7,445,634 B2 | 11/2008 | Trieu |
| 7,563,282 B2 * | 7/2009 | Lambrecht et al. ....... 623/17.11 |
| 7,789,912 B2 | 9/2010 | Manzi et al. |
| 2002/0026244 A1 | 2/2002 | Trieu |
| 2002/0111688 A1 | 8/2002 | Cauthen |
| 2002/0120337 A1 | 8/2002 | Cauthen |
| 2002/0123750 A1 | 9/2002 | Eisermann et al. |
| 2002/0123807 A1 | 9/2002 | Cauthen |
| 2002/0151979 A1 | 10/2002 | Lambrecht et al. |
| 2002/0151980 A1 | 10/2002 | Cauthen |
| 2002/0189622 A1 | 12/2002 | Cauthen |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0040796 A1 | 2/2003 | Ferree |
| 2003/0074075 A1 | 4/2003 | Thomas, Jr. et al. |
| 2003/0078579 A1 | 4/2003 | Ferree |
| 2003/0153976 A1 | 8/2003 | Cauthen |
| 2003/0158604 A1 | 8/2003 | Cauthen, III et al. |
| 2003/0163200 A1 | 8/2003 | Cauthen |
| 2003/0181983 A1 | 9/2003 | Cauthen |
| 2003/0187507 A1 | 10/2003 | Cauthen |
| 2003/0187508 A1 | 10/2003 | Cauthen |
| 2003/0195514 A1 * | 10/2003 | Trieu et al. .................... 606/61 |
| 2003/0220690 A1 | 11/2003 | Cauthen |
| 2003/0220693 A1 | 11/2003 | Cauthen |
| 2003/0220694 A1 | 11/2003 | Cauthen |
| 2004/0002763 A1 | 1/2004 | Phillips |
| 2004/0002764 A1 | 1/2004 | Gainor |
| 2004/0024463 A1 | 2/2004 | Thomas, Jr. et al. |
| 2004/0024465 A1 | 2/2004 | Lambrecht et al. |
| 2004/0028655 A1 | 2/2004 | Nelson et al. |
| 2004/0034429 A1 | 2/2004 | Lambrecht |
| 2004/0039392 A1 | 2/2004 | Trieu |
| 2004/0111161 A1 | 6/2004 | Trieu |
| 2004/0186573 A1 | 9/2004 | Ferree |
| 2004/0267368 A1 | 12/2004 | Kuslich |
| 2005/0021029 A1 | 1/2005 | Trieu |
| 2005/0043733 A1 | 2/2005 | Eisermann et al. |
| 2005/0049592 A1 | 3/2005 | Keith |
| 2005/0049604 A1 | 3/2005 | Singer |
| 2005/0149197 A1 | 7/2005 | Cauthen |
| 2005/0159817 A1 | 7/2005 | Ferree |
| 2005/0187555 A1 * | 8/2005 | Biedermann et al. .......... 606/72 |
| 2005/0256582 A1 | 11/2005 | Ferree |
| 2005/0278027 A1 | 12/2005 | Hyde, Jr. |
| 2005/0283246 A1 | 12/2005 | Cauthen |
| 2006/0015182 A1 | 1/2006 | Tsou |
| 2006/0089646 A1 | 4/2006 | Bonutti |
| 2006/0136064 A1 * | 6/2006 | Sherman ................... 623/17.16 |
| 2006/0200245 A1 * | 9/2006 | Trieu ....................... 623/17.16 |
| 2006/0247776 A1 | 11/2006 | Kim |
| 2007/0005140 A1 | 1/2007 | Kim et al. |

OTHER PUBLICATIONS

U.S. Appl. No. 11/359,754, filed Feb. 21, 2006, entitled "Fabrication and Use of Biocompatible Materials for Treating and Repairing Herniated Spinal Discs," Inventor: Daniel H. Kim et al., Final Office Action executed May 9, 2008 and mailed May 22, 2008.

International Search Report mailed Aug. 21, 2008, in PCT/US06/18856, filed May 15, 2006, entitled "Fabrication and Use of Biocompatible Materials for Treating and Repairing Spinal Discs".

Written Opinion of The International Searching Authority mailed Aug. 21, 2008, in PCT/US06/18856, filed May 15, 2006, entitled "Fabrication and Use of Biocompatible Materials for Treating and Repairing Herniated Spinal Discs".

International Search Report mailed Sep. 18, 2006, in PCT/US06/16273, filed Apr. 28, 2006, entitled "Devices, Systems and Methods for Augmenting Intervertebral Discs".

Written Opinion of The International Searching Authority mailed Sep. 18, 2006, in PCT/US06/16273, filed Apr. 28, 2006, entitled "Devices, Systems and Methods for Augmenting Intervertebral Discs".

Hanks et al., "Comparison of cell viability on anorganic bone matrix with or without P-15 cell binding peptide," Biomaterials 25, pp. 4831-4836 (2004).

Lin et al., "Synthesis, surface, and cell-adhesion properties of polyurethanes containing covalently grafted RGD-peptides," Journal of Biomedical Materials Research, vol. 28, pp. 329-342 (1994).

Ozdemir et al., "Oxygen plasma modification of polyurethane membranes," Journal of Materials Science: Materials in Medicine 13, pp. 1147-1152 (2002).

Zhang et al., "A new peptide-based urethane polymer: synthesis, biodegradation, and potential to support cell growth in vitro," Biomaterials 21, pp. 1247-1258 (2000).

U.S. Appl. No. 11/120,639, filed May 2, 2005, entitled "Systems and Methods for Augmenting Intervertebral Discs", Non-Final Office Action Mailed May 12, 2010.

U.S. Appl. No. 11/120,639, filed May, 2, 2005, entitled "Systems and Methods for Augmenting Intervertebral Discs", Non-Final Office Action mailed Oct. 13, 2010.

* cited by examiner

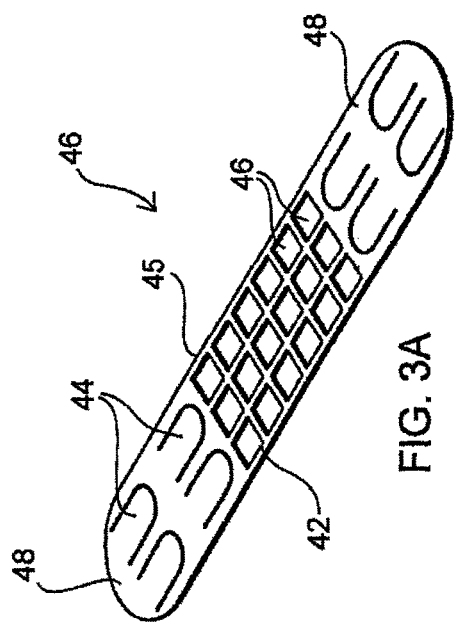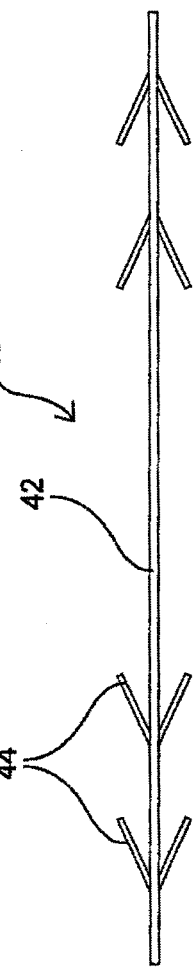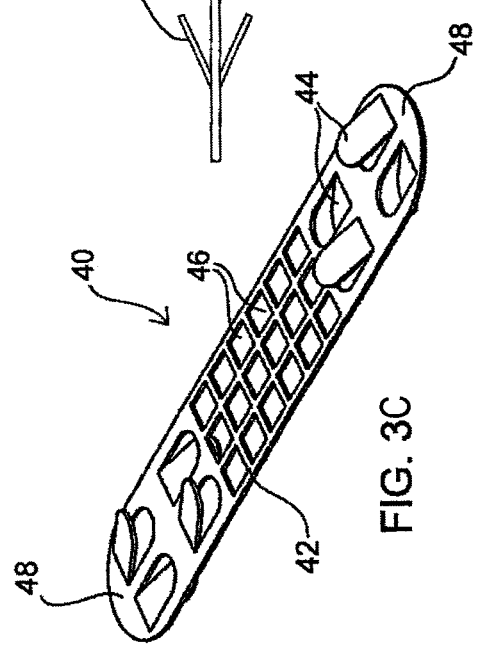

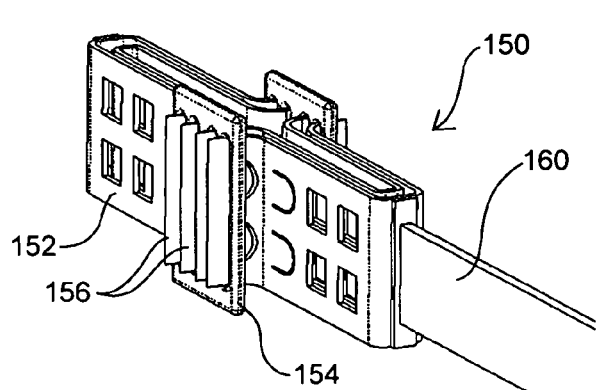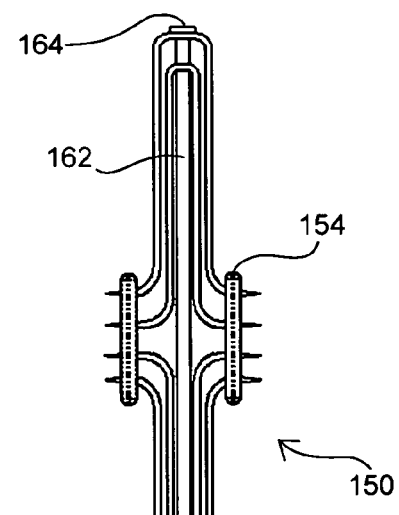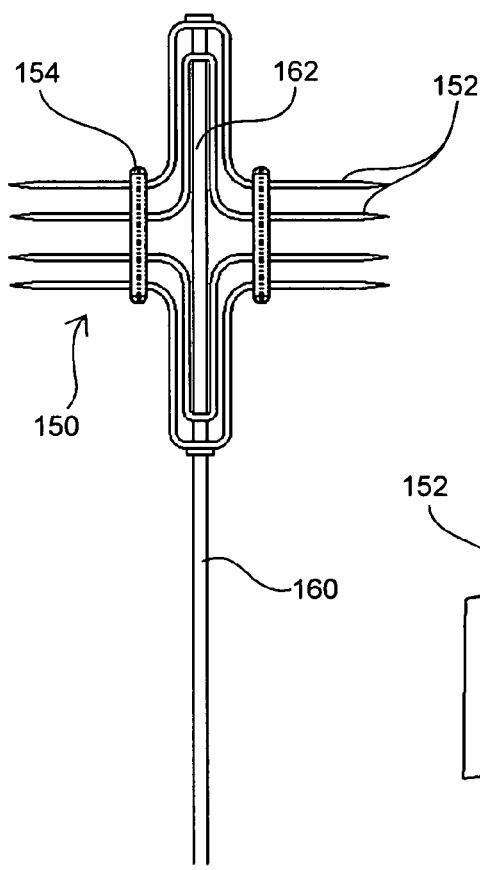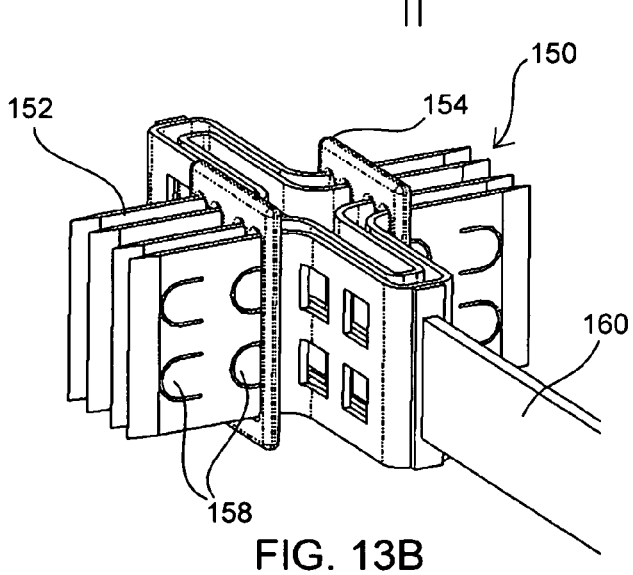
FIG. 13A
FIG. 13A'
FIG. 13B'
FIG. 13B

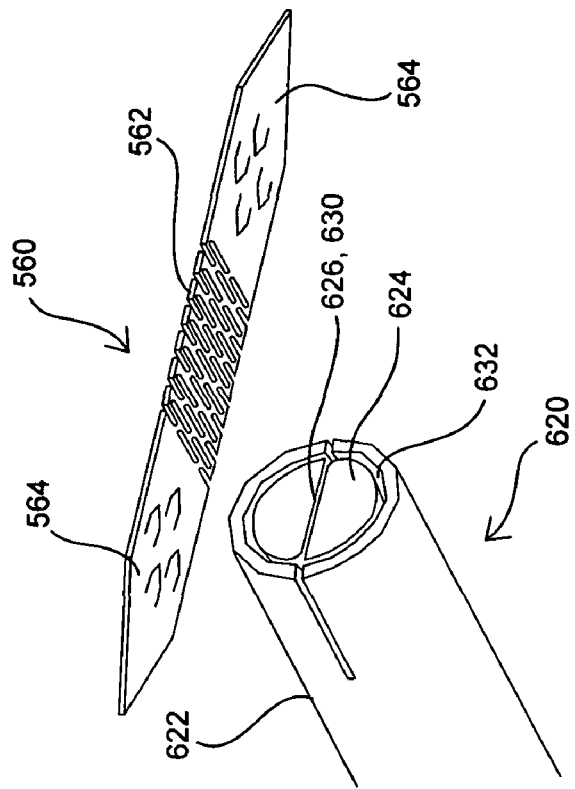
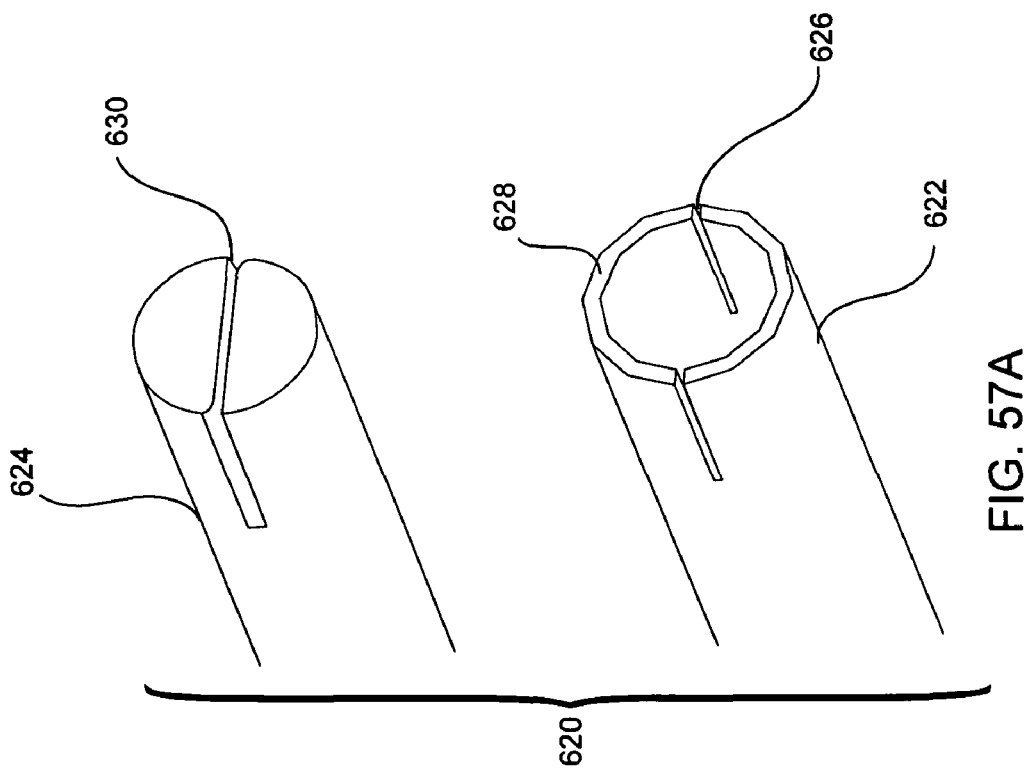
FIG. 57B
FIG. 57A

DEVICES, SYSTEMS AND METHODS FOR AUGMENTING INTERVERTEBRAL DISCS

CROSS-REFERENCE TO RELATED APPLICATIONS

This application is a continuation-in-part of U.S. patent application Ser. No. 11/120,639, filed May 2, 2005, which is incorporated by reference herein in its entirety.

FIELD OF THE INVENTION

The present invention is directed towards the minimally invasive repair of intervertebral discs.

BACKGROUND OF THE INVENTION

The spinal column is formed from a number of bony vertebral bodies separated by intervertebral discs which primarily serve as a mechanical cushion between the vertebral bones, permitting controlled motions (flexion, extension, lateral bending and axial rotation) within vertebral segments. The normal, natural intervertebral disc is comprised of three components: the nucleus pulposus ("nucleus"), the annulus fibrosis ("annulus"), and two opposing vertebral end plates.

The two vertebral end plates are each composed of thin cartilage overlying a thin layer of hard, cortical bone which attaches to the spongy, richly vascular, cancellous bone of the vertebral body.

The nucleus is constituted of a gel-like substance having a high (about 80-85%) water content, with the remainder made up mostly of proteoglycan, type II collagen fibers and elastin fibers. The proteoglycan functions to trap and hold the water, which is what gives the nucleus its strength and resiliency.

The annulus is an outer fibrous ring of collagen fibers that surrounds the nucleus and binds together adjacent vertebrae. The fibers of the annulus consist of 15 to 25 overlapping collagen sheets, called lamellae, which are held together by proteoglycans. The collagen fibers that form each lamellae run parallel at about a 65° angle to the sagittal plane; however, the fibers of adjacent lamellae run in opposite directions from each other. As such, half of the angulated fibers will tighten when the vertebrae rotate in either direction. This configuration greatly increases the shear strength of the annulus helping it to resist torsional motion. The annulus has a height of about 10 to 15 mm and a thickness of about 15 to 20 millimeters, occupying about ⅔ of the intervertebral space.

With aging and continued stressing, the nucleus becomes dehydrated and/or one or more rents or fissures may form in the annulus of the disc. Such fissures may progress to larger tears which allow the gelatinous material of the nucleus to migrate into the outer aspects of the annulus which may cause a localized bulge or herniation. In the event of annulus rupture, the nuclear material may escape, causing chemical irritation and inflammation of the nerve roots.

Posterior protrusions of intervertebral discs are particularly problematic since the nerve roots are posteriorly positioned relative to the intervertebral discs. Impingement or irritation of the nerve roots not only results in pain in the region of the back adjacent the disc, but may also cause radicular pain such as sciatica. Nerve compression and inflammation may also lead to numbness, weakness, and in late stages, paralysis and muscle atrophy, and/or bladder and bowel incontinence.

The most common treatment for a disc protrusion or herniation is discectomy. This procedure involves removal of the protruding portion of the nucleus and, most often, the annular defect does not get repaired. Typically, removal of the nucleus material is accomplished through the herniation site or a weakened portion of the annulus.

Discectomy procedures have an inherent risk since the portion of the disc to be removed is immediately adjacent the nerve root and any damage to the nerve root is clearly undesirable. Further, the long-term success of discectomy procedures is not always certain due to the loss of nucleus polposus which can lead to a loss in disc height. Loss of disc height increases loading on the facet joints which can result in deterioration of the joint and lead to osteoarthritis and ultimately to foraminal stenosis, pinching the nerve root. Loss of disc height also increases the load on the annulus as well. As the annulus fibrosis has been shown to have limited healing capacity subsequent to discectomy. A compromised annulus may lead to accelerated disc degeneration which may require spinal interbody fusion or total disc replacement.

If disc degeneration has not yet resulted in excessive herniation or rupture of the annulus, it may be desirable to perform a nucleus replacement procedure in which the degenerated nucleus is supplemented or augmented with a prosthesis while leaving the annulus intact. Advances have been made in materials for prosthetic nuclear implants which are relatively small and flexible (e.g., hydrogels), and are able to provide added height to the disc while simulating the natural disc physiology and motion. However, in order to implant a prosthesis within the nucleus cavity, an appropriately sized passageway through the annulus (i.e., an annulotomy) must be created. As with naturally-occurring defects in the annulus, the resulting surgical annulus defect may lead to post-implant complications. Currently accepted suturing techniques are of minimal value in light of the forces normally exerted on the annulus, including an inability to adequately resist explant of the nuclear implant.

Various annular defect repair techniques have been developed to occlude an aperture, whether surgically or naturally formed, within the annulus, which attempt to address the shortcomings of suturing. Many of these techniques include the implantation of devices, such as patches, membranes, stents and the like, to form a barrier across the annulus aperture in order to seal or occlude the aperture and/or to prevent explant of native or prosthetic nuclear material. While an improvement over conventional suturing, these annulus implants and repair techniques are limited in their ability to provide the extent of circumferential and radial competency to the annulus for long-term success. Additionally, where the disc repair procedure also involves the implantation of both annulus and nucleus augmentation devices, the implants and the steps necessary to implant both may counter-indicate each other.

Accordingly, it would be highly advantageous to be able to repair a degenerating or ruptured disc in a manner which obviates the inherent risks of discectomy procedures, and which augments the nucleus and/or annulus in a way that reduces the risk of re-herniation of the disc subsequent to repair. Additionally, it would be highly beneficial to provide a technique which allows disc repair in a minimally invasive requiring minimal steps and instrumentation to perform both annuloplasty and/or nucleus replacement procedures concurrently in a synergistic manner.

SUMMARY OF THE INVENTION

The present invention provides devices and systems for repairing the intervertebral disc. The devices include implantable disc augmentation components, certain of which are configured for implantation into the annulus, others of which are configured for implantation into the nucleus, and still others which are configured for implantation into both the annulus and the nucleus, or into the vertebral bodies. The subject annulus augmentation devices optionally provide a scaffolding which augments the disc annulus and which retains material (either natural or prosthetic) in the nucleus while allowing in growth there through. In addition to retaining material within the nucleus, the augmentation devices may enable passage of the prosthetic material from a location outside the disc to within the void space, where the void occupies at least a portion of the annulus and/or the nucleus. The devices for primary implantation into the nucleus include one or more materials for replacing the nucleus material which has escaped or otherwise been removed. The materials may be prosthetic, natural or a combination of both. The same or different materials may also be used to fill voids in the annulus as well.

Systems of the present invention include implantable disc augmentation devices as well as implantable prosthetic and/or natural materials for filling a void within the disc. The systems further include instruments for implanting the subject devices and prosthetic materials in a minimally invasive manner. The invention further includes methods directed to the minimally invasive repair of intervertebral discs where the methods may include one or more of the following procedures: implantation of one or more of the subject augmentation devices and implantation of prosthetic material within the annulus and/or nucleus. The inventive systems and methods are particularly useful in treating herniated or ruptured discs requiring nuclear and/or annular augmentation or repair.

These and other features, objects and advantages of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 3A and 3B show perspective and side views, respectively, of an embodiment of a disc augmentation device of the present invention having anchors in an undeployed state.

FIGS. 3C and 3D show perspective and side views, respectively, of the disc augmentation device of FIGS. 3A and 3B having anchors in a deployed state.

FIGS. 13A-13D illustrate various states of deployment of the integrated device of FIGS. 12A-12C.

FIGS. 57A-57E illustrate another tool for the delivery and implantation of certain disc augmentation devices of the present invention.

DETAILED DESCRIPTION OF THE INVENTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. For example, in this description and the following claims, the terms "anterior", "posterior", "superior" and "inferior" are defined by their standard usage in anatomy, i.e., anterior is a direction toward the front (ventral) side of the body or spinal motion segment; posterior is a direction toward the back (dorsal) side of the body or functional spine unit; superior is upward toward the head; and inferior is lower or toward the feet.

Figure 1A:
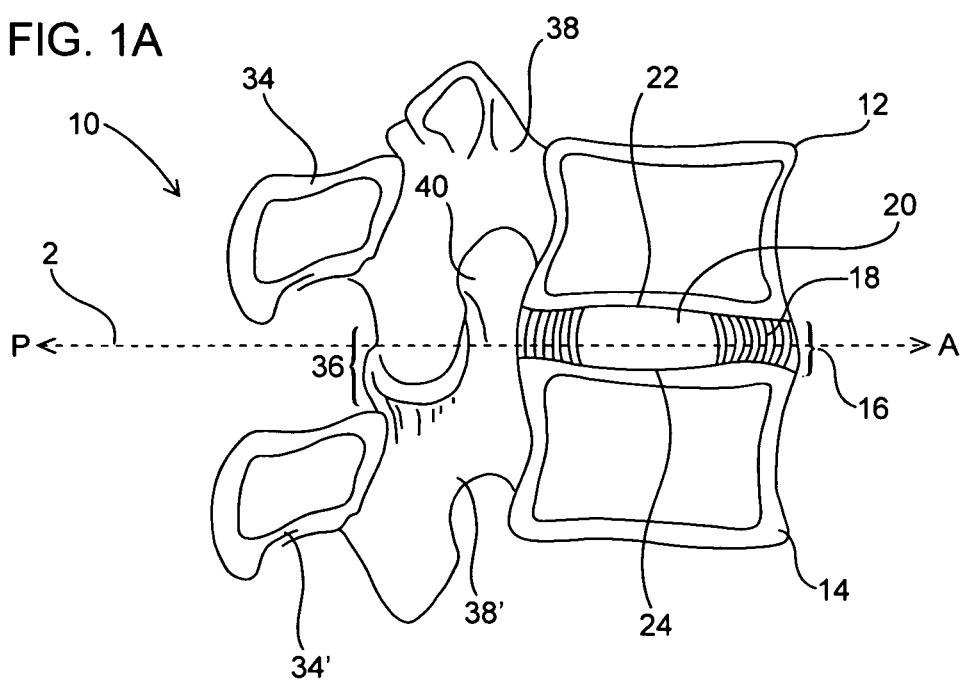
FIG. 1A shows a sagital cross-section of a spinal motion segment.
Figure 1B:
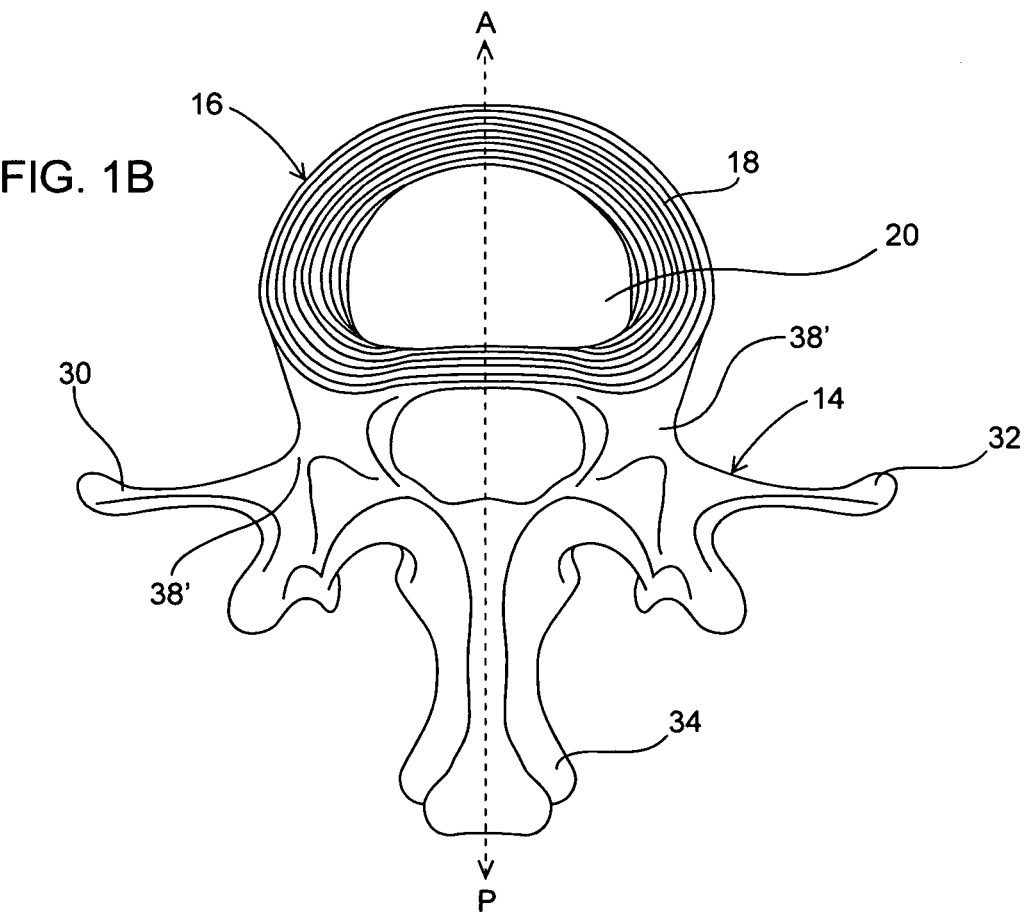
FIG. 1B shows a top axial view of a portion of the inferior vertebrae and the intervertebral disc of the spinal motion segment of FIG. 1A.

Referring now to FIGS. 1A and 1B, the general anatomy of a spinal motion segment 10 is illustrated. Axis 2 shows the anterior (A) and posterior (P) orientation of the spinal motion segment within the anatomy. A spinal motion segment includes the bony structures of two adjacent vertebrae (superior vertebral body 12 and inferior vertebral body 14), the intervertebral disc 16 (including the annulus fibrosis 18, the nucleus pulposus 20, and endplates 22, 24 of the vertebrae), and the ligaments, musculature and connective tissue (not shown) connected to the vertebrae. Intervertebral disc 16 substantially fills the space between the two vertebral bodies to support and cushion them, and permits movement of the two vertebral bodies with respect to each other and other adjacent spinal motion segments. Extending posteriorly from each of vertebral bodies 12 and 14 are left and right transverse spinous processes 30, 32 and a posterior spinous process 34, 34'. The vertebral bodies also include facet joints 36 and pedicles 38, 38' that form the neural foramen 40.

Figure 2A:
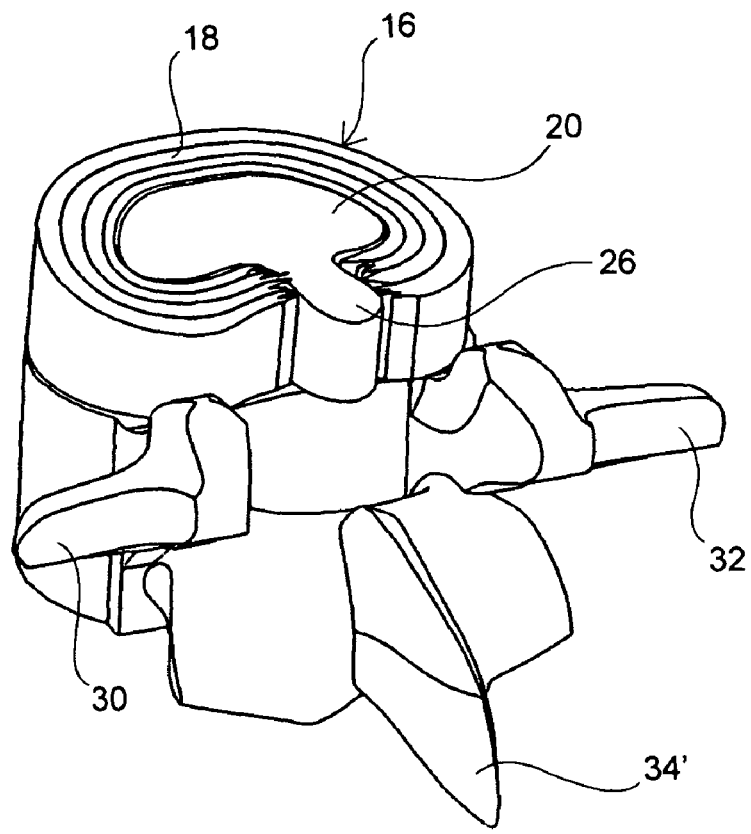
FIG. 2A shows a perspective view of a spinal motion segment having a herniation in the posterior portion of the disc.
Figure 2B:
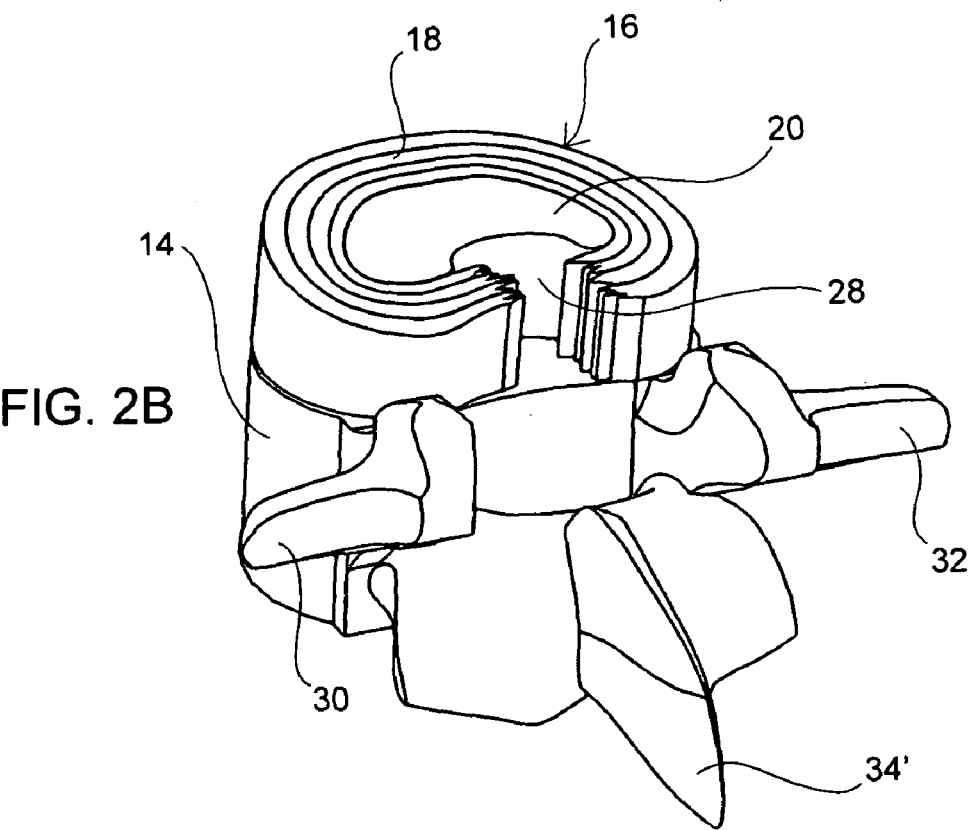
FIG. 2B shows a perspective view of the spinal motion segment of FIG. 2A after removal of the herniated segment.

As discussed above, progressive degeneration of the disc results in disc height loss where the superior vertebral body 12 moves inferiorly relative to the inferior vertebral body 14. Ultimately, this may result in herniation of the disc, as illustrated by herniated segment 26, shown in FIG. 2A, which protrudes beyond the posterior border of annulus 18. FIG. 2B illustrates the disc defect or void 28 created by a discectomy procedure in which the herniated portion of annulus 18 and nucleus 20 have been removed. Such a discectomy procedure may be performed, but is not required to be performed, prior to use of the devices and practice of the methods of the present invention.

The present invention is directed to augmenting the intervertebral disc, including the annulus and/or the nucleus, for treating or preventing degeneration and/or herniation of the intervertebral disc. This is accomplished by implantation of one or more augmentation devices within the disc, and most typically within the annulus, i.e., within an intra-annular space (i.e., between two adjacent lamellae or an inter-lamellar space), or within a sub-annular space (i.e., between the innermost lamella and the outer aspect of the nucleus), or within a void in the annulus but not necessarily within the annulus tissue itself. If a significant enough defect, e.g., a void, exists within the disc, either in the nucleus, the annulus or both, one or more prosthetic or natural materials may be additionally implanted within the void within at least a portion of the annulus and/or the nucleus of the affected disc.

Certain of the augmentation devices are configured to be wholly implantable within a void within the annulus or within an intra-annular space where no portion of the device extends beyond the inner and outer aspects or borders of the annulus. Other embodiments are configured to be partially implantable within an intra-annular space while another portion of the device is positioned within the nucleus, outside the annulus and/or within the intervertebral body upon implantation. More particularly, the augmentation devices may be configured to have a portion thereof or one or more components, struts or members which penetrate into an intra-annular space. Still yet, other configurations do not penetrate into any portion of the annulus or nucleus but rather into one or more of the intervertebral bodies between which the disc is situated.

The present invention provides various approaches to implantation of the subject augmentation devices. In one approach, at least a portion of an augmentation device is delivered to within the annulus in a direction substantially parallel to or tangential with a plane defined by the radius of curvature of the annulus (referred to at times herein as an "inline" or "parallel" approach). For example, a component of the device is aligned substantially parallel with the orientation of the lamellar layers. In another approach, at least a portion of an augmentation device is delivered in a direction substantially transverse to a plane defined by the radius of curvature of the annulus (referred to at times herein as a "transverse" or "perpendicular" approach). For device embodiments configured for penetration into an intervertebral body, one or more portions or components of the implant may be implanted at any angle relative to the annulus or lamellar planes, including at right angles to the vertebral endplates.

The augmentation devices may have an unexpanded or undeployed state to enable its minimally invasive delivery through a delivery tool, such as catheter or cannula, to the intra-annular or sub-annular implant site. Upon proper positioning of the implantable device at the implant site, the device is expanded or deployed. The transition from an undeployed state to a deployed state may require an active step such as mechanical actuation. Alternatively, the device may be configured to be self-expanding or self-deploying whereby, upon release from the delivery tool, the device achieves its expanded or deployed configuration within the disc. As such, the devices are preferably made of a shape memory material or an elastic or superelastic material, e.g., nickel titanium alloy (Nitinol), or a semi-rigid polymer.

The annular augmentation devices preferably have a configuration with a length and height sufficient to bridge across void 28. Typically, the length of a subject annular augmentation device is in the range from about 3 mm to about 30 mm, and most typically from about 5 mm to about 15 mm. Typically, the height of a subject annular augmentation device is in the range from about 2 mm to about 28 mm.

Another feature of the subject disc augmentation devices is that they have configurations which retain material within the nucleus while allowing for tissue in growth and may also allow for the delivery and implantation of a prosthetic material to within either or both the annulus and nucleus subsequent to implantation of the augmentation device(s) (although the devices and materials may be implanted in any order). For example, the disc implants may provide a scaffolding for promoting tissue in growth and/or allowing passage of the prosthetic implant material to within the nucleus as well as to within voids within the annulus not yet occupied by the disc device implant. The scaffolding may take the form of a frame having a planar configuration having apertures or which may be partially or wholly porous, or may be configured as a mesh, webbing, fabric or an arrangement of struts having one or more openings therein to allow for the passage of in growth. Implanting the prosthetic material after implantation of a disc augmentation device helps to retain the prosthetic material within the disc prior to and during solidification or curing of the material. Without such a retaining structure, the prosthetic material may seep or leak out of the disc prior to implantation of the disc augmentation devices. Alternatively, the retaining structure may be implanted subsequent to the material used to fill the void, for example, where the viscosity of the material is such that seepage or leakage prior to implantation of the retaining scaffold is unlikely.

It is preferred that the implant materials exhibit mechanical properties, swelling pressures and/or diffusion capabilities similar to the natural tissue site, i.e., annulus or nucleus, into which they are implanted. As such, more than one prosthetic and/or natural materials or varying compositions of the same type of material may be implanted where, for example, a first material is used to fill a void in the nucleus and a second material is used to fill a void or voids within the annulus. The different materials may be selected to more closely mimic the physical characteristics of the host tissue, e.g., the prosthetic material implanted in the annulus may be more fibrous and resilient than that which is implanted in the nucleus.

Alternatively, a single type of implant material may be used where the void in the nucleus and in the annulus are filled by a single injection application, where upon filling the nucleus, the material is caused to back fill into the annulus. The curing process may be modified such that the portion of the material within the nucleus is caused to harden or solidified to a less degree than that the portion of the material within the annulus. This may occur without much intervention as the amount of UV radiation reaching the nucleus will be less than the amount reaching the annulus as the annulus serves to buffer the nucleus. The same may be the case when diffusing a curing chemical into the implanted material. Alternatively, the implantation and curing may take place in a two phase process where the annulus is not filled and cured until after the nucleus has been filled and separately cured.

The prosthetic materials of the present invention may be initially in the form of a solid or fluid. The solids may take the form of a single structure, e.g., a cord or spherical or cylindrical shaped structure, a plurality of beads or particles, or a powder so as to be easily deliverable through or within the implanted disc device(s). The fluids may be in the form of a gel, liquid or other flowable material. In any of these forms, the material is selectively delivered in an amount to increase the disc volume, pressure and/or height. For example, material in the form of a cord which may be cut or truncated to provide a cord segment having a length which provides an implant having a volume (i.e., when folded upon itself) sufficient to fill a void in the nucleus, and possibly in the annulus as well. Subsequent to delivery within the disc void(s), the prosthetic material(s) may remain in the same form or take another form either by curing by the application of heat or UV light, by absorption of surrounding fluids, i.e., where the prosthesis material is hydrophilic, or by the application of another substance or chemical which reacts with the material in a way that changes its form.

Any suitable prosthetic materials may be used with the present invention. Examples of suitable materials include but are not limited to biocompatible materials such as polyurethane, polyurethane foams, hydrophilic polymers, hydrogels, homopolymer hydrogels, copolymer hydrogels, multi-polymer hydrogels, or interpenetrating hydrogels. The materials may also include natural or biologic material which are autologous, allograft, zenograft, or bioengineered. Examples of such biologic materials include but are not limited morselized or block bone, hydroxy apetite, collagen or cross-linked collagen, muscle tissue, fat, cellulose, keratin, cartilage, protein polymers, etc. which may be transplanted or bioengineered materials.

The disc implant material(s) and/or disc implant device(s) may be impregnated, coated or otherwise delivered with one or more therapeutic agents, including but not limited to, drugs (e.g., analgesics, antibiotics, steroids, etc.), growth factors, extracellular matrices (ECMs), etc. which may be dispersed in a regulated or time-released fashion.

Various exemplary embodiments of the disc augmentation systems and disc repair methods of the present invention are now described in greater detail, however, such description is not intended to be limiting but exemplary of the present invention. Any combination of features, materials, functions and physical characteristics described above may be applied to each of the devices and/or materials of the present invention.

FIGS. 3A-3D illustrate one embodiment of a disc augmentation device 40 of the present invention. Device 40 has a thin planar structure 42 which is designed to be implantable within an intra-annular space, e.g., inter-lamellarly (between two adjacent lamellae), to bridge a disc defect or void 28. Typically, more than one and as many as eight or more structures 42 are used collectively in a stacked arrangement, where at least one lamella lies between adjacently implanted structures. Depending on the length of the device, it may be straight (shorter device segments) or have a radius of curvature along its length (longer device segments) which matches that of the intra-annular circumference.

Figure 4A:
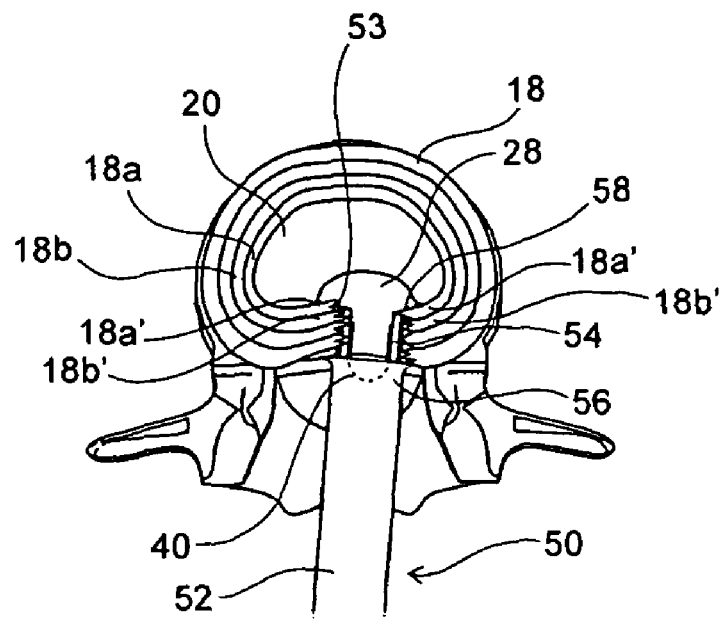
FIGS. 4A-4G illustrate various steps for implanting the disc augmentation device of FIGS. 3A-3D and for implanting a prosthetic material according to methods of the present invention.
Figure 4B:
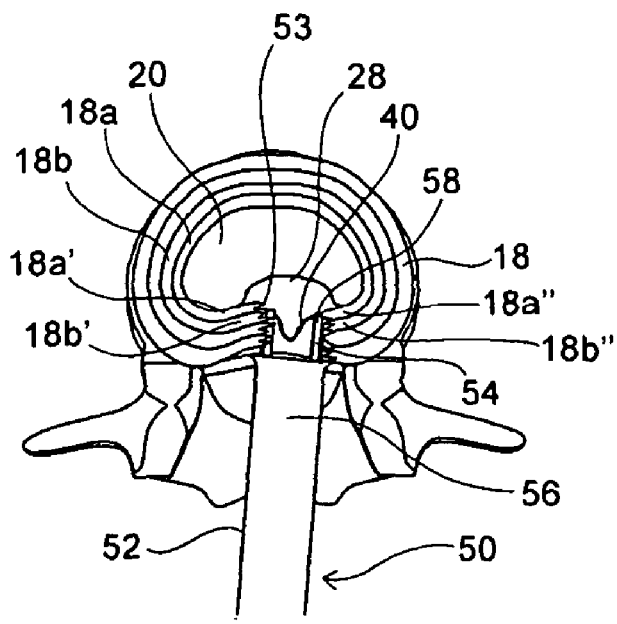

Each structure 42 has a central portion 45 flanked by end portions 48 where central portion 45, when implanted, is positioned within disc defect 28 and end portions extend substantially laterally of disc defect 28. Central portion 45 has a mesh configuration or includes a plurality of openings or apertures 46 which extend through the thickness of structure 42 to allow for passage of an implant material as mentioned above. Each end portion 48 has one or more laterally extendable anchors 44. Anchors 44 may be formed by cut outs within structure 42 which remain connected to body 42 so as to be hinged at a distal end and flarable or biased from body 42 at a proximal end, as illustrated in FIGS. 3C and 3D, to function as barbs once operatively positioned within the annulus. As with the entirety of structure 42, anchors 44 may be fabricated from a super elastic memory material which is activated by body temperature to achieve a flared condition subsequent to implantation. The anchor cut-out and aperture patterns of device 40 may be formed by electro-discharge machining (EDM), laser cutting, injection molding, photo-chemical etching (PCE), a casting process or by other suitable means from a relatively thin sheet of material, e.g., having a sheet thickness from about 0.1 mm to about 4 mm. As illustrated in FIG. 4B, device 40 is bendable or foldable at central section 45 about an axis transverse to the length of device 40 to reduce its profile for purposes of delivery through a cannula or catheter.

Various steps of a method of implanting a plurality of devices 40 are illustrated in FIGS. 4A-4G. A delivery tool 50 is provided having an outer sheath 52, which may be a cannula or catheter or the like. Housed within sheath 52 is a plurality of devices 40 (not shown) which may be provided in a stacked or sequential arrangement, such as within a pre-loaded cartridge, which is loaded into delivery sheath 52. While sheath 52 is illustrated having a square or rectangular cross-section so as to best accommodate the structure of device 40, the sheath may have any suitable cross-sectional shape to accommodate the disc implants.

Figure 4C:
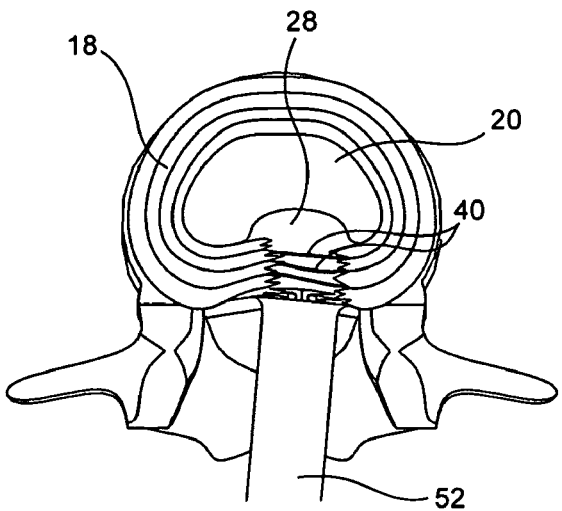

After surgical access is made, the distal end 56 of delivery tool 50 is positioned within or at the outer aspect of disc void 28. As illustrated in FIG. 4A, rails or guide members 54 are distally extended into disc void 28 to the most distal or internal lamellar layer, e.g., between lamellae 18a and 18b, into which a device 40 is to be implanted. Guide members 54 have outwardly projecting feet 58 which are configured to be inserted between the cut edges of adjacent lamellae and provide exit ramps to direct the ends of a device 40 to within an intra-lamellar space. A plunger or pusher (not shown) may be slidably engaged within sheath 52 or some other actuator mechanism may be employed to distally advance a device 40 in a folded or unexpanded configuration along guide members 54, as illustrated in FIG. 4B. The ends of device 40 are directed outwardly by feet 58 and guided between lamellar ends 18a', 18b' and 18a'', 18b'', respectively, as shown in FIG. 4C. Upon achieving the necessary temperature, anchors 44 expand outwardly to their flared condition, securing device 40 within the intra-lamellar space. The process is repeated as necessary for the selected number of implants 40, with each successive implant is inserted in an inter-lamellar layer that is more proximal (towards the outer circumference of the annulus) than the one before.

Figure 4D:
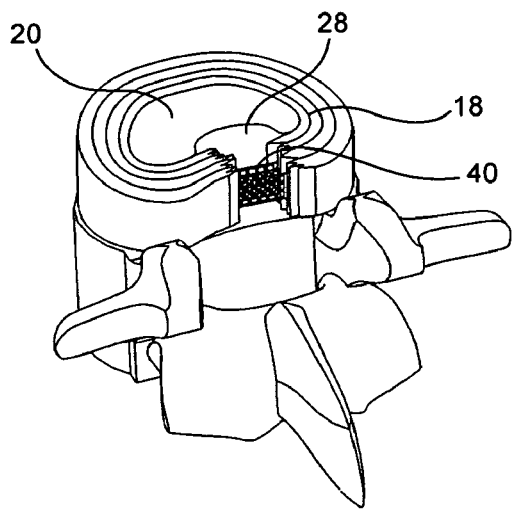
Figure 4E:
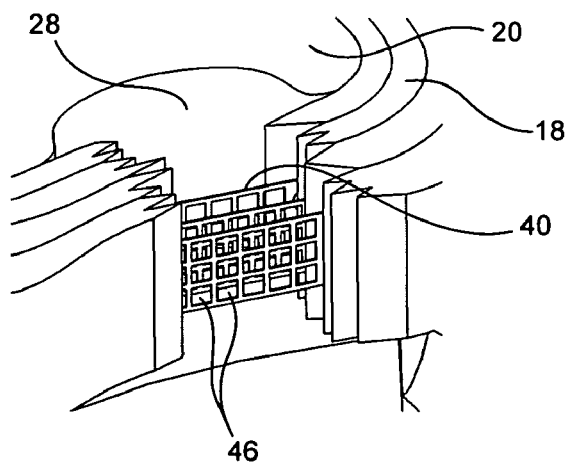
Figure 4F:
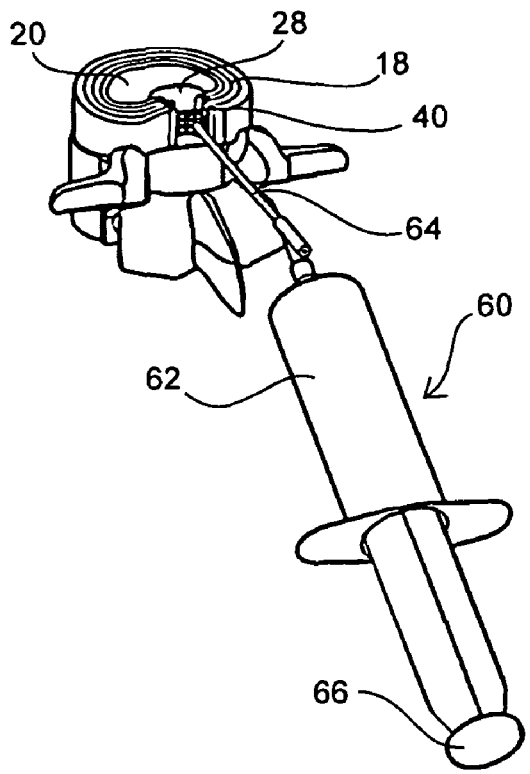
Figure 4G:
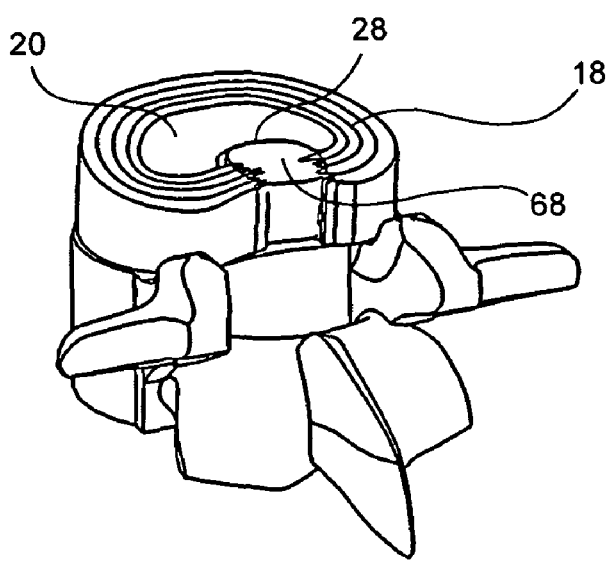

As shown in the perspective views of FIGS. 4D and 4E, apertures 46 within each of the implanted plurality of devices 40 provide fluid communication between the devices and into disc void 28. This provides a pathway from outside the annulus 18 into disc void 28 for delivery of the prosthetic implant material, as described above. In one embodiment, an injector device 60, as illustrated in FIG. 4F, having a syringe 62 containing an amount of the prosthetic material is coupled to a tube 64 which is sized to fit through the minimally invasive access site. The distal end of the tube is positioned either at the outermost disc implant 40, or if small enough, may be inserted through apertures 46 within one or more of the implants. After tube 64 is properly positioned, plunger 66 may be advanced to extrude a sufficient amount of the prosthetic material 68 to fill the portion of disc void 28 within nucleus 20 as well as within the intra-annular spaces partitioned by the disc devices 40. Upon filling the entirety of the void 28, or intermittently throughout the injection process, the injected material 68 may be allowed to cure or be actively cured, if such is necessary, as described generally above, to provide a plug or the like that extends from the nucleus 20 to the outer aspect of the annulus 18.

The augmentation devices of the present invention are designed to be implantable within an intra-annular space, e.g., inter-lamellarly (between two adjacent lamellae), to bridge a disc defect or void as described above. Typically, more than one and as many as eight or more structures are used collectively in a stacked arrangement, where at least one lamella lies between adjacently implanted structures. Depending on the length of the device, it may be straight (shorter device segments) or have a radius of curvature along its length (longer device segments) which matches that of the intra-annular circumference.

Figure 5A:
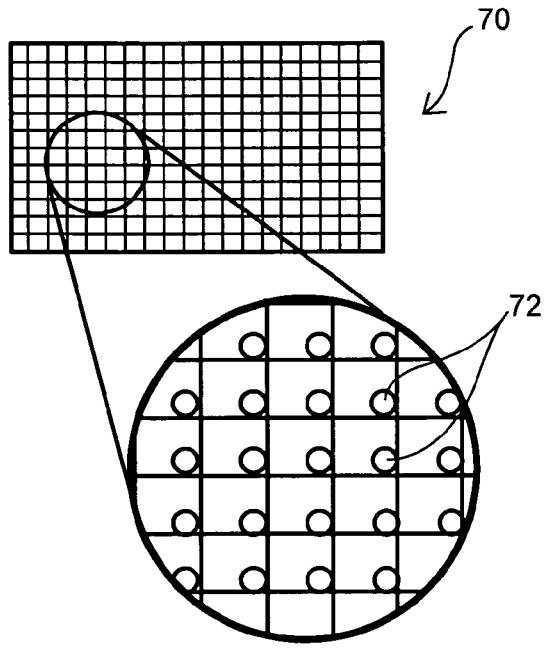
FIGS. 5A and 5B show planar and perspective views, respectively, of another disc augmentation device of the present invention.
Figure 5B:
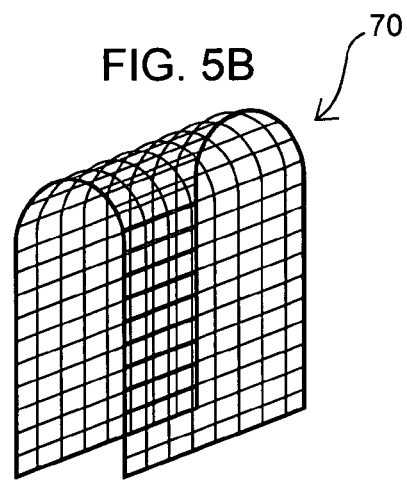

FIGS. 5A and 5B illustrate another embodiment of a disc augmentation device 70 having a thin planar configuration entirely made of a mesh material. With such a configuration, a prosthetic material may be impregnated within or coated on device 70, i.e., the smaller and more abundant apertures may be sized to hold solid particles 72 of prosthetic material or another composition or agent as listed above.

Figure 6A:
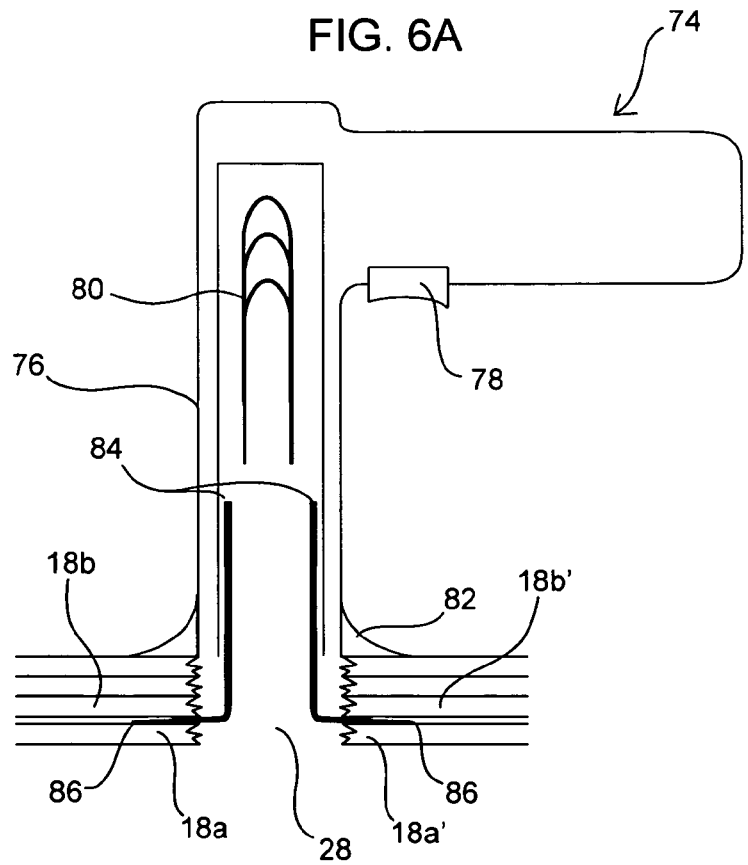
FIGS. 6A-6E illustrate various steps for implanting the disc augmentation device of FIGS. 5A and 5B and for implanting a prosthetic material according to methods of present invention.

As with device 40, device 70 is made of a material (e.g., Nitinol) which is flexible or deformable, allowing it to be foldable or bendable about a central portion to form a U-shaped structure which can be delivered in a minimally invasive manner. The U-shape allows a plurality of devices 70 to be provided in a stacked arrangement, such as in a cartridge 80, which can be pre-loaded into the barrel or sheath 76 of a delivery device 74, as illustrated in FIG. 6A. Delivery device 74 is configured to enable semi-automatic delivery and deployment of the plurality of devices 70 by means of an actuator or trigger mechanism 78. Distal end 82 of delivery device 74 may have a radially expandable portion to provide a stable support against the outer aspect of the annulus and to ensure alignment with defect 28.

Figure 6B:
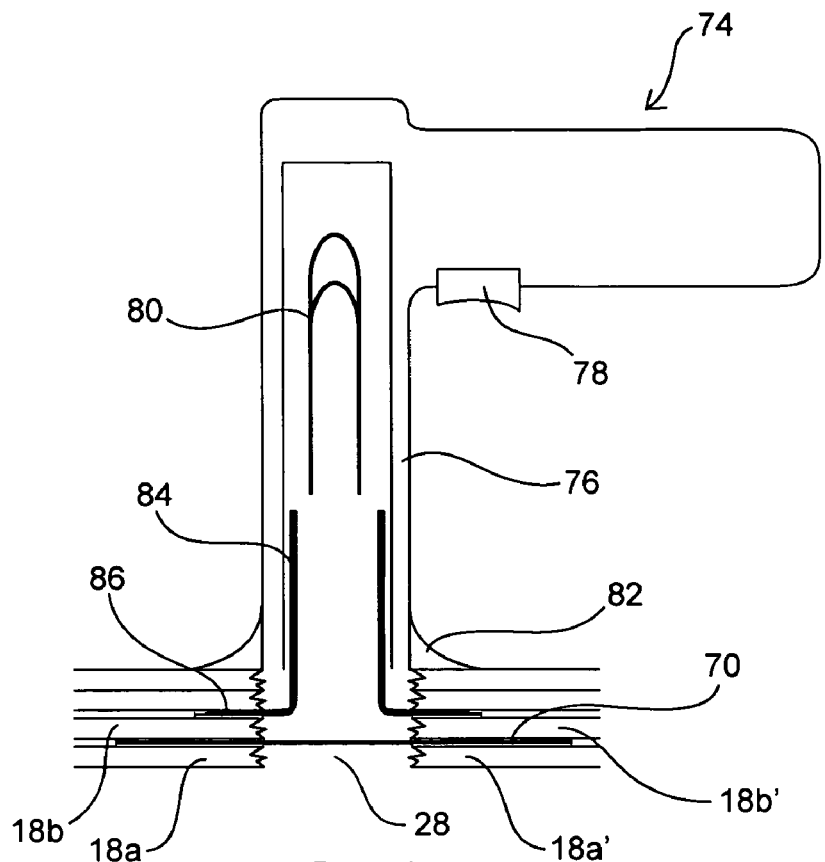
Figure 6C:
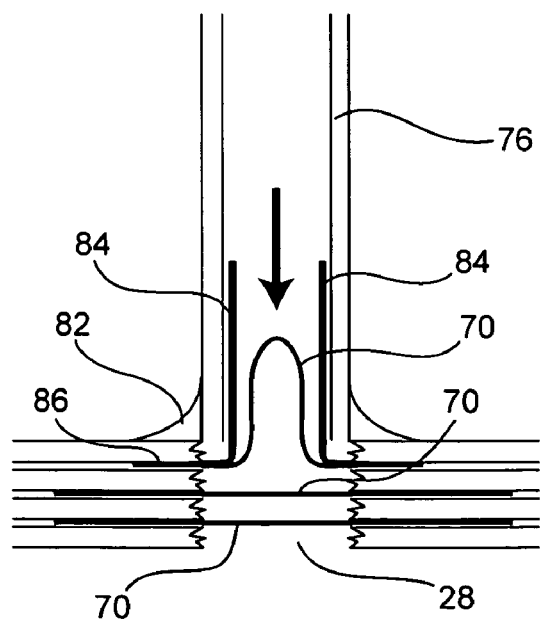

In use, after insertion of barrel 76 into the access site and abutment of the distal end 82 against the annulus at the defect site 28, guide members 84 are distally extended from distal end 82 within void 28 to the most distal intra-lamellar layer into which a device 70 is to be implanted. Guide members 84 have outwardly extending feet 86 which may have a bladed configuration to facilitate separation of cut ends 18a, 18b and 18a', 18b' of the lamellar layers for insertion of a device 70. A first device 70 is advanced through sheath 76 and guided by guide members 84 to the target intra-lamellar layer. Because the ends of device 70 are biased outwards, as they pass feet 86, they urge themselves to within the intra-lamellar space. Feet 86 of guide members 84 are then withdrawn from the intra-lamellar layer and retracted proximally to the next intra-lamellar layer into which a device 70 is to be implanted, as illustrated in FIG. 6B. The process is repeated until a desired number of devices 70 are implanted within the annulus (see FIG. 6C).

Figure 6D:
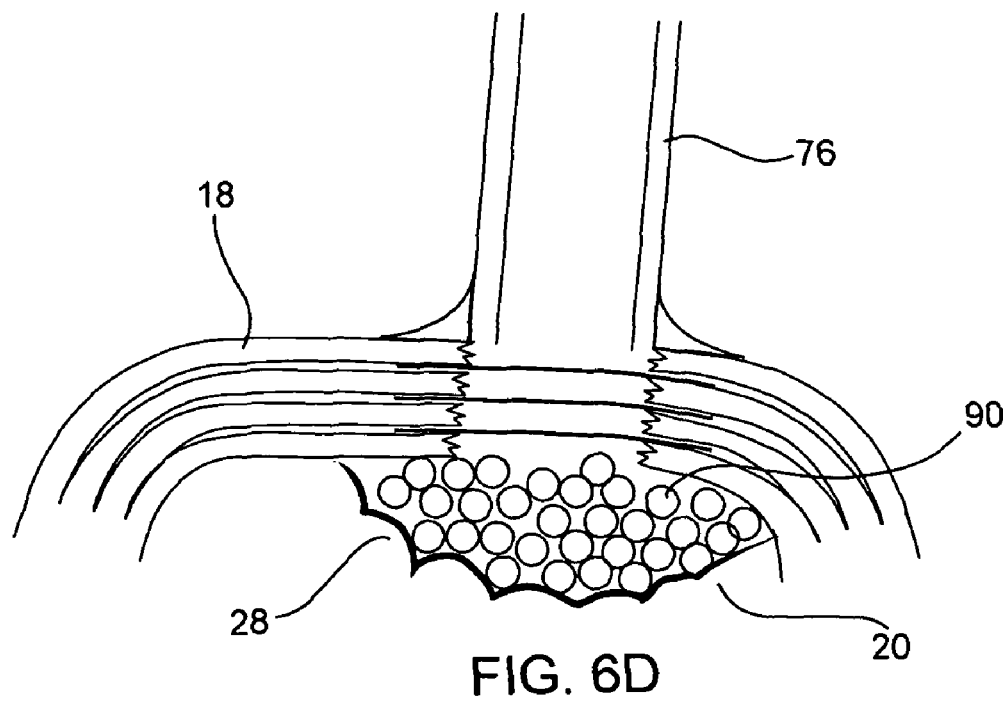
Figure 6E:
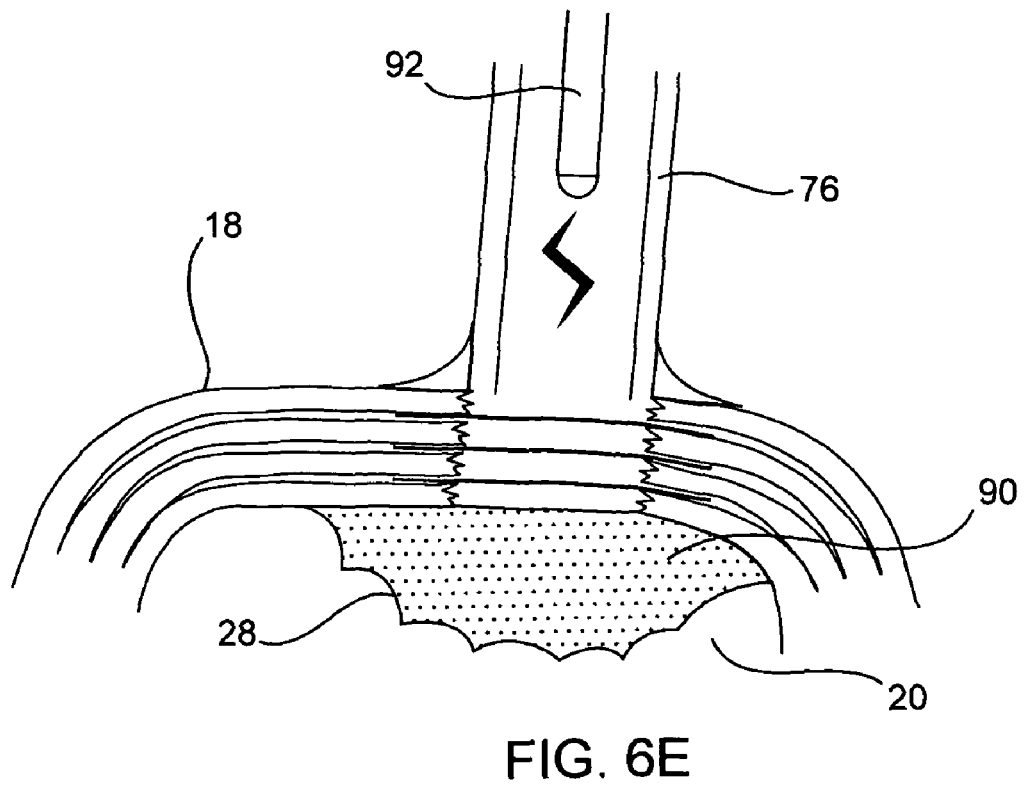

Next, void 28 is filled with a prosthetic material, which may be delivered through delivery device 74 or by means of another instrument. As illustrated in FIG. 6D, solid particles or a powder 90 of a prosthetic material is delivered into at least the portion of void 28 within nucleus 20. As mentioned above, the same prosthetic material may be used to fill both the nucleus and the annulus or different materials may be used to fill each. In either case, the curing process may involve curing all of the implanted material(s) at the same time or curing the material within the nucleus first followed by filling and curing the material within the annulus. Here, an amount of material 90 sufficient to fill only the nucleus portion of void 28 is delivered and then cured by exposure to UV radiation, as illustrated in FIG. 6E, or other curing methods. The portion of void 28 within in annulus 18 may now be filled with the same or a different material and cured, or otherwise left alone to be filled in by the natural healing process.

Figure 7A:
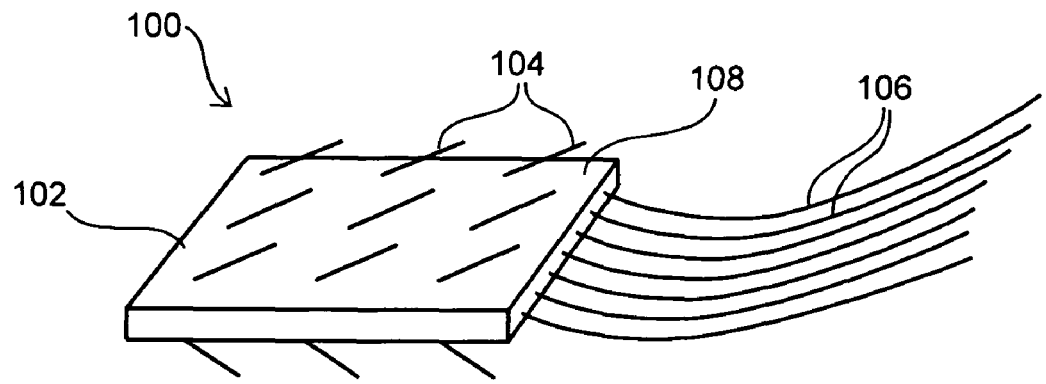
FIGS. 7A and 7B illustrate perspective and side views, respectively, of one side of another disc augmentation device of the present invention.
Figure 7B:
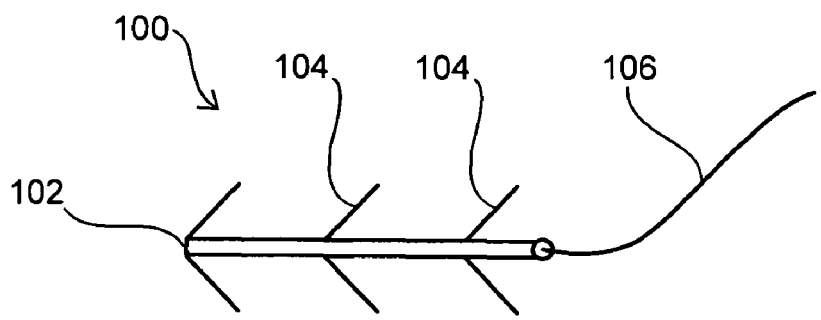
Figure 8:
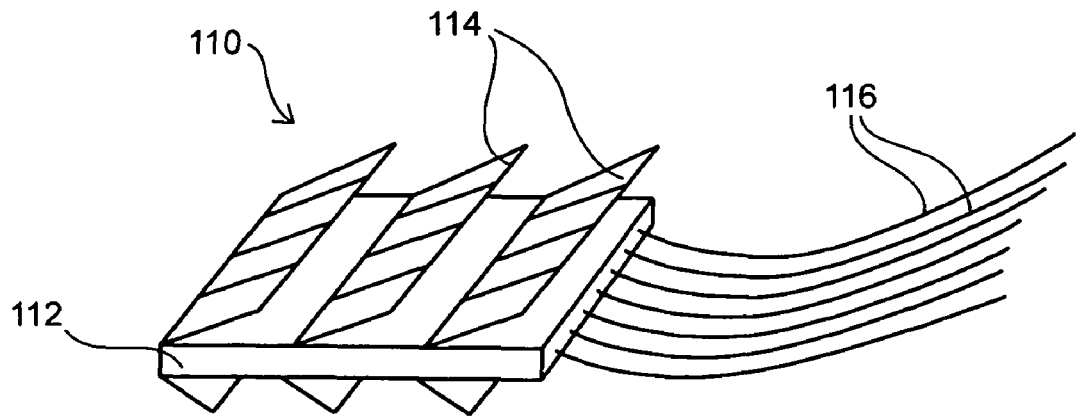
FIG. 8 is a perspective view of one side of another disc augmentation device of the present invention.
Figure 9A:
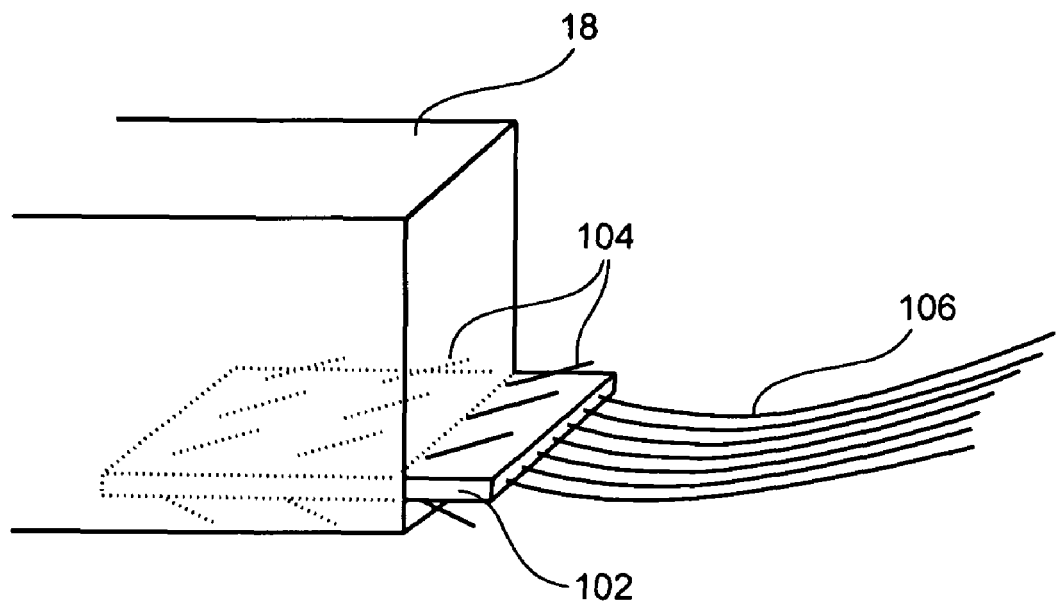
FIGS. 9A-9F illustrate various steps for implanting the disc augmentation device of FIGS. 7A and 7B and for implanting a prosthetic material according to methods of present invention.
Figure 9B:
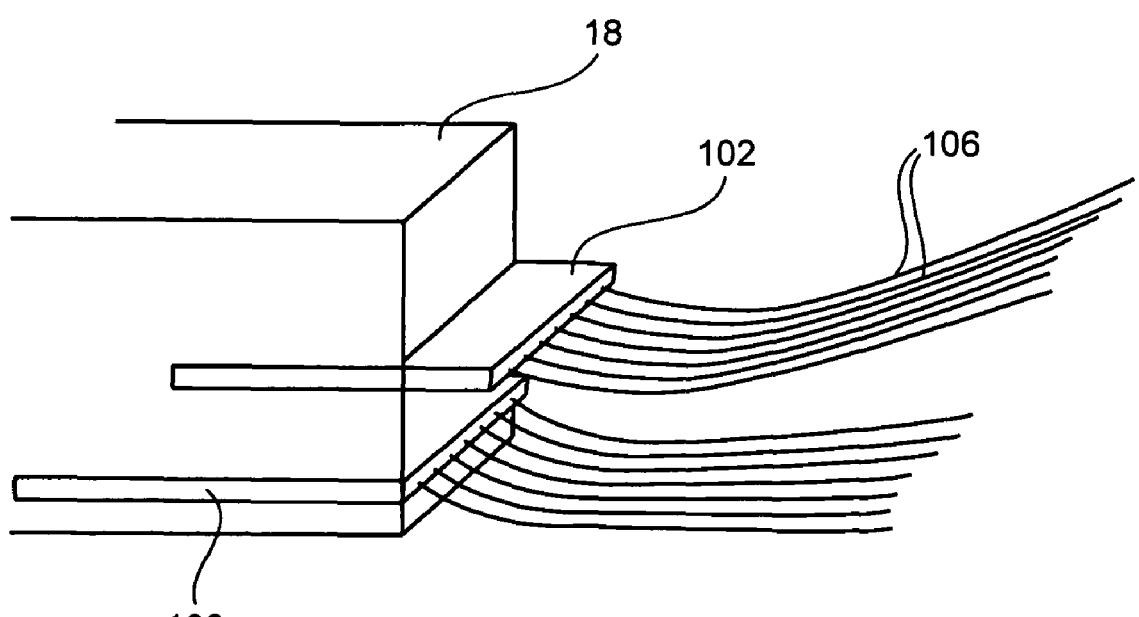
Figure 9C:
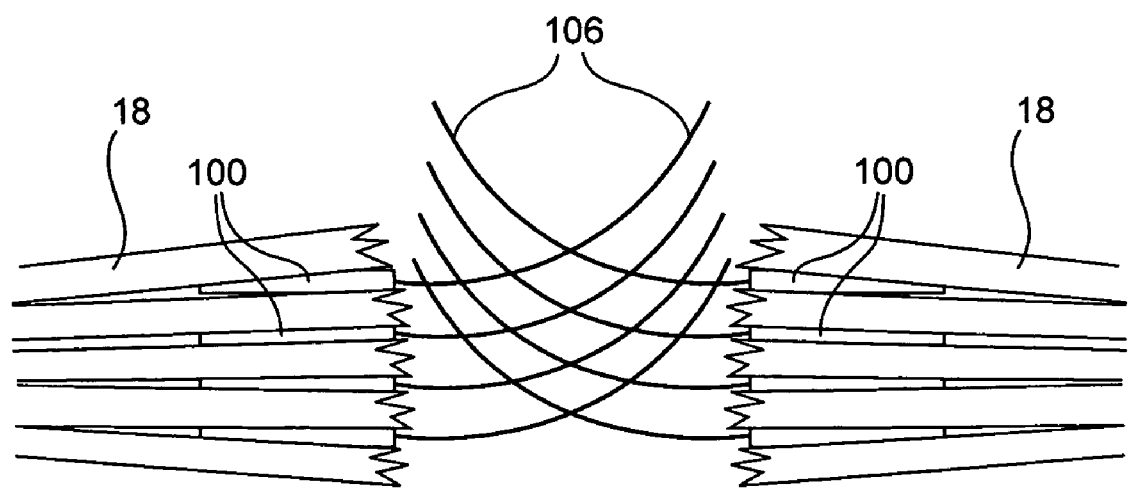

FIGS. 7A and 7B illustrate another implantable device 100 for augmenting the disc. Device 100 includes a planar structure 102 configured for insertion within an intra-lamellar space. A plurality of flexible wire barbs 14 extend from structure 102 in an angled fashion towards the proximal end 108 of structure 102, and a plurality of sutures or wires extend from proximal end 108. FIG. 8 illustrates a device 110 which is a variation of the device 100 having a plurality of planar anchors 114 in place of barbs 104. As illustrated in FIG. 9A, each of these devices is implanted within an intra-lamellar plane on a side of an annular defect. Upon entry into the lamellar plane, barbs 104 (or anchors 114) are compressed against structure 102 (or structure 112) facilitating easy insertion within between the adjacent lamellae. After insertion of the device, barbs 104 will expand outwardly and resist backward movement of structure 102. The process may repeated to implanted any desired number of implants within annulus 18. For each device 100 implanted within one side of an annular defect, a second device 100 is implanted within the lamellar layer directly opposing the first implanted device 100 as illustrated in FIG. 9C. As such, two oppositely implanted devices 100 function in tandem as a pair to close at least a portion of the annular defect.

Figure 9D:
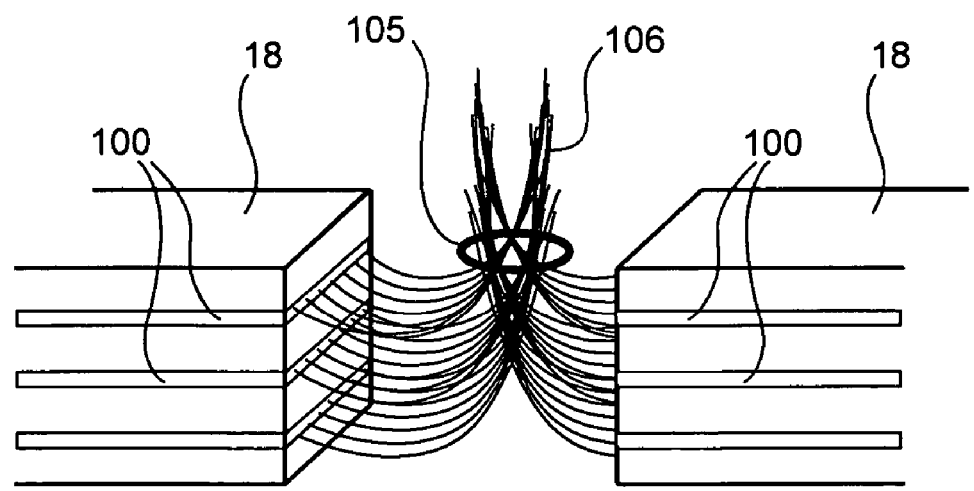
Figure 9E:
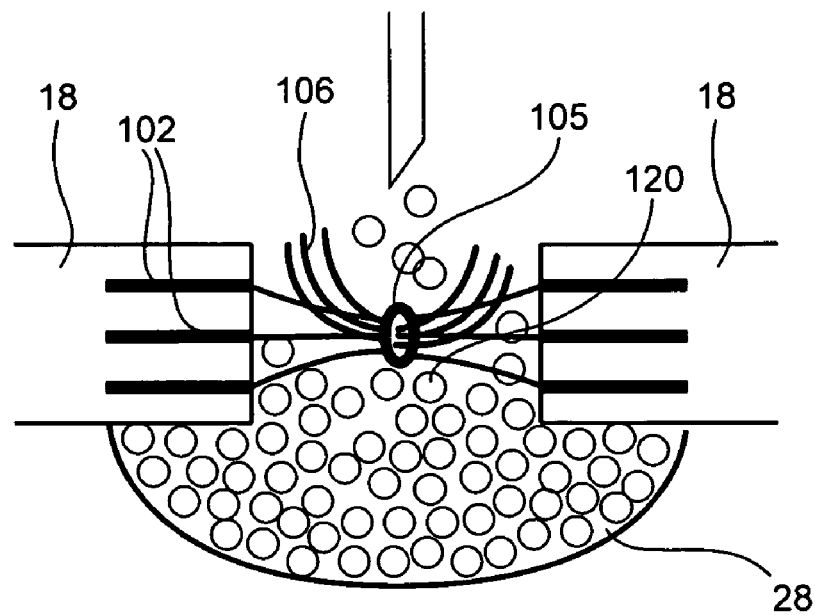
Figure 9F:
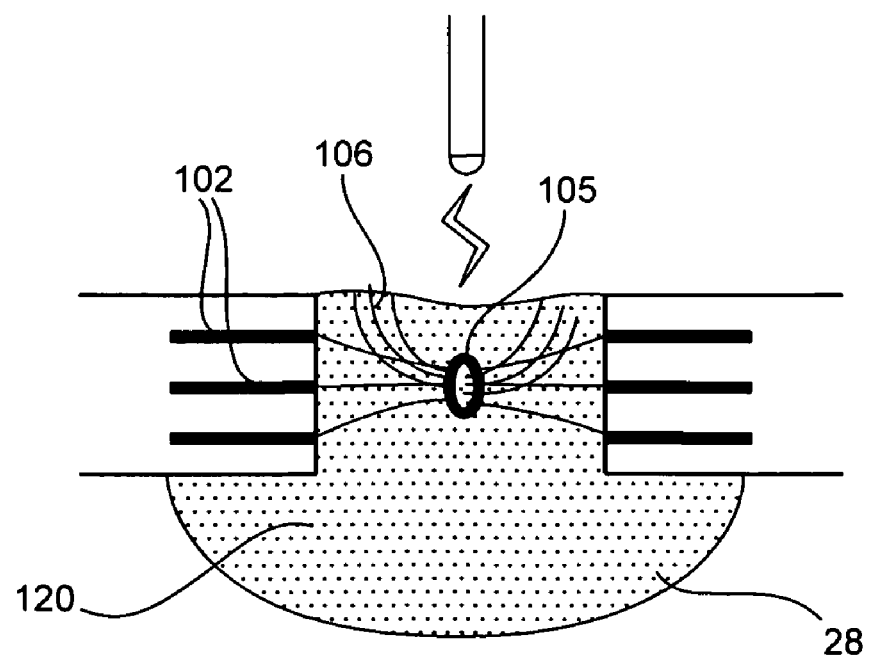

When all of the devices 100 have been inserted, all of the trailing proximal sutures 106 are collectively synched to pull together opposing sides of annulus 18 and tied together with a knot tie 105 or similar means as illustrated in FIG. 9D. The collectively tied sutures 106 form a sort of webbing that allows for the passage of one or more implantable materials 120, either in liquid or solid form, to within defect 28, in both the nucleus and annulus, as illustrated in FIG. 9E. The implanted material 120 is then cured in one or more of the manners described above, as illustrated in FIG. 9F.

Figure 10A:
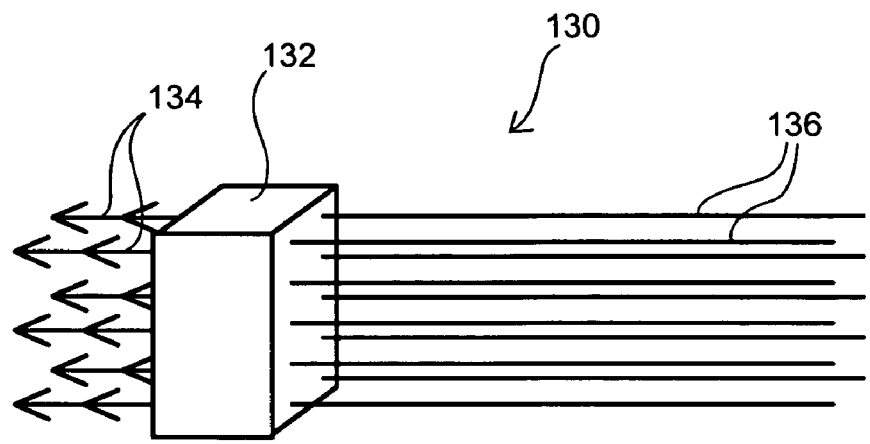
FIGS. 10A-10C illustrate another disc augmentation device of the present invention.

FIG. 10A illustrates another component 130 of a disc augmentation device to be used in a pair. Component 130 includes a planar endplate or block 132 which has dimensions which has a cross-sectional area and shape which substantially matches the cross-sectional area and shape of a disc annulus into which it is to be implanted Extending from a distal end of end plate 132 is a plurality of anchors 134 preferably arranged in columns (and rows) and having barbs 138. As with the device described above, barbs 138 have a compressed configuration prior to insertion of anchors 134 into an annulus (see FIG. 10B) and expand upon insertion into the annulus (see FIG. 10C). Extending from a proximal end of endplate 132 are sutures or wires 136.

Figure 11A:
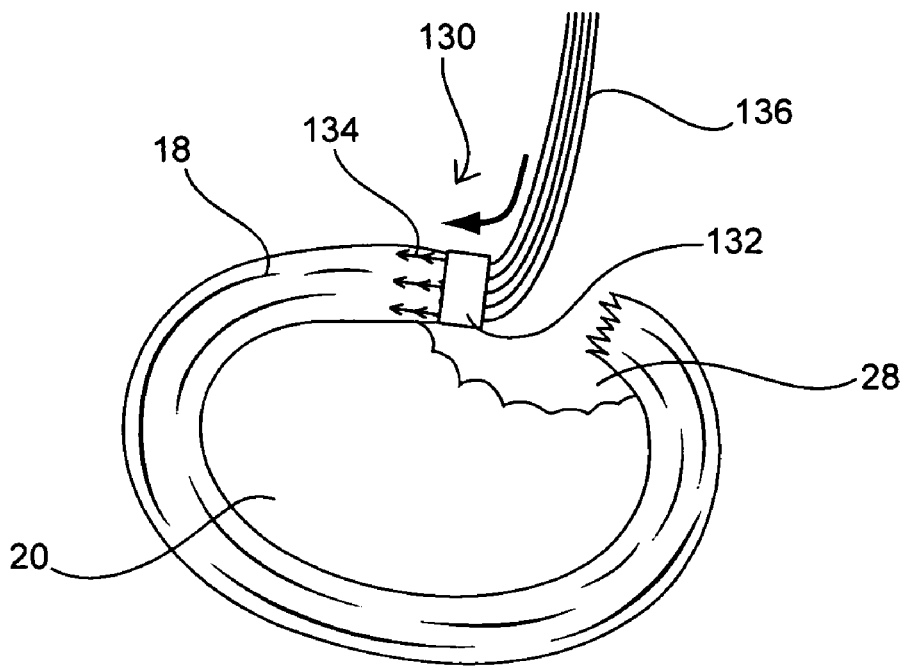
FIGS. 11A-11E illustrate various steps for implanting the disc augmentation device of FIGS. 10A10C and for implanting a prosthetic material according to methods of present invention.
Figure 11B:
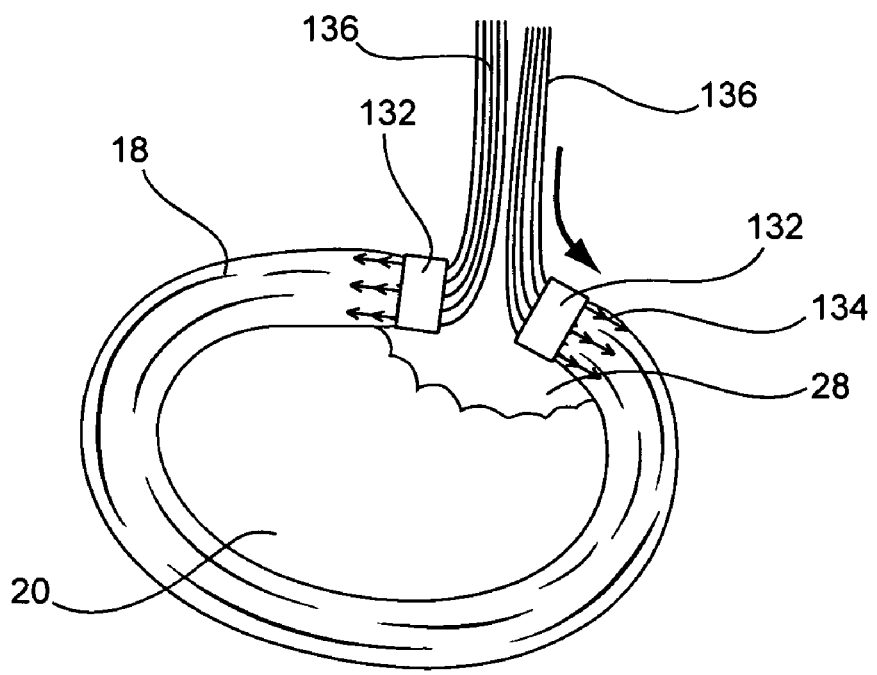
Figure 11C:
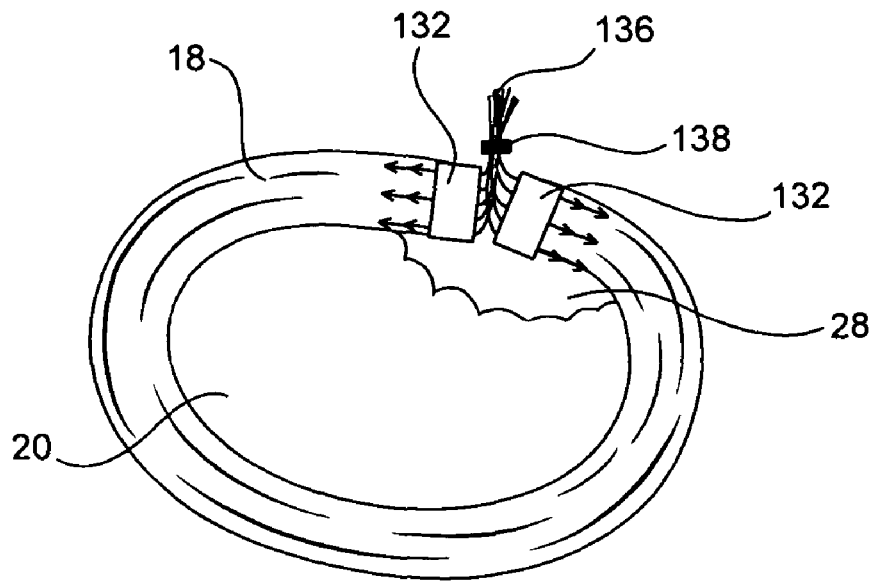
Figure 11D:
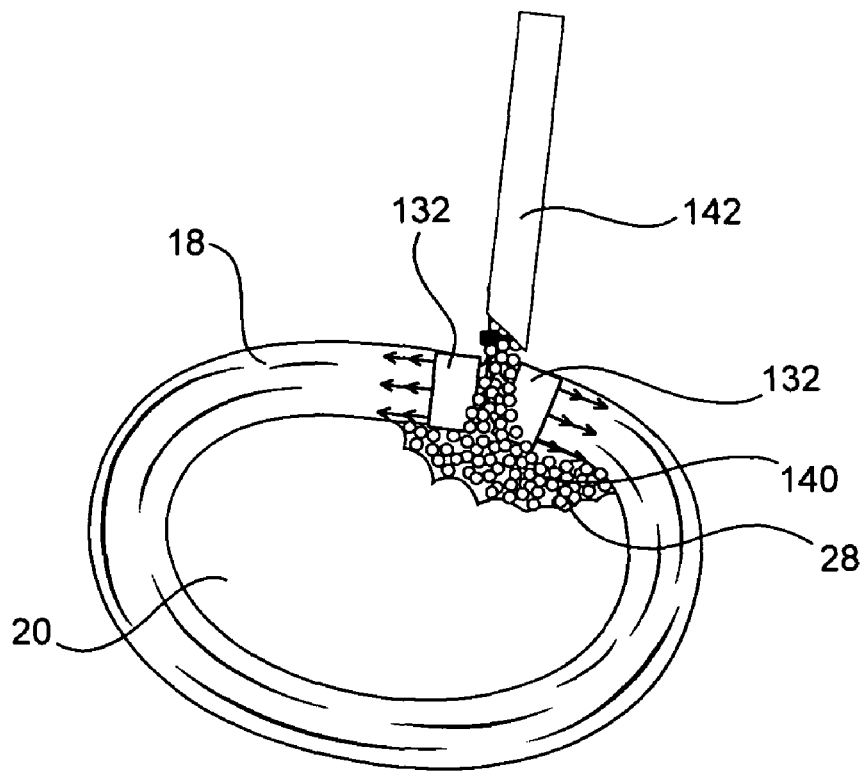
Figure 11E:
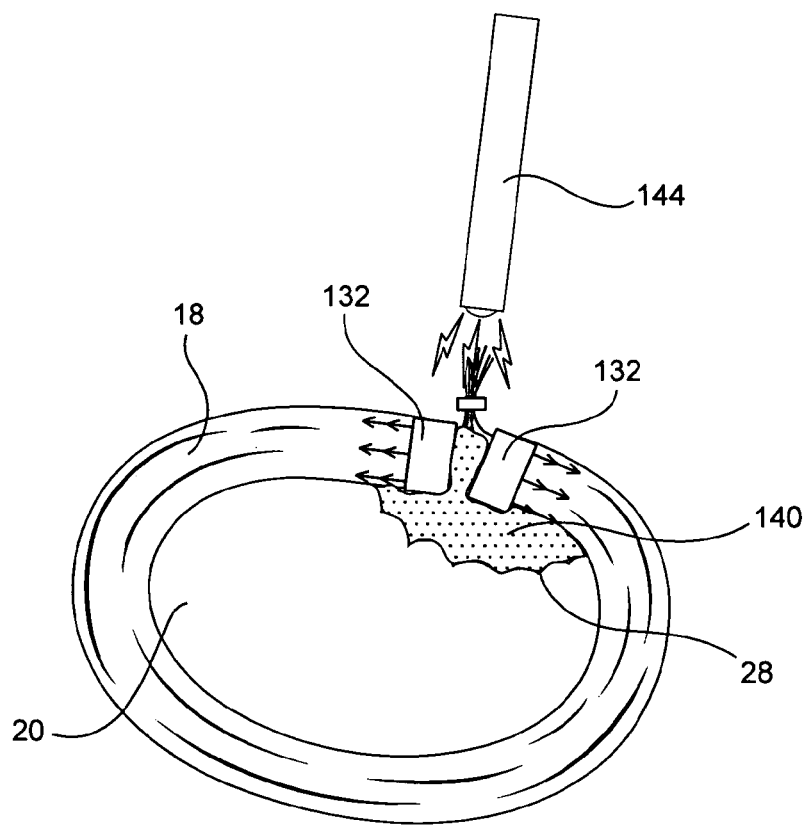

As illustrated in FIG. 11A, device 130 is implanted within an annulus 18 by way of penetrating or inserting anchors 134 parallel to the lamellar planes or layers, preferably such that each of anchors 134 is positioned within an intra-lamellar space. As such, the distal surface of endplate 132 contacts the cut or free end of annulus or free ends of the lamellae and is positioned transversely thereto. The insertion process is repeated with a second device 130 which is positioned within the opposing free end of annulus 18, as illustrated in FIG. 11B. Unlike the previously described embodiments, a single integrated component is implanted within each free end of annulus 18. Suture ends 136 are then synched together and secured to each other with tie or knot 138, as illustrated in FIG. 1C. A delivery tube 142 is then employed to deliver prosthetic material 140 over the scaffolding formed by the knotted sutures, as illustrated in FIG. 11D, where an amount of material is injected sufficient to fill defect 28 within nucleus 20 and annulus 18. Curing instrument 144 is then employed to cure prosthetic material 140, as illustrated in FIG. 11E.

Figure 12A:
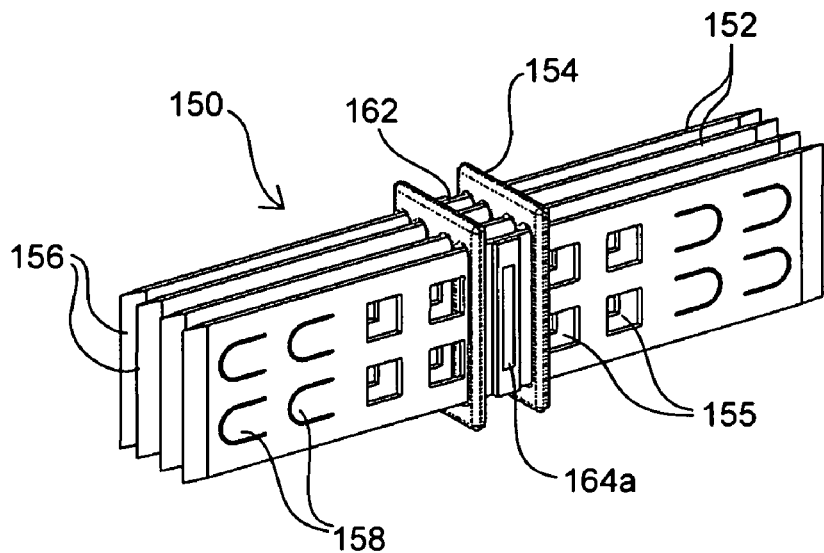
FIGS. 12A-12C illustrate perspective and top views of another disc augmentation device of the present invention in which a plurality of the devices of FIGS. 3A-3D are assembled into an integrated unit.
Figure 12B:
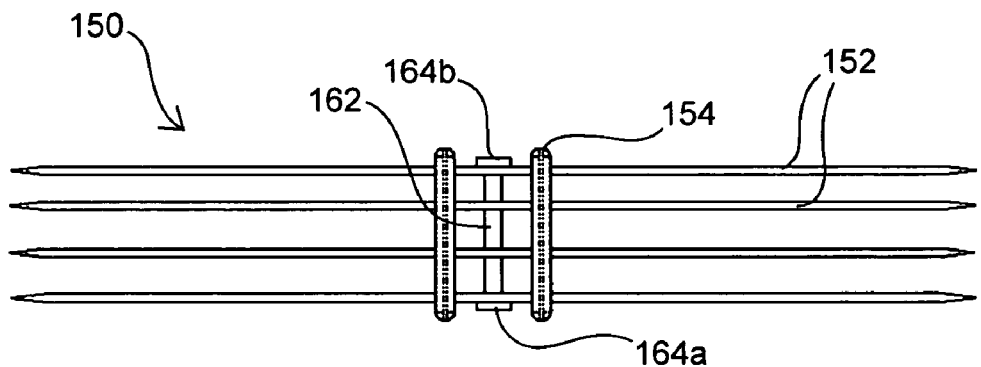
Figure 12C:
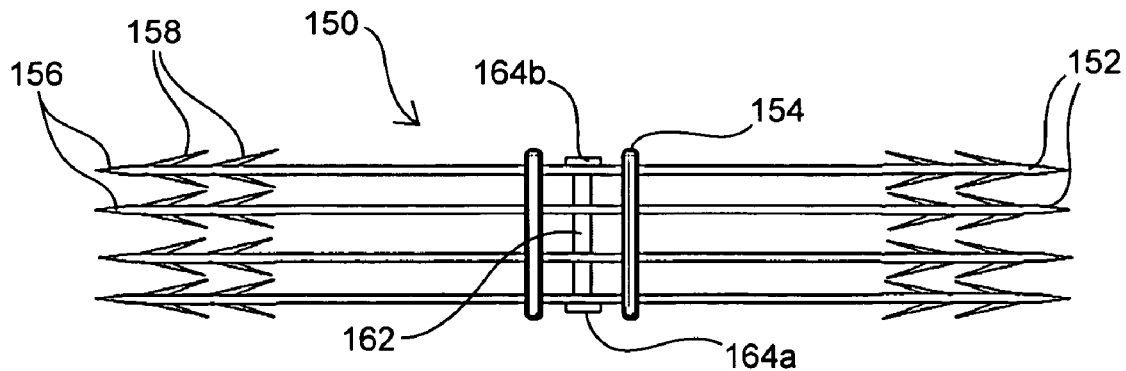

FIGS. 12A-12C illustrate another annular augmentation device 150 which is an integrated assembly of inter-lamellar components 152 which are similar to the implants 46 of FIGS. 3A-3D. Each component 152 has a planar structure sized and shaped to be positioned within an inter-lamellar space. Components 152 are bendable or foldable about a central portion having apertures 155. The end portions have anchors 158 which are flarable after implant, as illustrated on FIG. 12C. The distal ends 156 of component 152 may be tapered or have a sharp blade edge to facilitate separation and penetration of structure between adjacent lamellae. Slotted brackets 154 are positioned about the central portions of structures 152 to hold and maintain them in a substantially parallel, spaced relationship. A transverse member 162 positioned parallely between brackets 154 also extends centrally through structures 152 and is held thereto by proximal and distal hubs 164a, 164b where proximal hub 164a provides a slot for releasably receiving the distal end of an insertion tool 160, as illustrated in FIGS. 13A-13C.

Figure 13C:
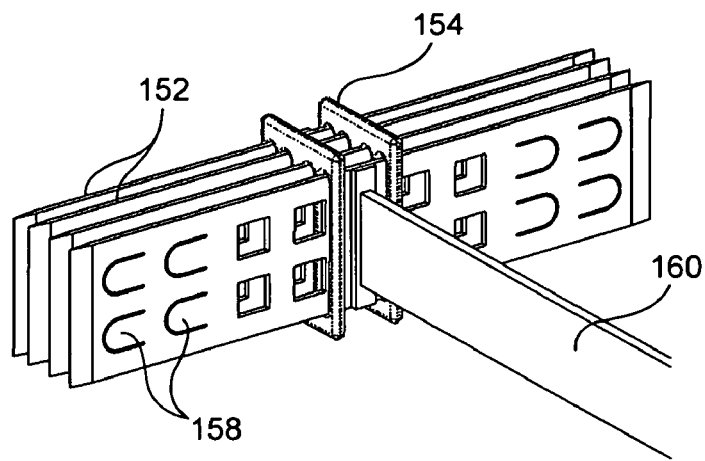
Figure 13C:
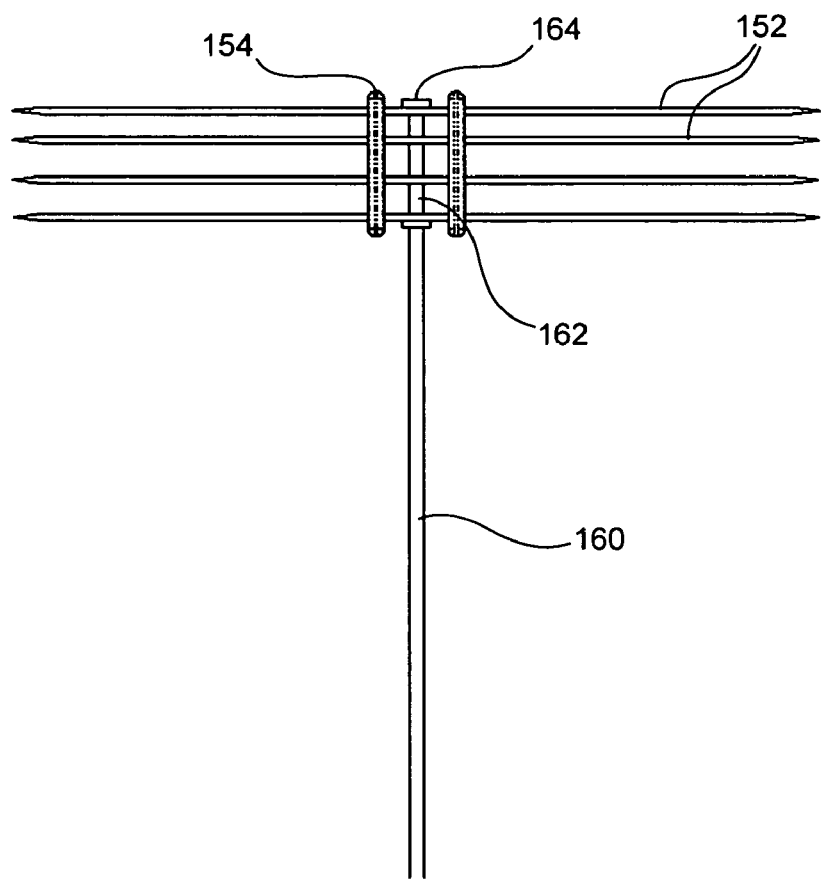
Figure 13D:
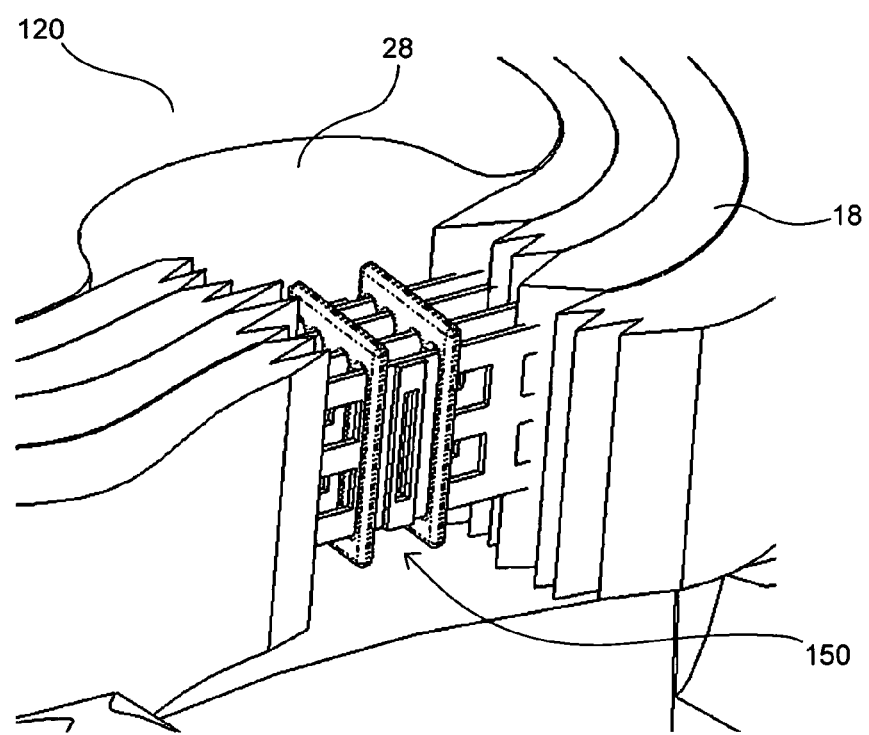

FIGS. FIGS. 13A-13D illustrate device 150 in various states of deployment where manipulation of insertion tool 160 selectively adjusts the profile of device 150. FIGS. 13A and 13A' illustrate device 150 in its lowest profile state in which the distal portion of structures 152 (i.e., the distal two structures) is folded distally and the proximal portion of structures 152 (i.e., the proximal two structures) is folded proximally to the maximum extent where only the tips 156 of the structures extend from the slots of brackets 154. In this configuration, device 150 is most easily positioned within a void within the annulus with or without the assistance of a delivery sheath or tube (not shown). After insertion into the annulus, insertion tool 160 is manipulated to compress the folded central portions toward each other and thereby cause the end portions of structures 152 extend radially outward, as illustrated in FIGS. 13B and 13B'. The compression structures 152 continues until they are fully straightened with their end portions fully embedded within the intra-annular spaces, as illustrated in FIGS. 13C and 13C'. At this point, insertion tool 160 is released from transverse member 162 which remains implanted with device 150, as illustrated in FIG. 13D. As with the other embodiments described above, a prosthetic material may then be delivered through implanted device 150 to within void 28 and cured.

Figure 14A:
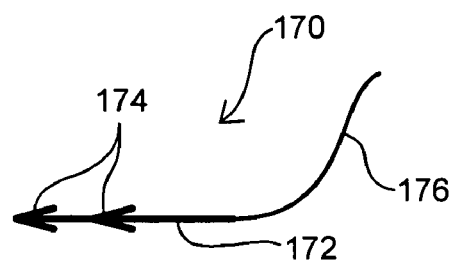
FIGS. 14A and 14B illustrate another disc augmentation implant of the present invention.
Figure 15A:
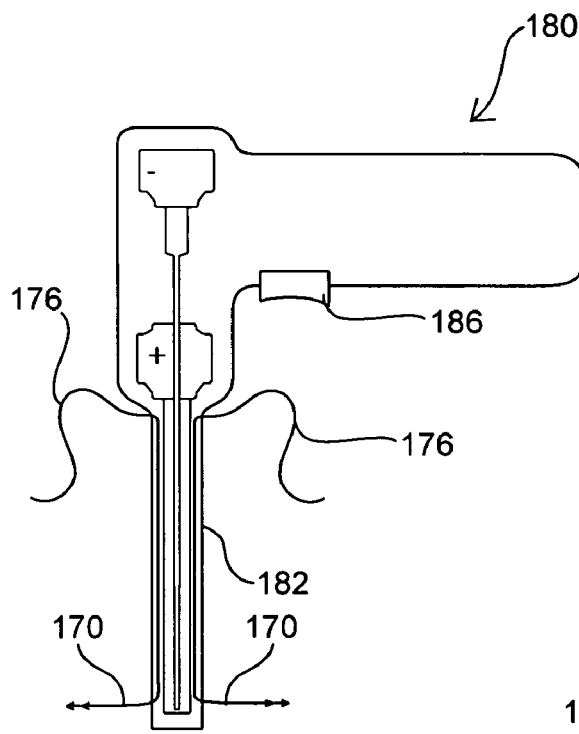
FIGS. 15A and 15B illustrate an instrument for delivering and implanting the implant of FIGS. 14A and 14B.
Figure 15B:
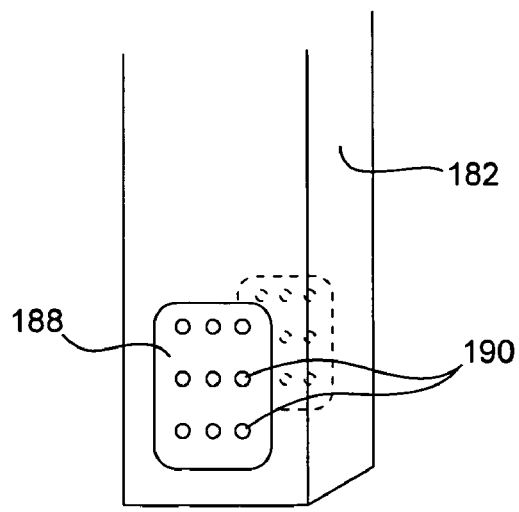

FIGS. 14A and 15B illustrate another variation of an implantable annular augmentation device 170. Here, device 170 is a standalone elongated anchor 172 having flarable barbs 174 (shown in undeployed and deployed conditions, respectively) at a distal or leading end and a suture, filament or wire 176 at a proximal or trailing end. A plurality of such devices 170, including at least one device for implantation on each side of an annular defect, either within an inter-lamellar space or within the nucleus or healthy portion of the annulus, is employed to provide a scaffolding structure which augments the annulus but may also serve to support implantable prosthetic materials.

FIGS. 15A and 15B illustrate a delivery device 180 for the simultaneous delivery and deployment of a plurality of anchors 170 to within an annulus. Delivery device 180 includes a shaft portion 182 which houses a plurality of pre-loaded implantable devices 170. Delivery device 180 is configured to automatically fire a plurality of devices 170 laterally outward from opposing sides 188 of shaft 182, as illustrated in FIG. 15B. One or more anchors 170 are aligned with or channeled to exit ports 190 provided at the laterally facing surfaces 188 of distal end such that the anchors are caused to be deployed within intra-annular locations in an array fashion. Delivery device 180 may be sized and configured to deploy any number of anchors 170 simultaneously on one or both sides of shaft 182.

Figure 16A:
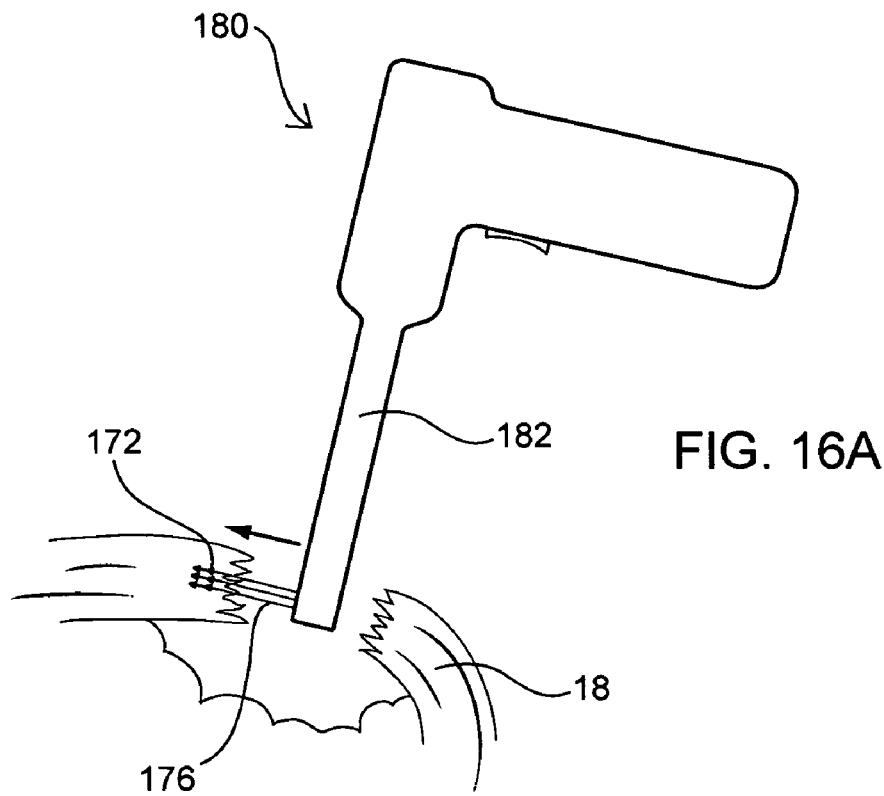
FIGS. 16A-16F illustrate various states of deployment of the device of FIGS. 14A and 14B.
Figure 16B:
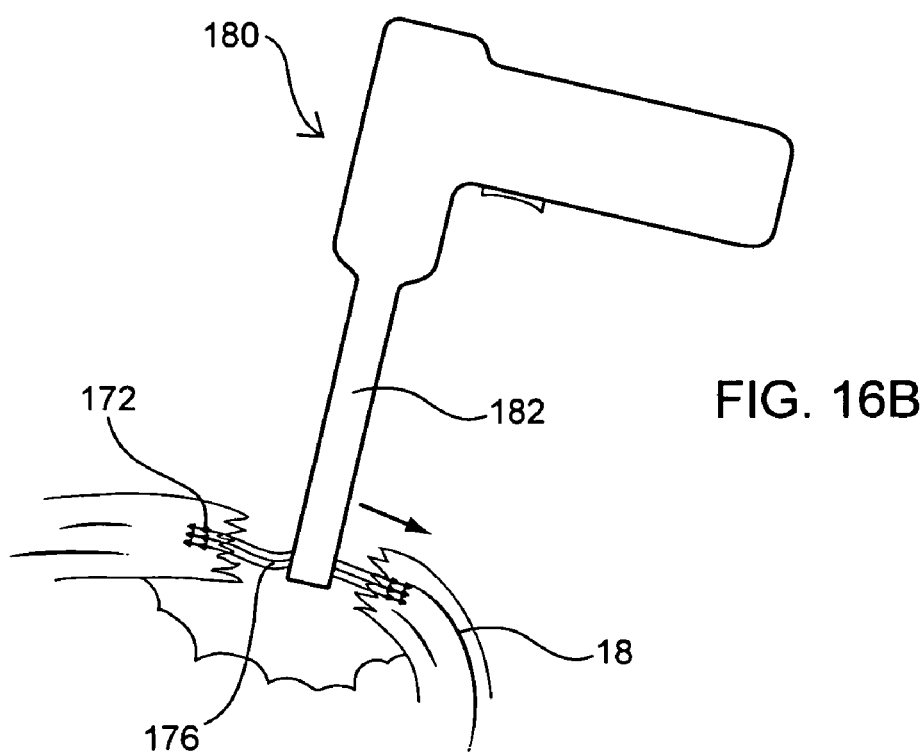
Figure 16C:
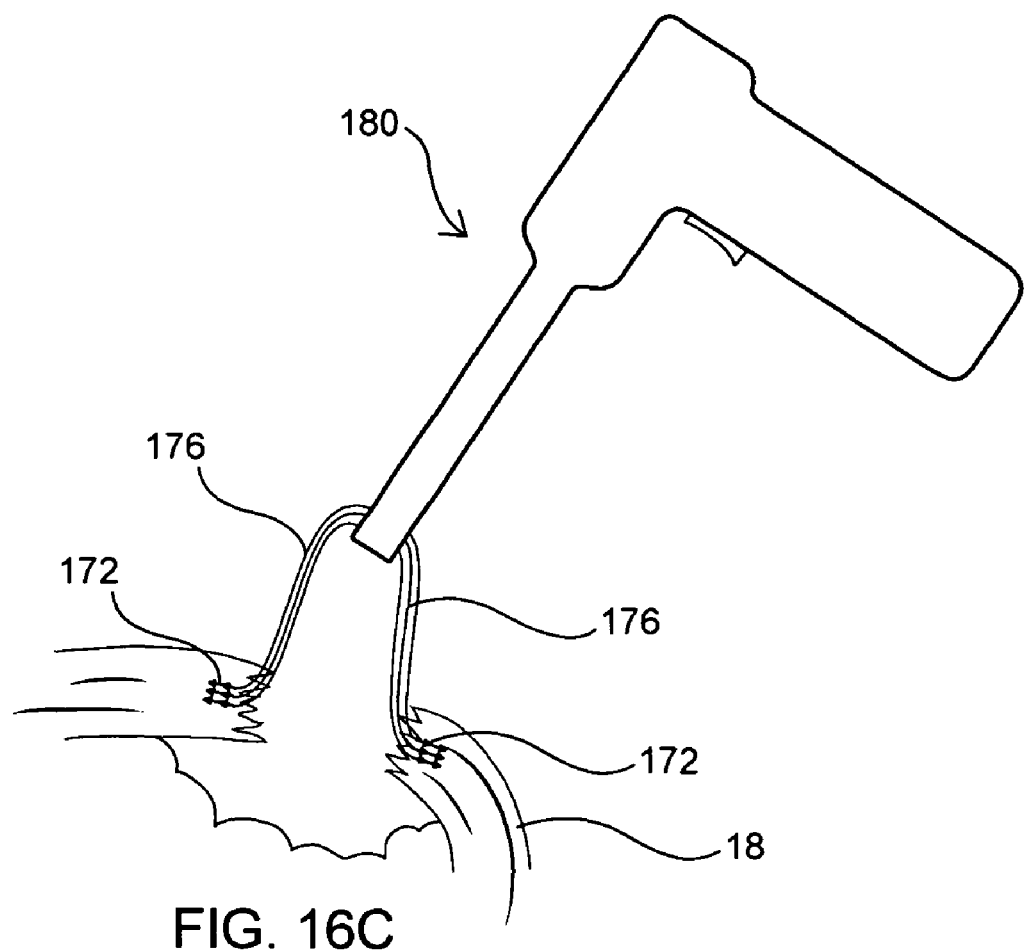
Figure 16D:
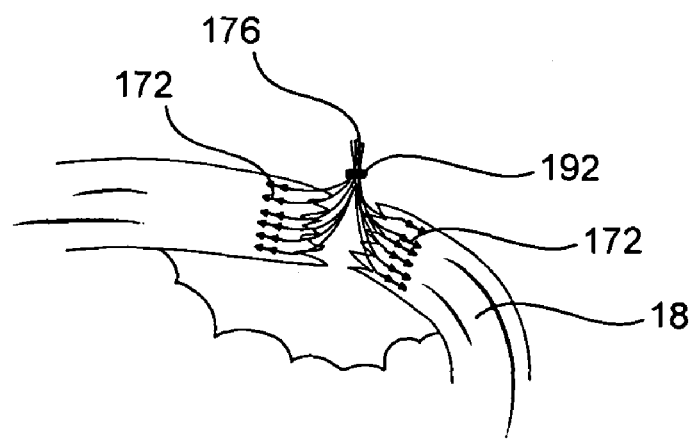
Figure 16E:
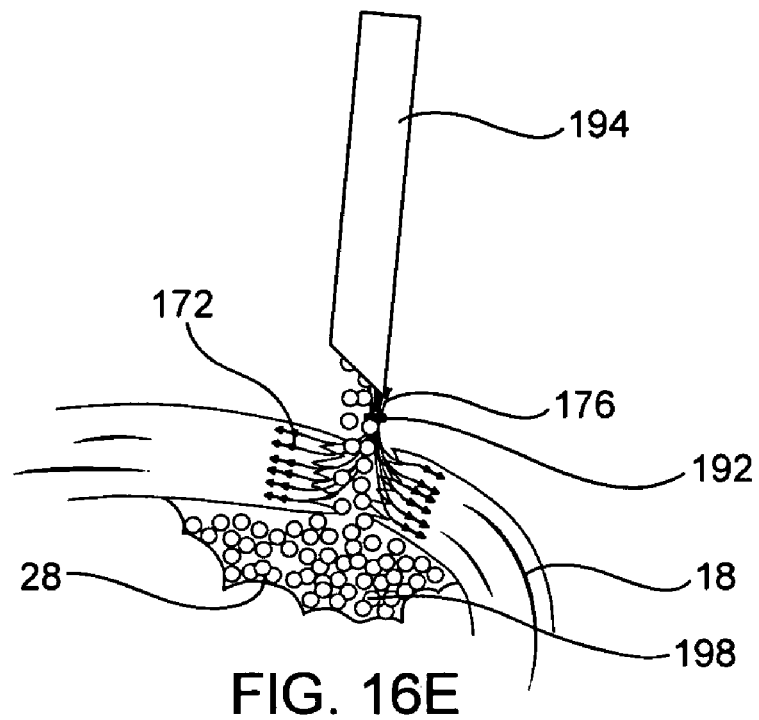
Figure 16F:
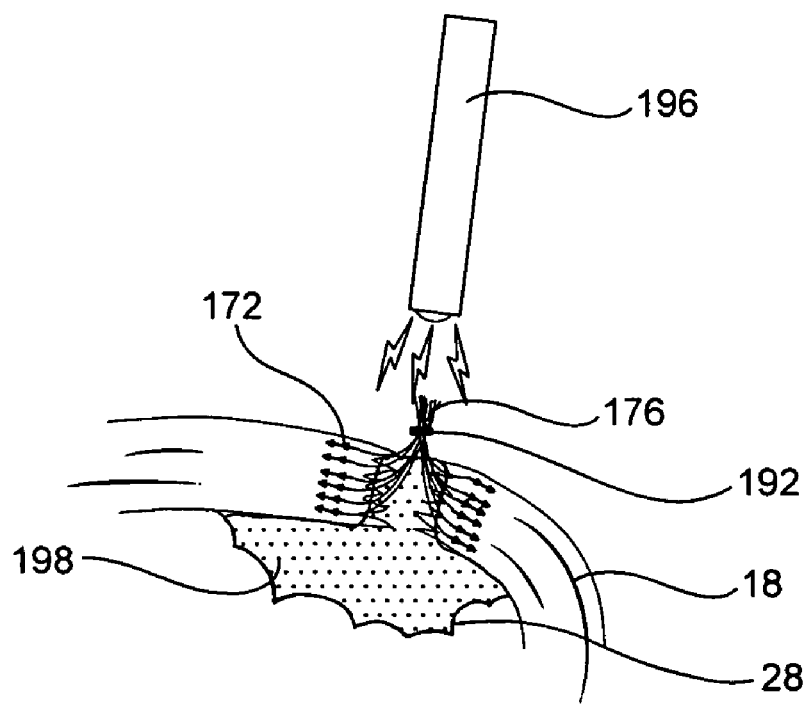

For example, FIGS. 16A and 16B illustrate use of delivery device 180 where a plurality of anchors 172 is deployed into one side or cut end of annulus 18 at a time. After anchors 170 have been delivered into both ends of annulus 18, the trailing suture ends 176 are synched together, as illustrated in FIG. 16C, and securely tied by a knot or other clip means 192, as illustrated in FIG. 16D. Prosthetic material 198 is then injected by injection tube 194 through the webbing defined by knotted strings 176 to fill void 28 within nucleus 20 and annulus 18, as illustrated in FIG. 16E. The prosthetic material 198 is then cured by exposure to UV light by way of UV light emitter 196, as illustrated in FIG. 16F.

Figure 14B:
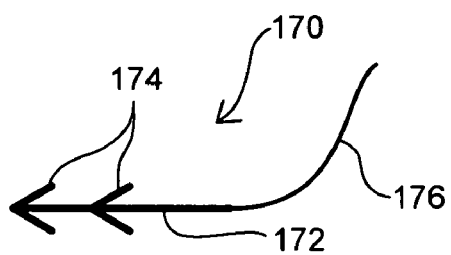
Figure 17:
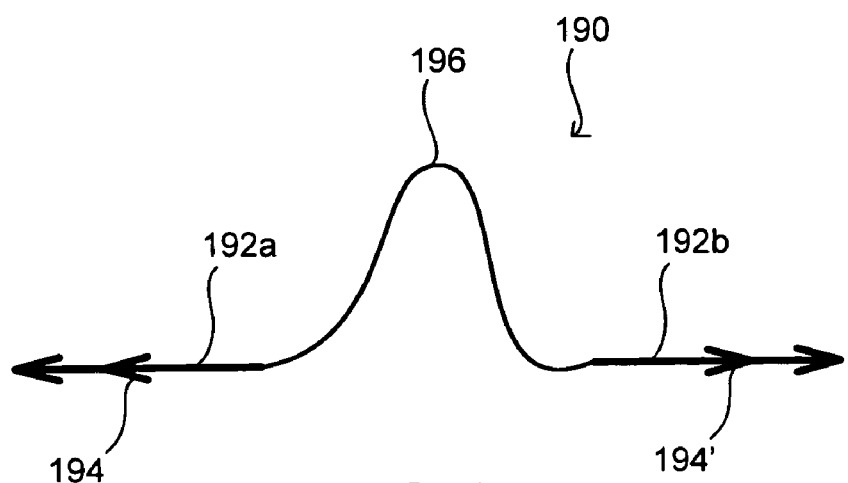
FIG. 17 illustrates another disc augmentation device of the present invention which is usable with a plurality of such devices.

FIG. 17 illustrates another variation of an implantable annular augmentation device 190. In essence, device 190 is an integration of two of the above-described devices 170 of FIGS. 14A and 14B. Device 190 includes two elongated anchors 192a, 192b having flarable barbs 194 (shown in an undeployed condition) and bridged together by a suture, filament or wire 196 at proximal ends of the anchors. The length of suture 196 is selected such that when opposing anchors 192a, 192b are embedded within tissue, the suture is at least somewhat taught and able to apply tension on the tissue. As such, when a device 190, but more frequently a plurality of such devices 190, is implanted within an inter-lamellar space or within the nucleus or healthy portion of the annulus, a scaffolding structure is established which augments the annulus but may also serve to support implantable prosthetic materials.

Figure 18:
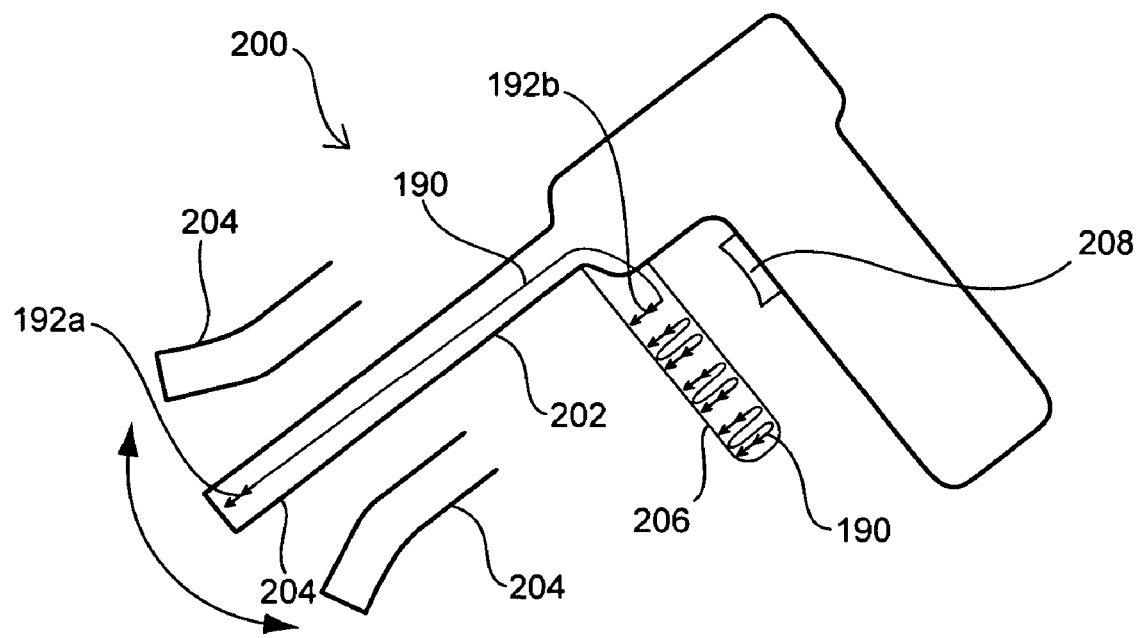
FIG. 18 illustrates an instrument for delivering and implanting the device of FIG. 17.
Figure 19A:
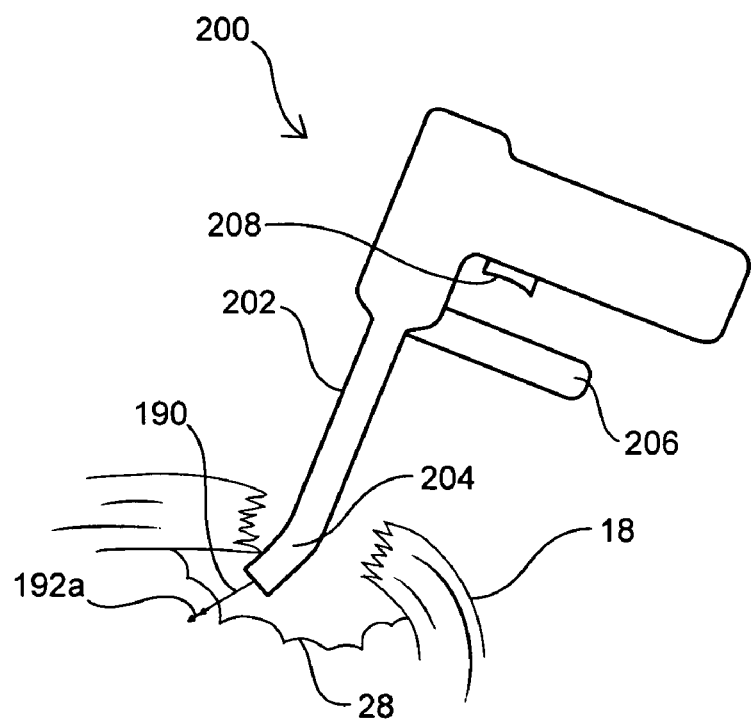
FIGS. 19A-19F illustrate various steps for implanting the disc augmentation device of FIG. 17 utilizing the instrument of FIG. 18 and for implanting a prosthetic material according to methods of present invention.
Figure 19B:
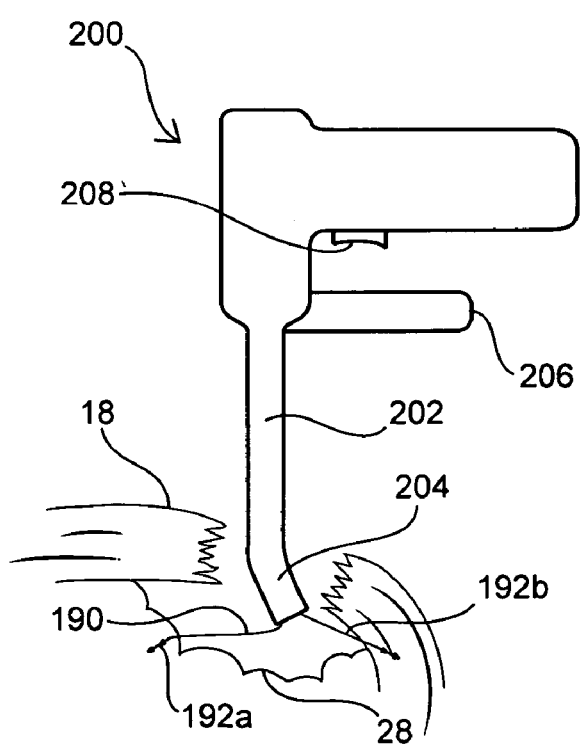
Figure 19C:
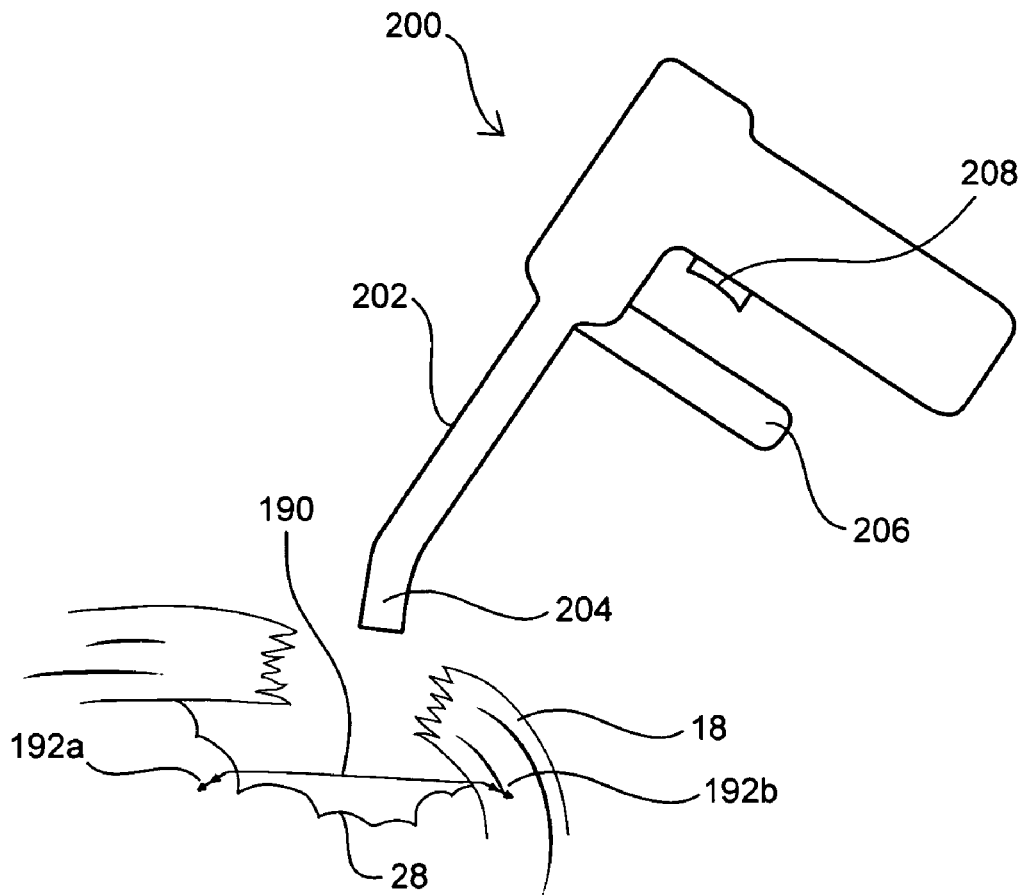
Figure 19D:
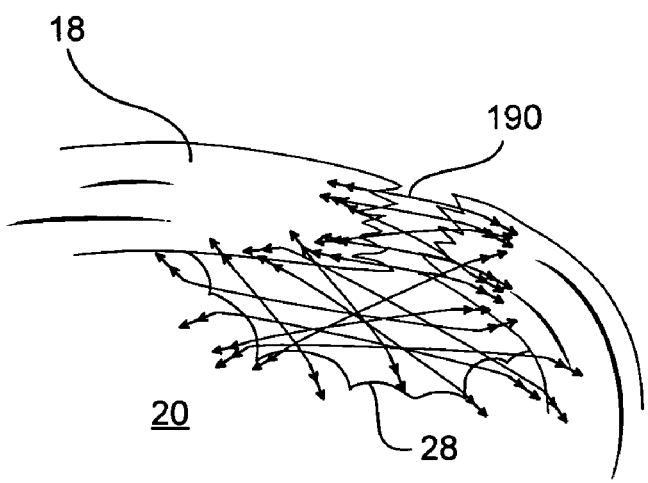
Figure 19E:
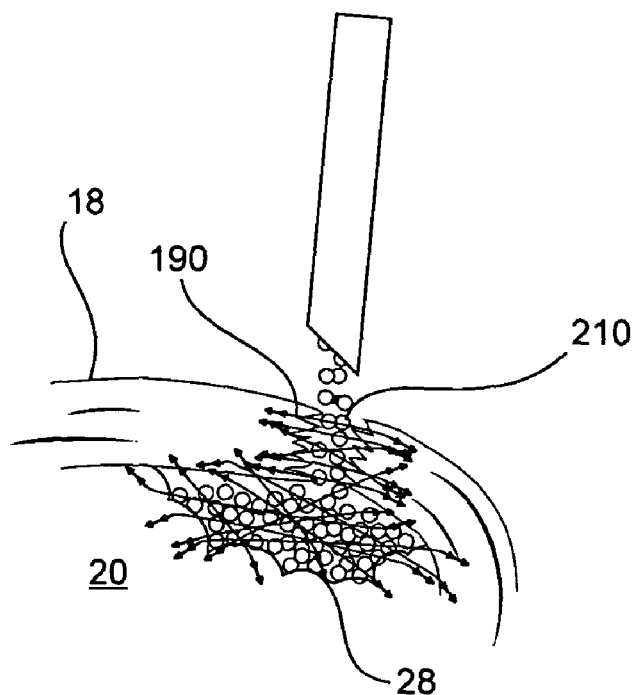
Figure 19F:
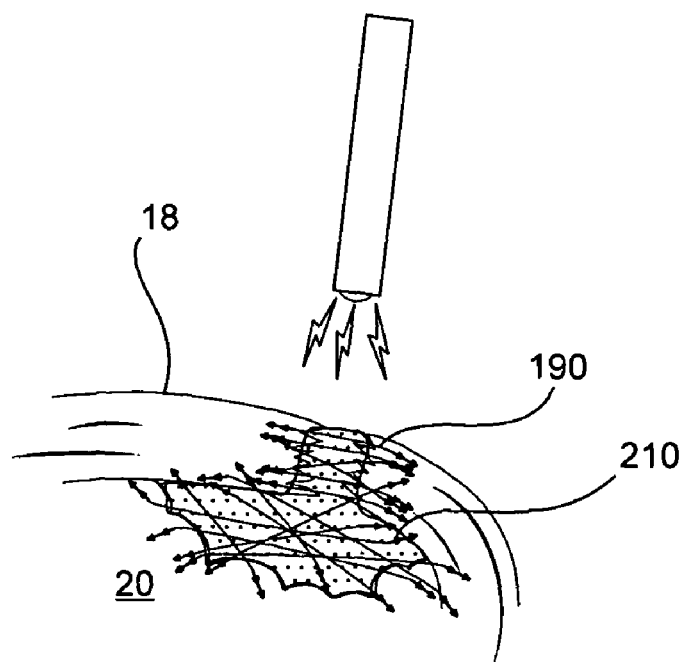

FIG. 18 illustrates a device 200 for the automated delivery of one or more devices 190. Delivery device 200 has a shaft 202 having an articulating distal end 204 which is insertable into and moveable within a defect 28. Delivery device 200 may be further equipped with a scope that facilitates visualization of the target implantation area. A plurality of devices 190 is shown preloaded within a cartridge 206 which is engaged with device 200. By activation of a trigger mechanism 208, the preloaded devices 190 are individually transferred to shaft 202 and delivered to the implantation site where leading or first anchor 192a is implanted in a first location within or adjacent to defect 28 (shown within the defect itself), as shown in FIG. 19A. The trailing or second anchor 192b is then also deployed within or adjacent to defect 28 (shown within an anterior portion of the annulus) at a distance from the first anchor 192a to create some tension between the two, as illustrated in FIGS. 19B and 19C. Any number of devices 190 may be implanted to create the necessary scaffolding structure within defect 28 and/or across a void within the annulus 18, as illustrated in FIG. 19D. After the scaffolding structure is complete, a prosthetic material 210 may be injected into void 28 through the scaffolding formed by devices 190 and subsequently cured, as illustrated in FIGS. 19E and 19F, respectively.

Figure 20A:
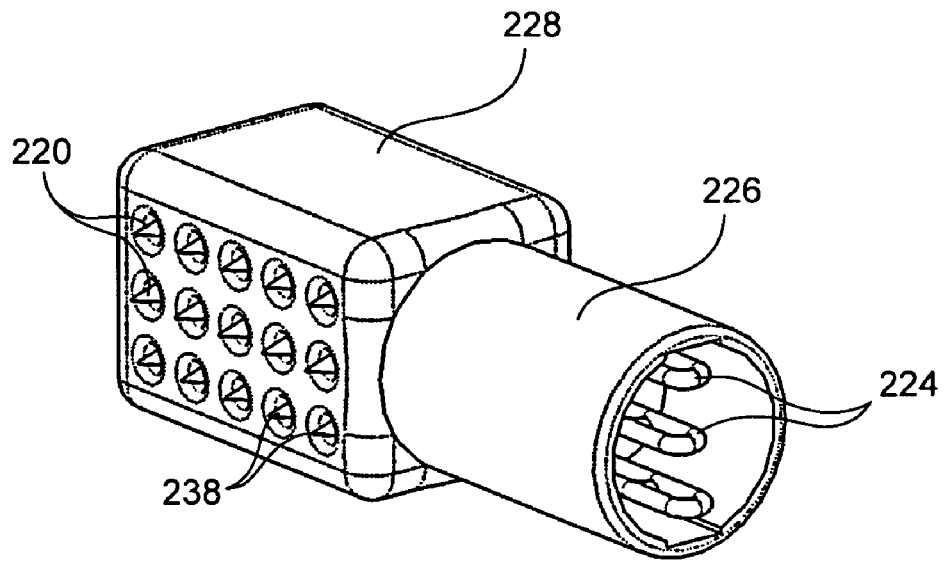
FIGS. 20A and 20B illustrate another disc augmentation device of the present invention provided in an assembled plurality and operatively loaded within the distal end of a delivery device of the present invention.
Figure 20B:
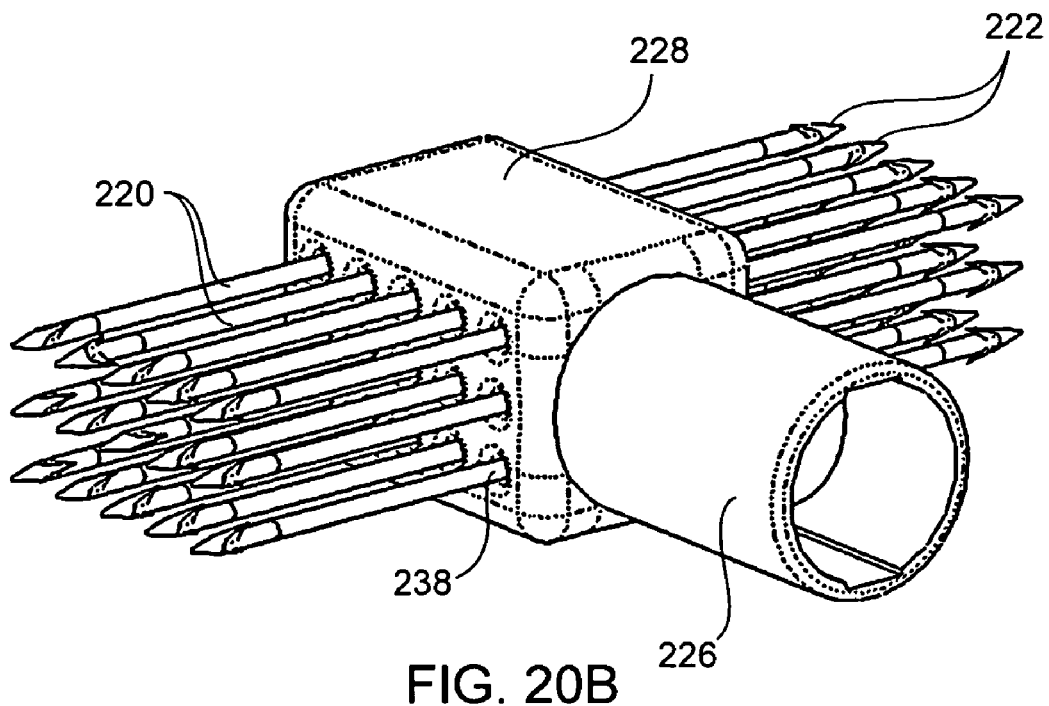
Figure 21A:
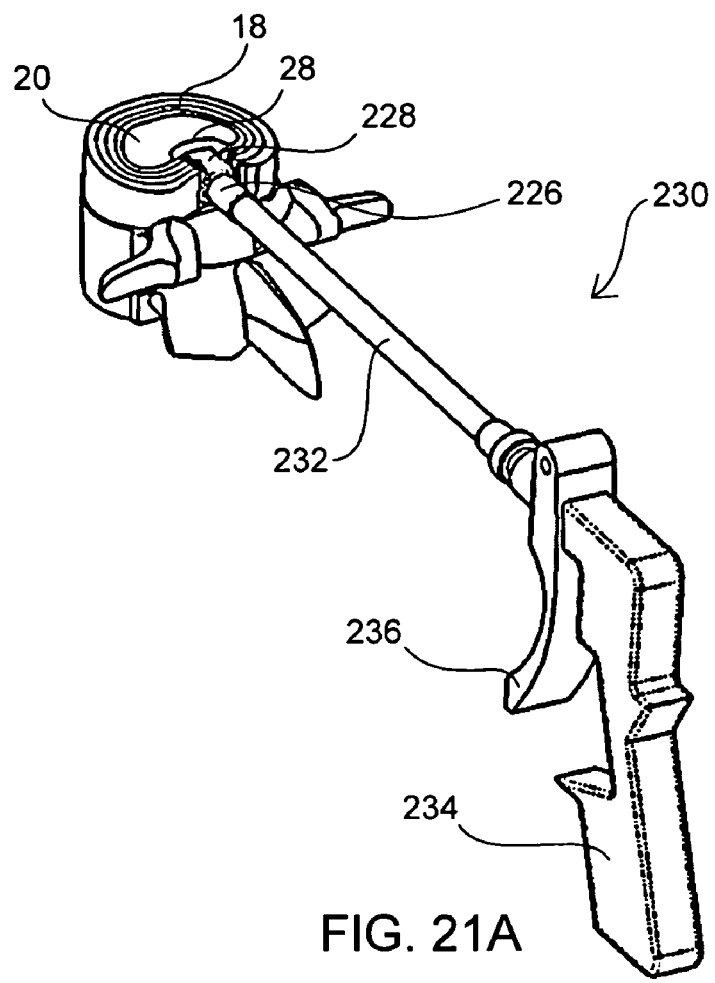
FIGS. 21A-21H illustrate various steps for implanting the disc augmentation devices of FIGS. 20A and 20B and for implanting a prosthetic material according to methods of the present invention.
Figure 21B:
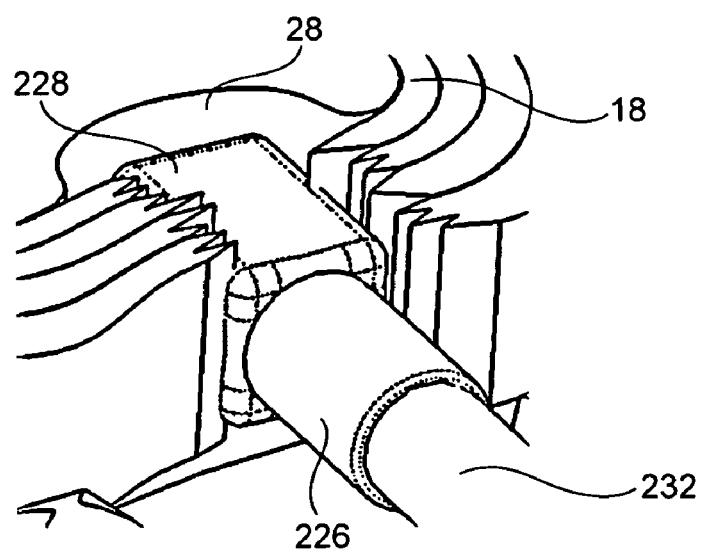
Figure 21C:
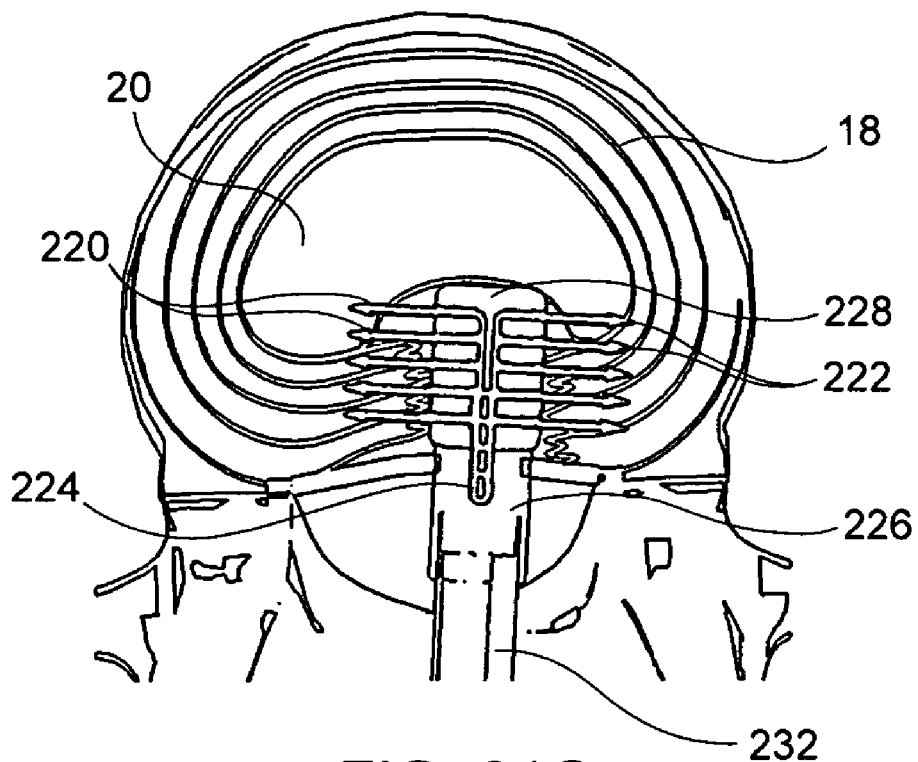
Figure 21D:
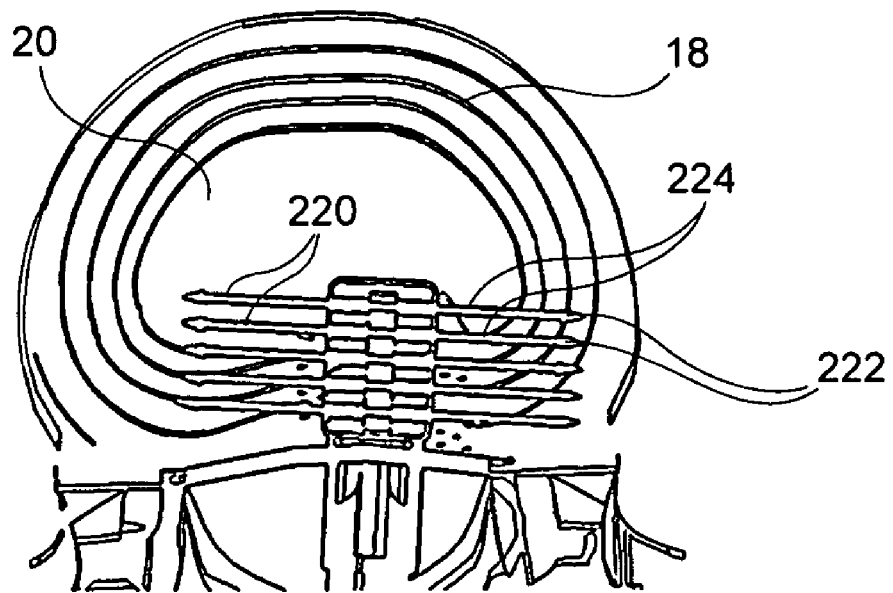
Figure 21E:
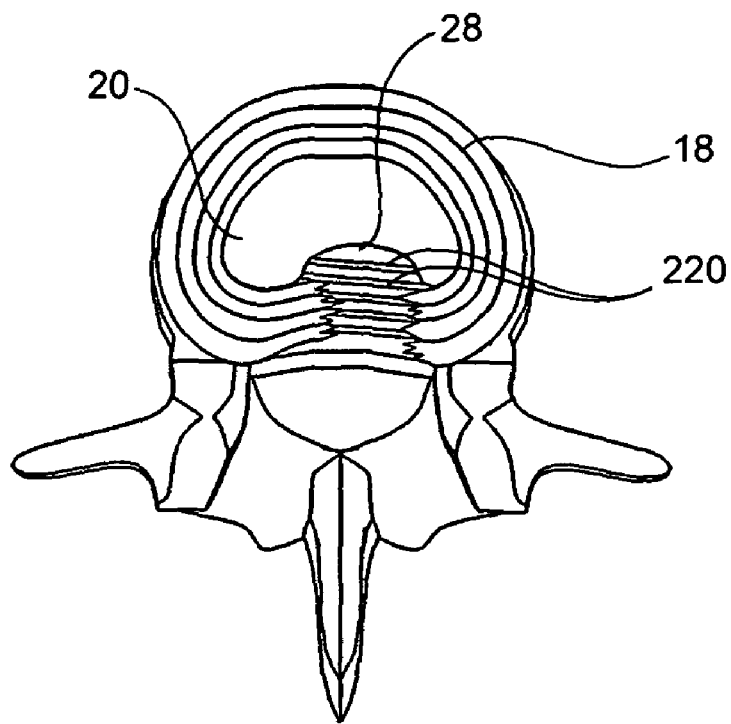
Figure 21F:
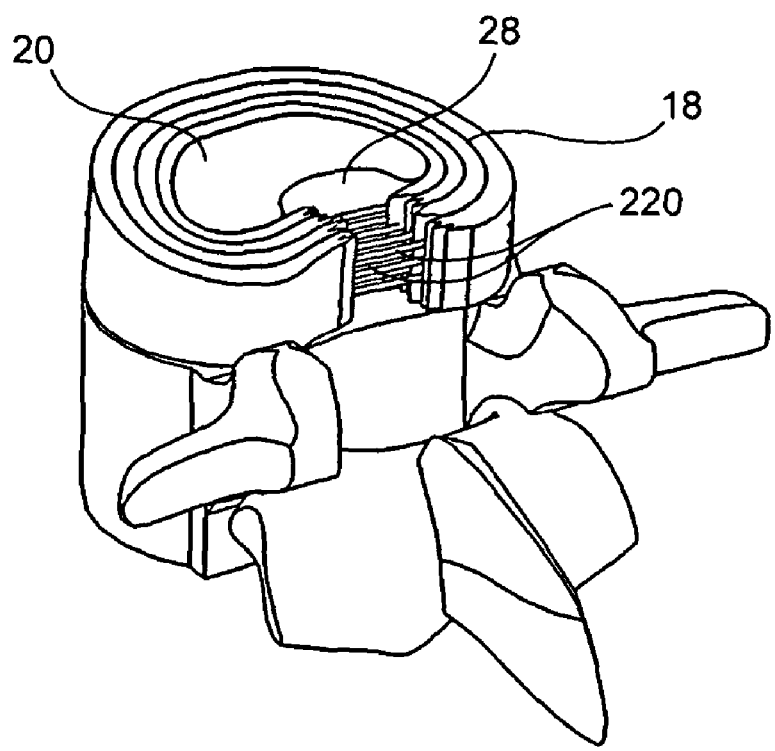

FIGS. 20A and 20B provide perspective views of an disc augmentation assembly of doubled-ended pins or needles 220 loaded within the distal end 228 of a delivery tool 230 (see FIG. 21A). Pins 220 have barbed ends 222 and are preferably made of a superelastic material to allow them to be folded or flexed about a central portion 224 for loading into tool 230 and to provide a low profile, illustrated in FIG. 20A, during delivery of the loaded tool to the implant site. Delivery tool 230, shown in full in FIG. 21A, provides a narrow shaft 232 for further facilitating minimally invasive delivery through an access site to the disc to be treated. Upon delivery, distal end 228 with pins 220 in their low profile or folded state is positioned within the annulus defect 28. Upon optimizing the position of distal end 228, a trigger mechanism 236 on handle 234 of tool 230 is actuated, causing central portions 224 of pins 220 to be pushed or advanced distally until fully straightened, whereby pin ends 222 are caused to extrude from apertures 238 on the lateral sides of distal end 228 (see FIGS. 20B, 21C and 21D). When fully extended and deployed, the pins are released from the distal end of the delivery tool through slots (not shown) on the distally facing surface, and left behind to form a scaffolding which bridges at least a portion of the defect region 28, including at least a portion of a void within the annulus 18 and/or within the nucleus, as illustrated in FIGS. 21E and 21F.

Figure 21G:
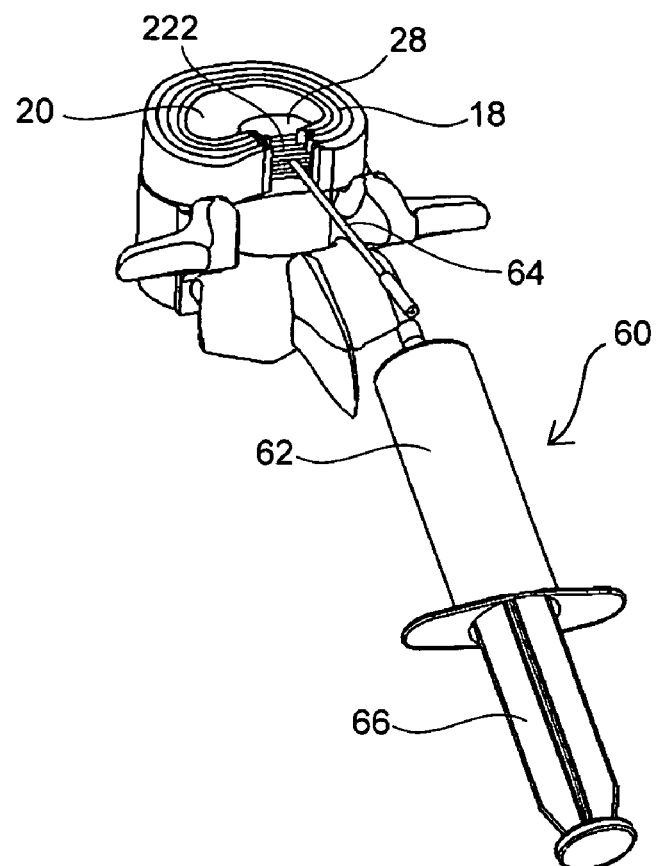
Figure 21H:
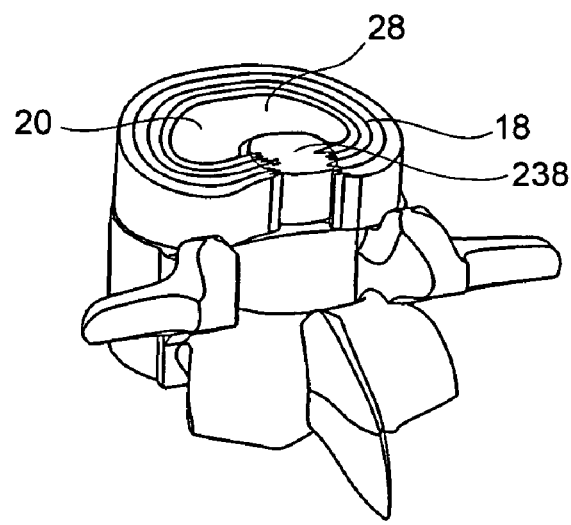

In a manner similar to that described above with respect to FIGS. 4F and 4G, an injector device 60 is then used to inject or extrude prosthetic material within void 28, as illustrated in FIG. 7C. In one embodiment, an injector device 60, as illustrated in FIG. 4F, having a syringe 62 containing an amount of the prosthetic material is coupled to a tube 64 which is sized to fit through the minimally invasive access site, as illustrated in FIG. 21G. The distal end of the tube 64 is positioned between pins 222, and plunger 66 is advanced to extrude a sufficient amount of the prosthetic material 238 to fill the portion of disc void 28 within nucleus 20 as well as within the spaces between pins 222. Upon filling the entirety of the void 28, or intermittently throughout the injection process, as shown in FIG. 21H, the injected material 68 may be allowed to cure or be actively cured, if such is necessary, as described generally above, to provide a plug or the like that extends from the nucleus 20 to the outer aspect of the annulus 18.

Figure 22A:
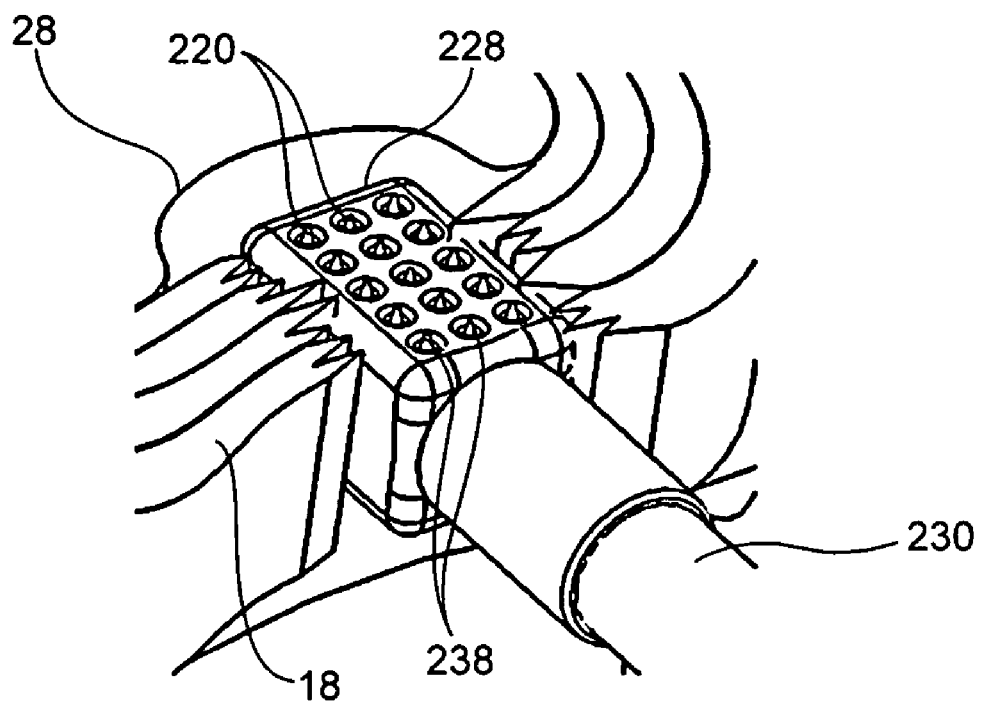
FIGS. 22A and 22B illustrate the assembled plurality of devices of FIGS. 20A and 20B operatively loaded in the delivery device but configured and positioned for implantation of its ends within adjacent intervertebral endplates.
Figure 22B:
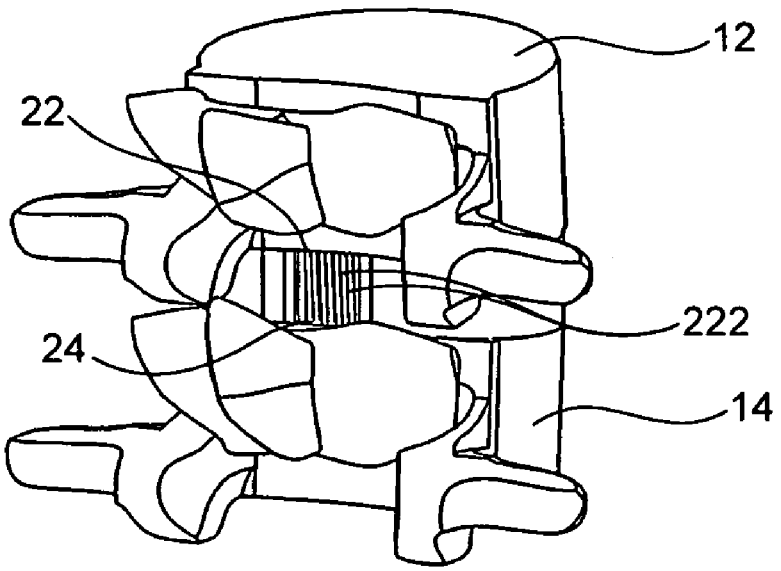

FIGS. 22A and 22B illustrate another assembled plurality of pins 222 operatively loaded within distal end 228 of delivery tool 230, as discussed above, but alternately positioned within defect 28. Specifically, distal end 228 is rotationally oriented 90% from the operative deployment position discussed above (see FIG. 21B) where pin apertures 238 are facing opposing intervertebral endplates 22, 24 rather than the free ends of annulus 18. The pin delivery, deployment and release steps described above are similar here, but pins 222 are anchored within the intervertebral bodies thereby providing a scaffolding having vertically or transversely placed pins rather than horizontally placed pins.

Figure 23:
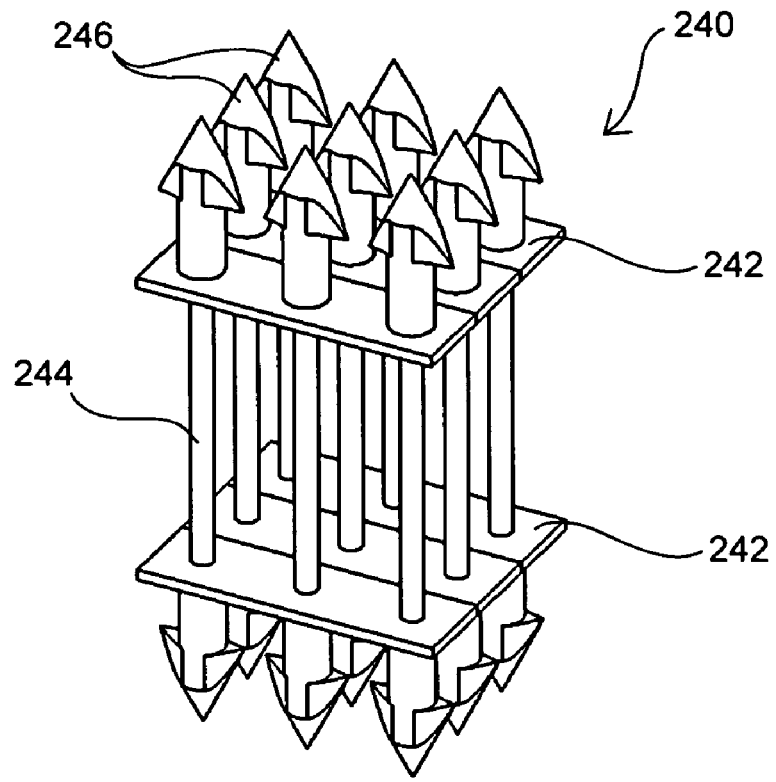
FIG. 23 illustrates another augmentation device including assembly of pin members.

FIG. 23 provides another augmentation device 240 configured for anchoring into the intervertebral endplates. Device 240, shown in a fully expanded condition, includes an assembly of parallel spaced pins 244 extending between and through brackets 242. The ends of each pin 244 are capped with a barbed head 246 which is slidable distally along pin 244 to a maximally extended and locked position. Alternatively, pins 244 are made of a stretchable material with barbed caps 246 fixed to the ends thereof to allow extension of the device to span a defect within an annular space.

Figure 24:
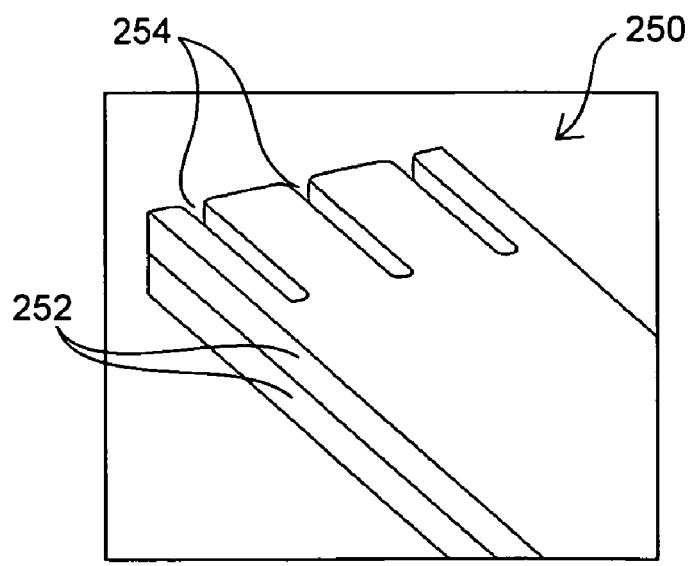
FIG. 24 is a perspective view of the distal end of a delivery tool usable to deliver and implant the device of FIG. 23.
Figure 25A:
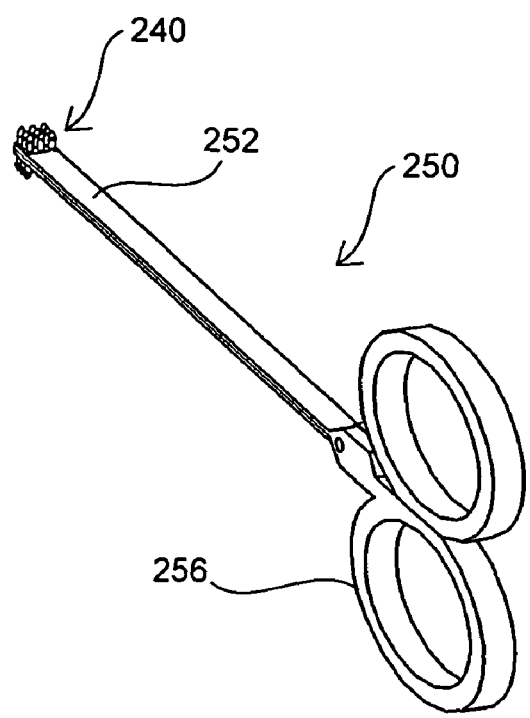
FIGS. 25A and 25B illustrate the device of FIG. 23 operatively loaded in the distal end of the delivery tool of FIG. 24.
Figure 25B:
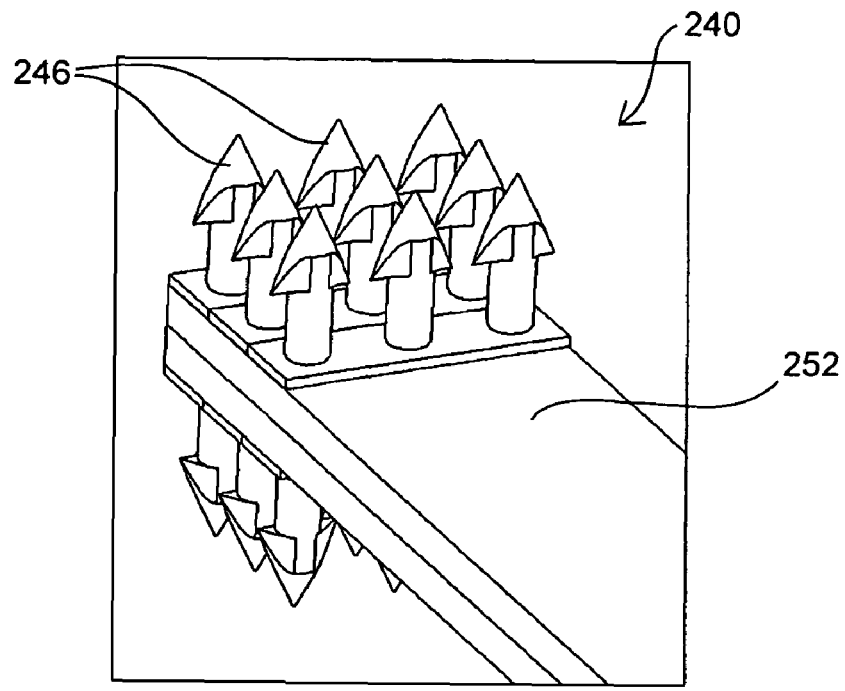

FIG. 24 illustrates the distal end of a delivery tool 250 having opposing plates 252 which are movable in a pivoting or scissor fashion with respect to each other. A number of slots 254 extend through the distal tips of plates 252 for receiving the assembly of pins 240 of FIG. 23 in a transverse fashion, as illustrated in FIGS. 25A and 25B. In this loaded position, caps 246 are in their retracted position on pins 244 or, in the alternate embodiment, pins 244 are in their unstretched state.

Figure 26A:
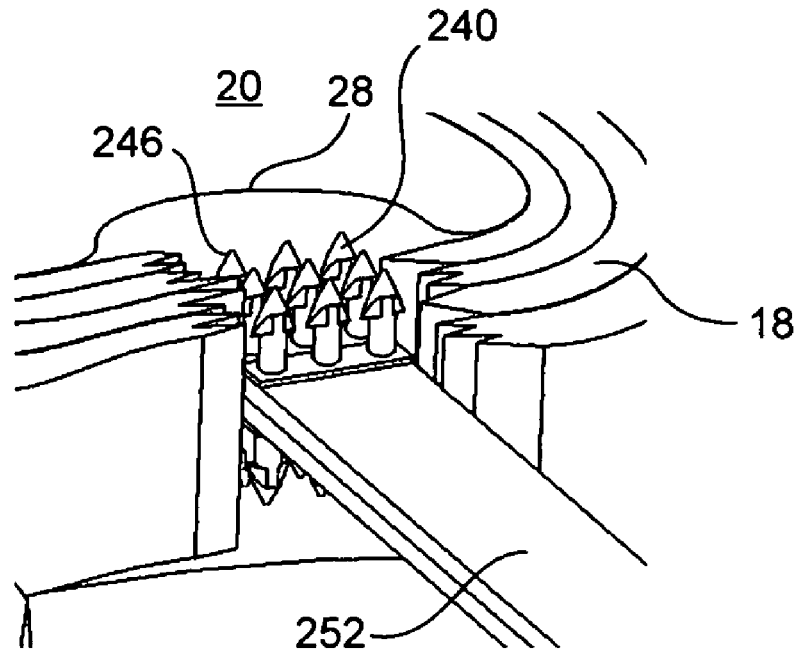
FIGS. 26A-26F illustrate various steps for implanting the disc augmentation device of FIG. 23 utilizing the delivery tool of FIG. 24 and for implanting a prosthetic material according to methods of the present invention.
Figure 26B:
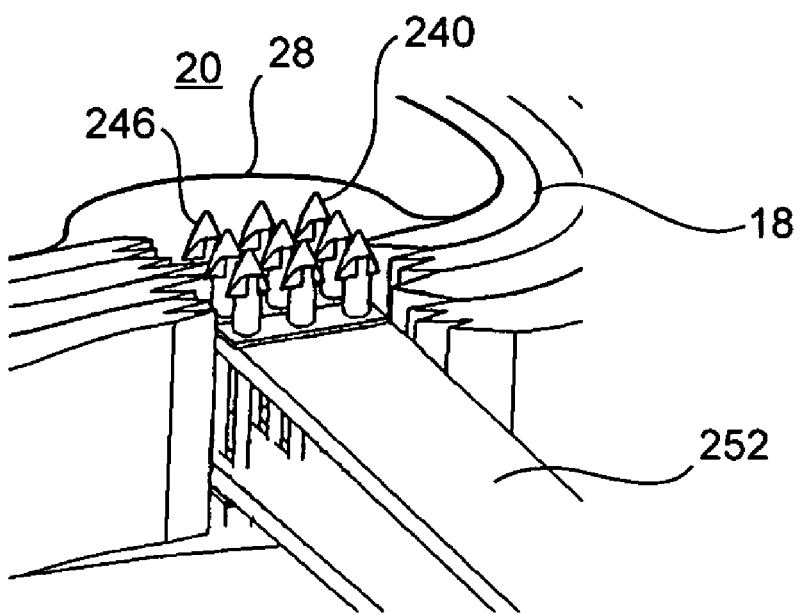
Figure 26C:
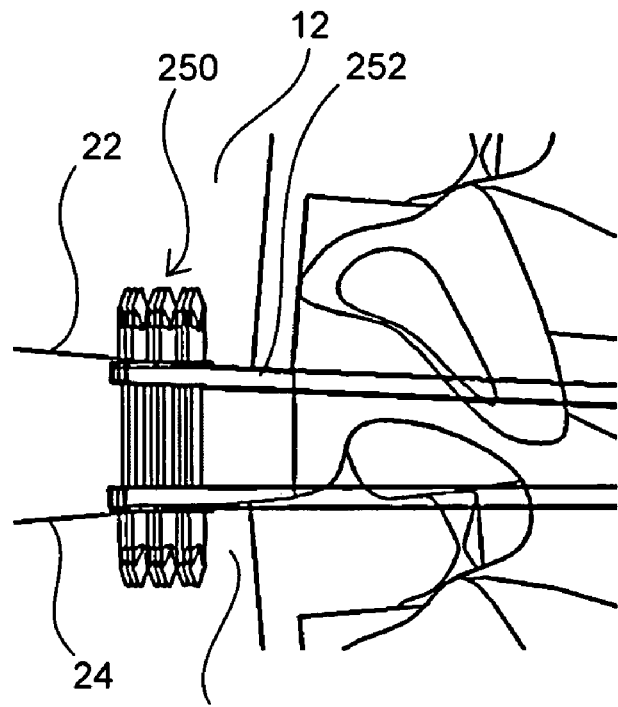
Figure 26D:
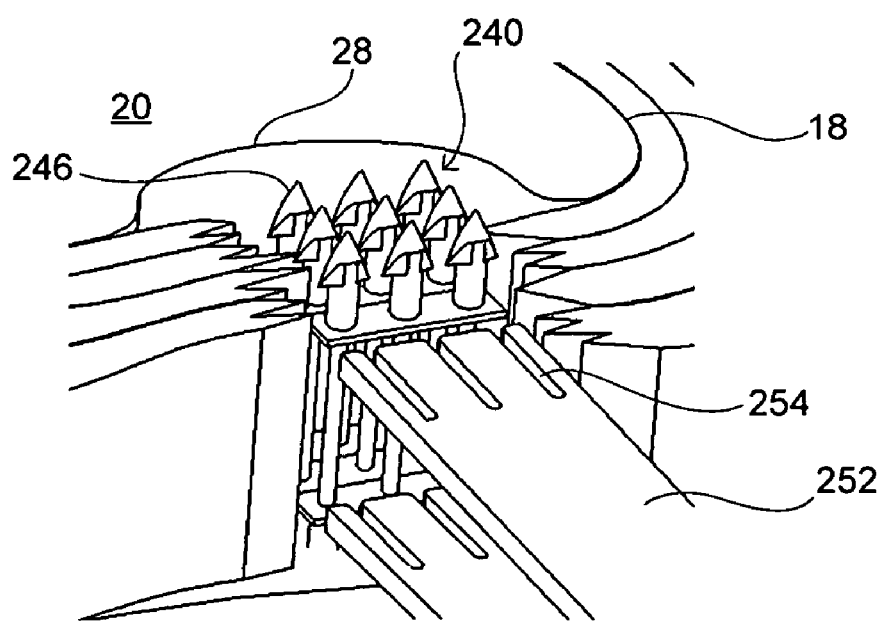
Figure 26E:
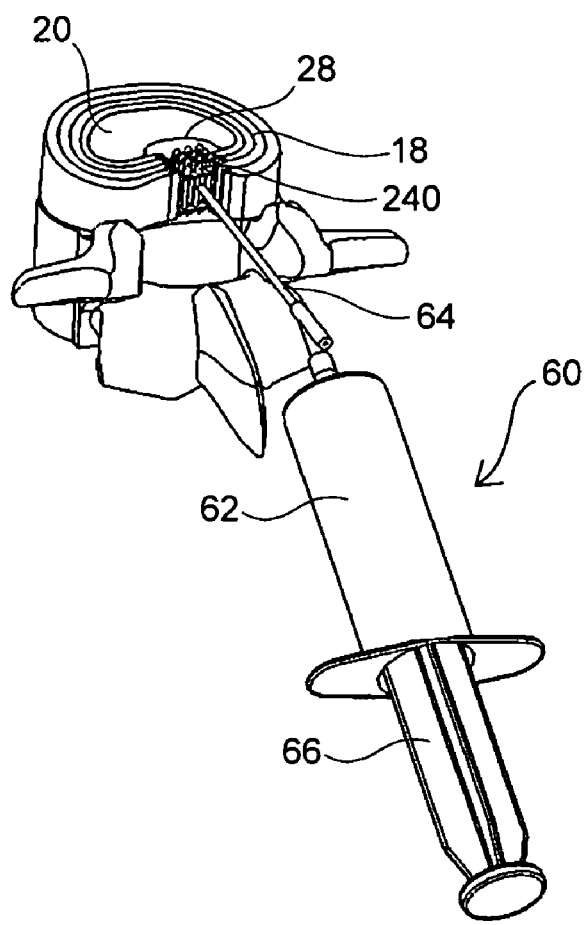
Figure 26F:
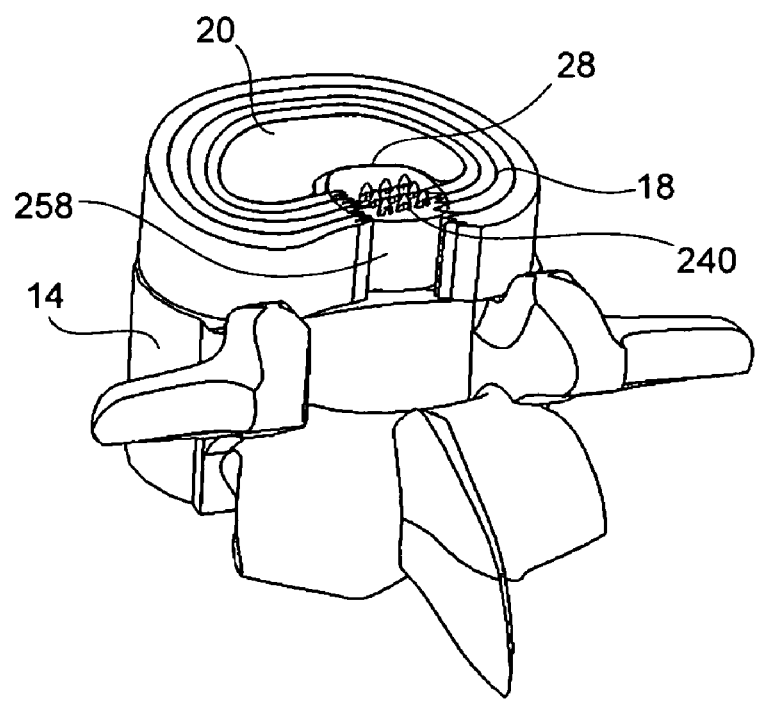

FIGS. 26A-26F illustrate various steps of implanting device 240 by means of delivery tool 250. Initially, tool 250 is delivered to the implant site within annulus 18 with plates 252 in their closed position so as to maintain device 240 in an unextended or undeployed state. Upon proper positioning at the implant site, plates 252 are opened and are caused to abut against caps 246. Continued opening of plates 252 drives barbed caps 246 into the endplates 22, 24 of the subject intervertebral disc space, as illustrated in FIG. 26C. Upon embedding the pin ends within the vertebrae, tool 250 is retracted proximally and device 240 is released from slots 254, as illustrated in FIG. 26D. Finally, as illustrated in FIGS. 26E and 26F, a prosthetic material 258 is delivered and cured as described above.

While various "inline" approaches have been described for delivering and implanting various embodiments of disc augmentation devices (primarily with respect to those illustrated in FIGS. 3-22), as mentioned above, the present invention also provides devices which involve a "transverse" approach to augmenting the disc where certain of the subject devices may be employed with either approach.

Figure 10B:
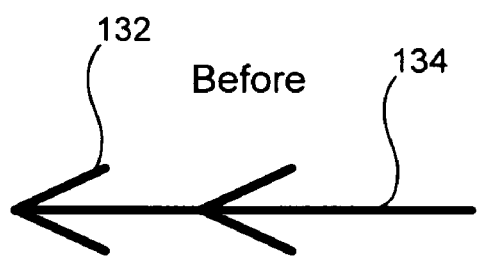
Figure 10C:
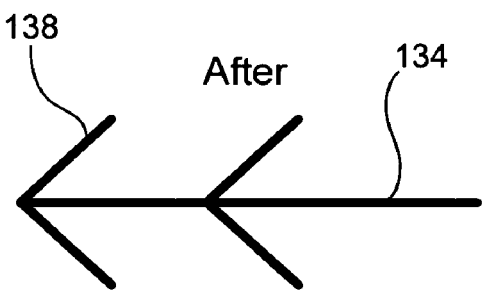
Figure 27:
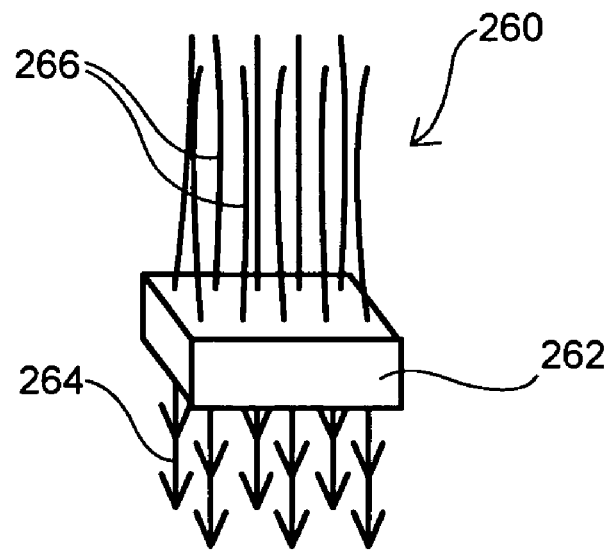
FIG. 27 illustrates an augmentation device similar to the device of FIG. 10A for implantation within a disc by way of a transverse approach to the annulus.
Figure 28A:
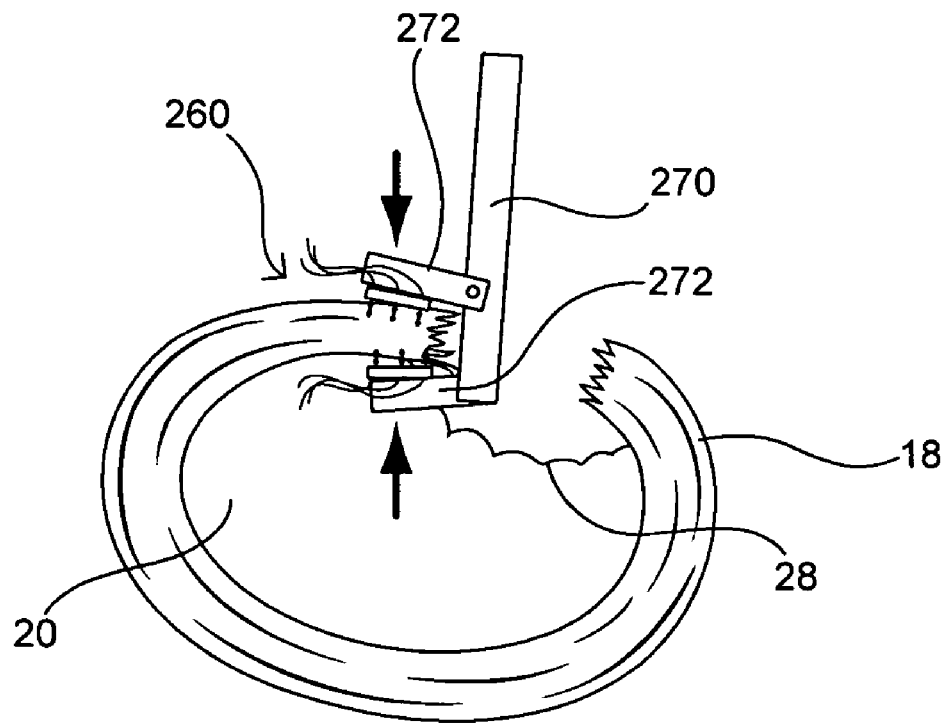
FIGS. 28A-28G illustrate various steps for implanting the disc augmentation device of FIG. 27 and for implanting a prosthetic material according to methods of the present invention.

For example, device 260 of FIG. 27, which is similarly configured to the device of FIGS. 10A-10C having a planar endplate or block 262 and a plurality of distally extending barbed anchors 264 and a plurality of trailing sutures or filaments 266, is implantable by an inline approach as illustrated in FIGS. 11A-11E as well as by the transverse approach illustrated in FIGS. 28A-2G.

Figure 28B:
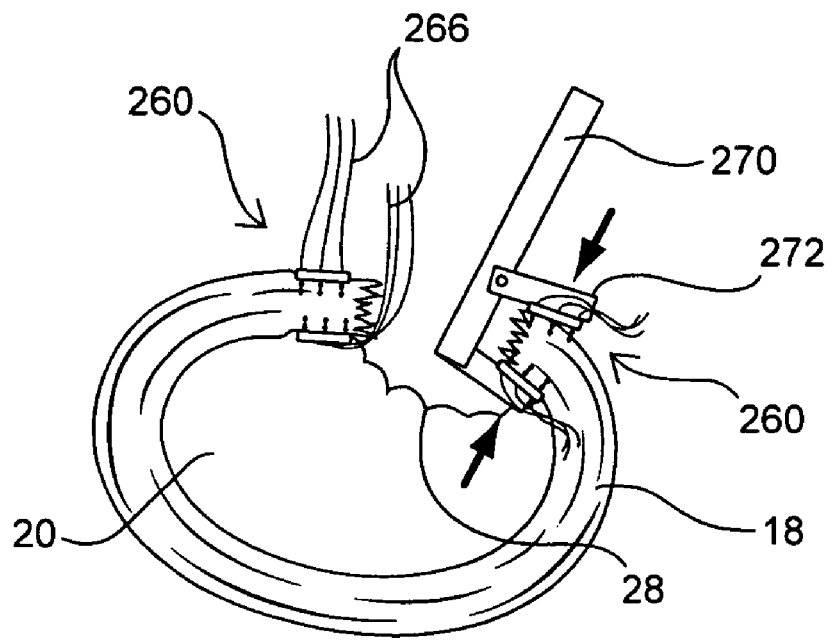
Figure 28C:
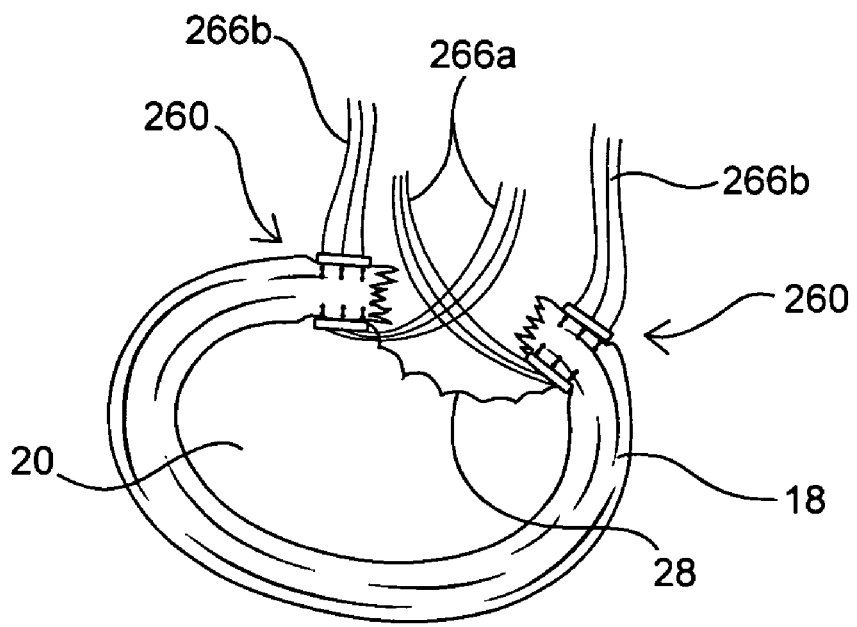
Figure 28D:
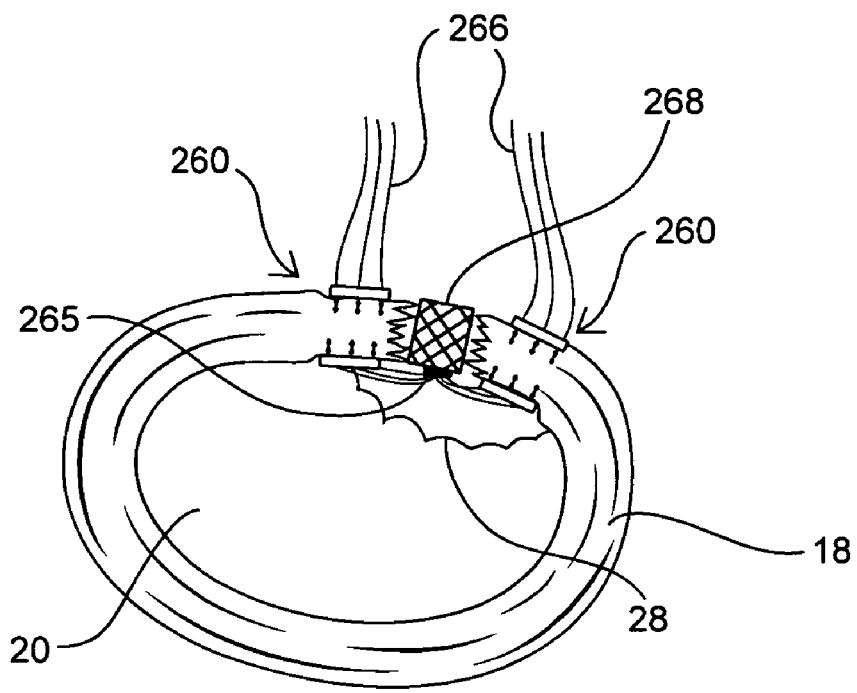
Figure 28E:
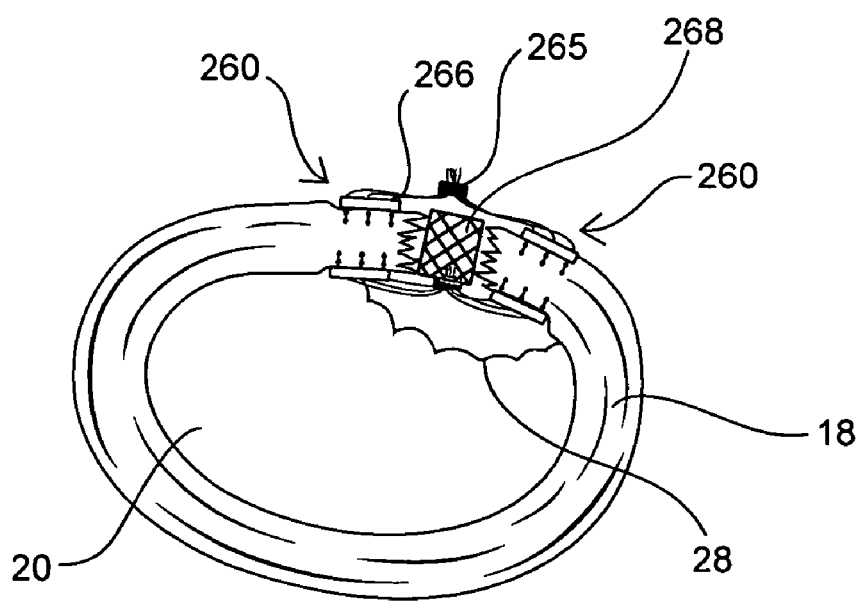
Figure 28F:
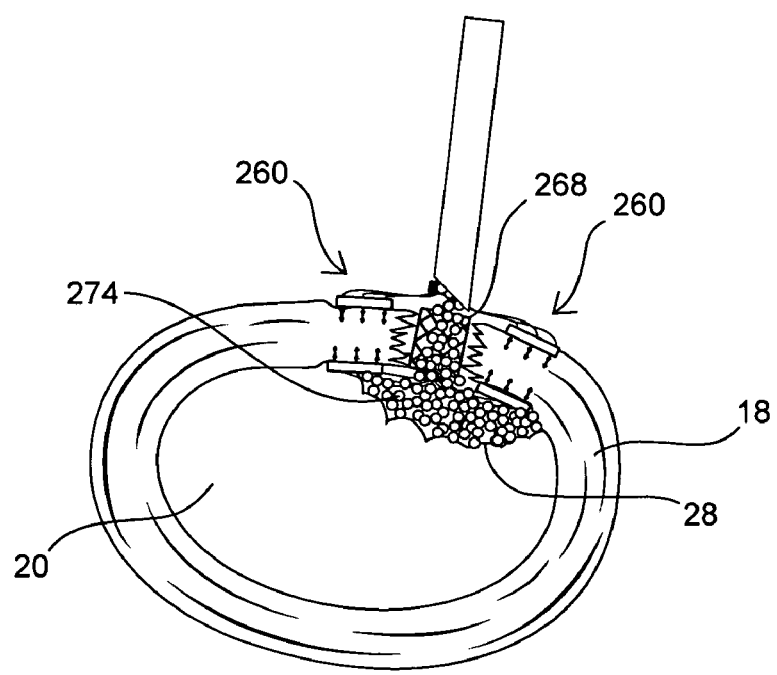
Figure 28G:
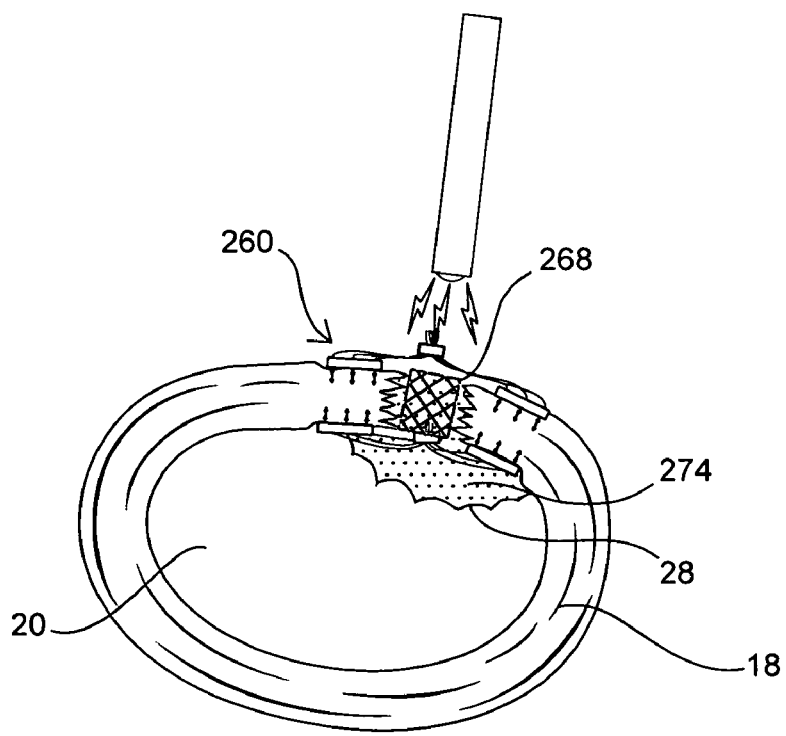

A pair of devices 260 used in tandem is delivered and implanted by means of delivery tool 270 which has opposing and substantially parallel jaws 272 at a distal end thereof wherein at least one jaw is movable relative to the other. Devices 260 are held within the inner, opposing surfaces of jaws 272 with anchors 264 facing each other. The distal end of tool 270 is positioned within defect or opening 28 within annulus 18 such that a cut or free end of the annulus is positioned or sandwiched between the two devices 260, as illustrated in FIG. 28A. Jaws 272 are moved together thereby penetrating anchors 264 into and transverse to the lamellar layers of clamped therebetween, where one device is implanted at the outer aspect of annulus 18 and the other device is implanted at the inner aspect of annulus 18. Tool 270 is removed and the process is repeated with another pair of devices 260 which is applied to the opposing free end of annulus 18, as illustrated in FIGS. 28B and 28C. The trailing sutures 266a of the devices 260 positioned at the inner aspect of annulus 18 are collectively synched and secured together by tie a tie or knot 265, as illustrated in FIG. 28D. A plug or core 268 having a porous or mesh construction so as to be permeable by a flowable prosthetic material is then positioned within the void between the free ends of annulus 18. The sutures or filaments 266b of the devices 260 positioned at the outer aspect of annulus 18 are then secured together with a second tie or knot mechanism 265, as illustrated in FIG. 28E. The combination of the implanted core 268 and the webs formed by sutures 266 define a scaffolding for augmenting the annulus and for receiving prosthetic material 274, as illustrated in FIG. 28F. After filling void 28, which may extend into nucleus 20, prosthetic material 274 is cured, as illustrated in FIG. 28G.

Figure 29:
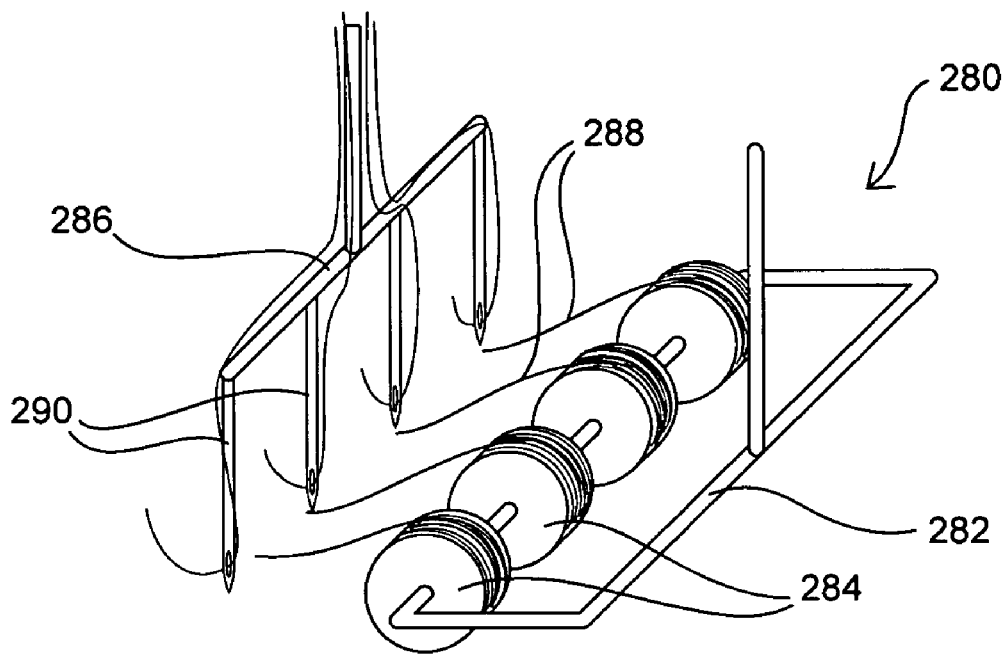
FIG. 29 illustrates a suture-based system of the present invention for augmenting an intervertebral disc.

FIG. 29 illustrates a system 280 of the present invention for applying a plurality of sutures or filaments 288 to a disc annulus in order to augment the disc as well as to provide a scaffolding for receiving a flowable prosthetic material. System 280 includes a suture spool holder 282 having a plurality of parallely aligned suture spools 284. System 280 also includes a needle carrier or driver 286 having a plurality of parallely aligned needles 290 configured for threadably receiving sutures 288. Needle driver 286 is automated such that it oscillates in much the same way a needle driven by a sewing machine. As needles 290 are driven into tissue, each of sutures 288 is placed within the tissue with a continuous length of suture material provided by spools 284.

Figure 30A:
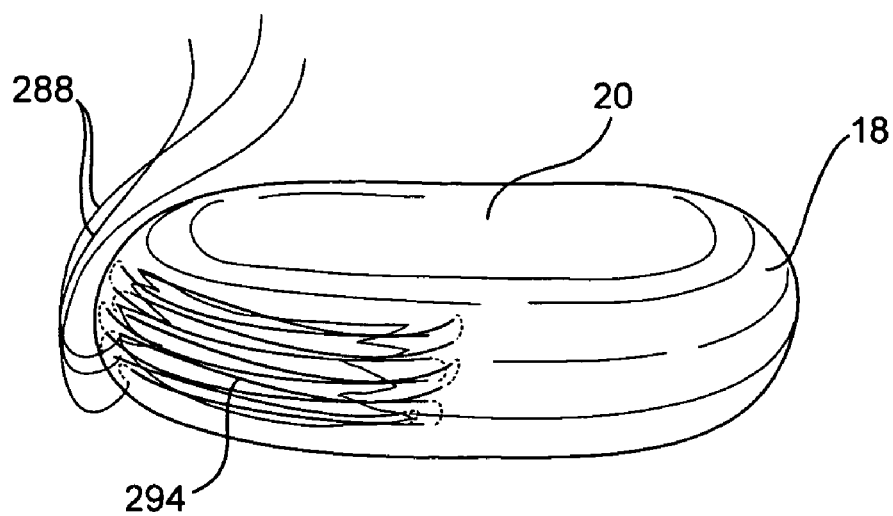
FIGS. 30A-30D illustrate various steps for augmenting a disc using the system of FIG. 29 for implanting a prosthetic material according to methods of the present invention.
Figure 30B:
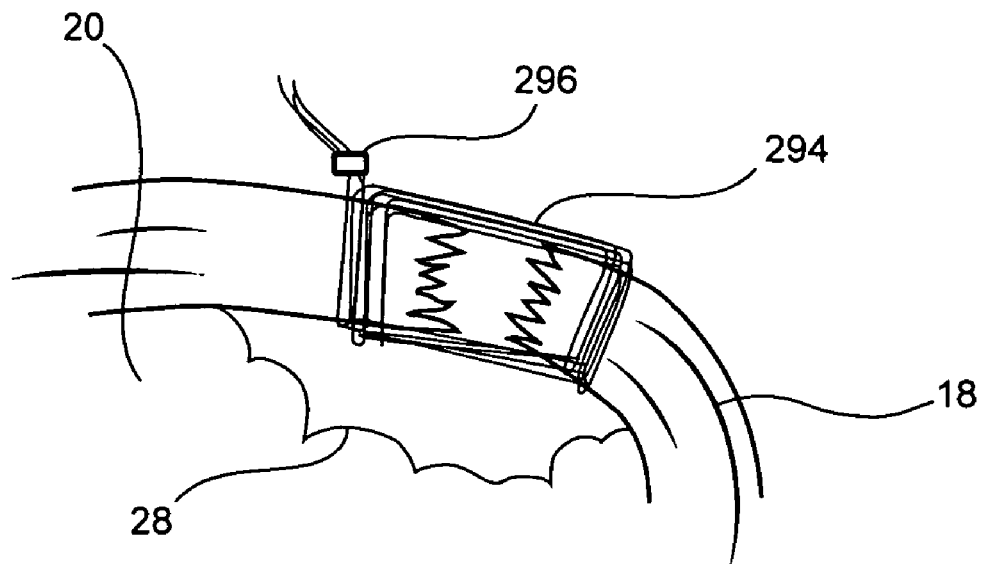
Figure 30C:
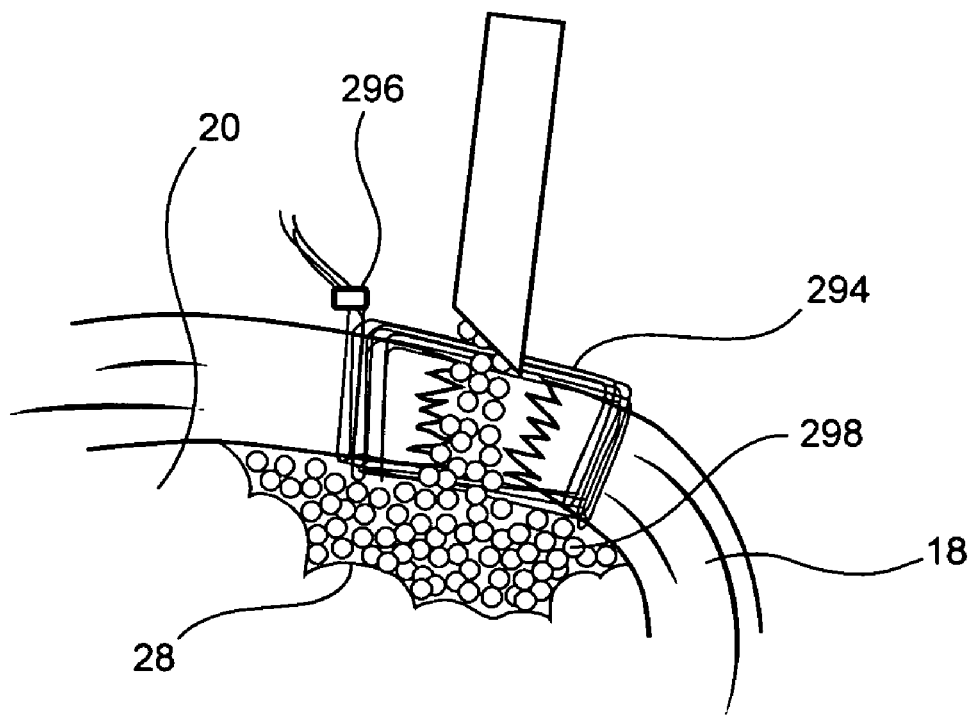
Figure 30D:
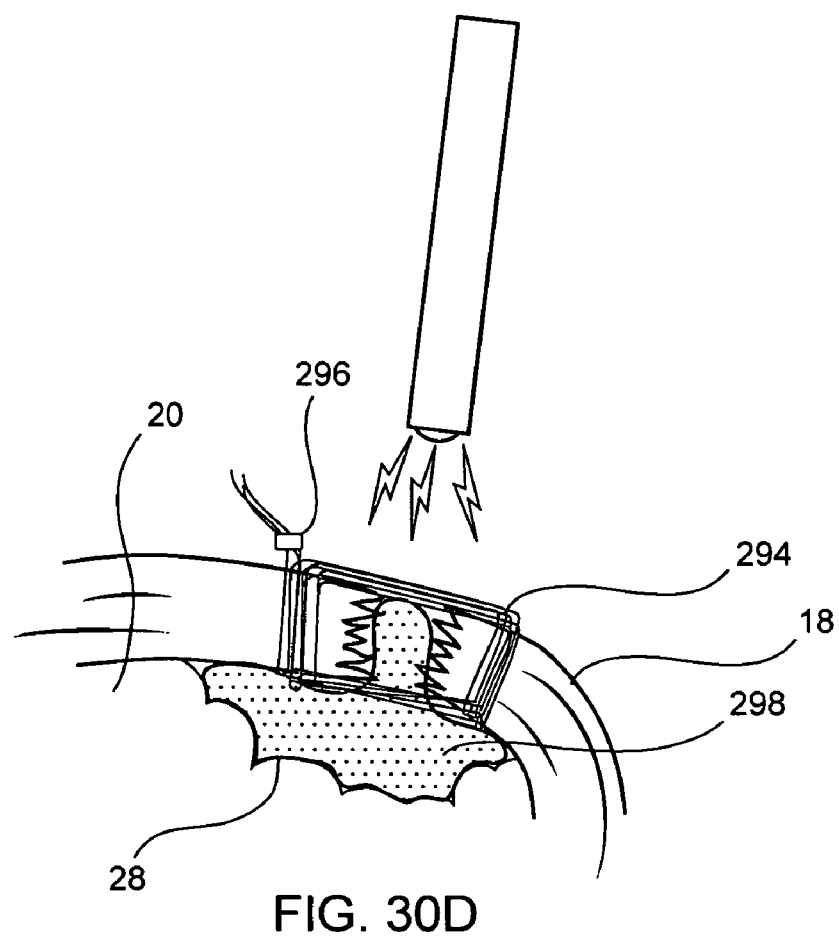

In use, system 289 is positioned at the outer aspect of annulus 18 with needles 190 poised to penetrate the annulus in a direction substantially transverse to the annulus layers. Needle driver 286 is actuated causing needles 290 to oscillate in and out of the annulus thereby placing the sutures in a selected pattern across a desired area of the annulus. As illustrated in FIGS. 30A and 30B, sutures 288 have been placed over a circumferential portion of annulus 18 to bridge across a defect therein to form a suture scaffolding 294. Sutures may be placed solely within the outer layers of the annulus 18 or may be driven through the entire thickness of the annulus to within the inner aspect so as to bridge across the defect at both the inner and outer aspects whereby a double layer of scaffolding is created. The loose, trailing ends of sutures 288 are then synched to place tension on the scaffolding and tied together with a knot or tie mechanism 296 to maintain the tension. Prosthetic material 298 may then be delivered into defect 28 through scaffolding 294, and subsequently cured, as illustrated in FIGS. 30C and 30D, respectively.

Figure 31A:
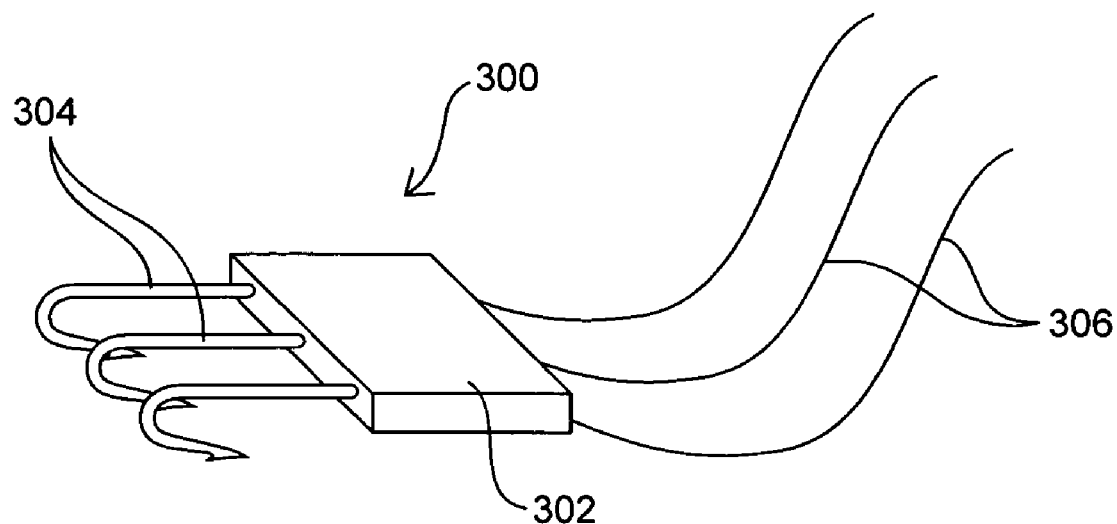
FIG. 31A illustrates another augmentation device of the present invention.

FIG. 31A illustrates another embodiment of an implantable device 300 which is used in tandem with at least one other of the same device to augment an intervertebral disc. Device 300 include a base member 302 having a planar configuration and a plurality of hooked anchors 304 extending from one edge of member 302 and a plurality of trailing sutures 306 extending from an opposite edge of base 302.

Figure 31B:
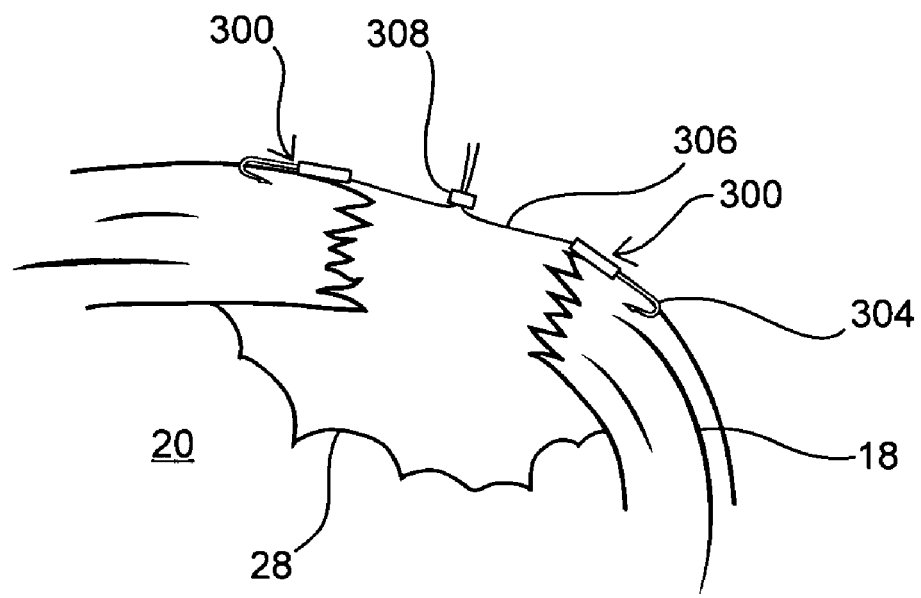
FIG. 31B illustrates a pair of the augmentation device of FIG. 31A operatively implanted within an intervertebral disc.

As can be seen in FIG. 31B, a pair of devices 300 is hooked into the outer aspect of free ends of annulus 18 with the trailing sutures 306 of each device tied together by a tie or knot mechanism 308 in order to place tension on the annulus and provide a scaffolding which bridges across void 28. An additional pair of devices 200 may be similarly implanted at the inner aspect of annulus 18 with their trailing sutures tied together either separately from those of the pair of devices on the outer aspect or together with them.

Figure 32A:
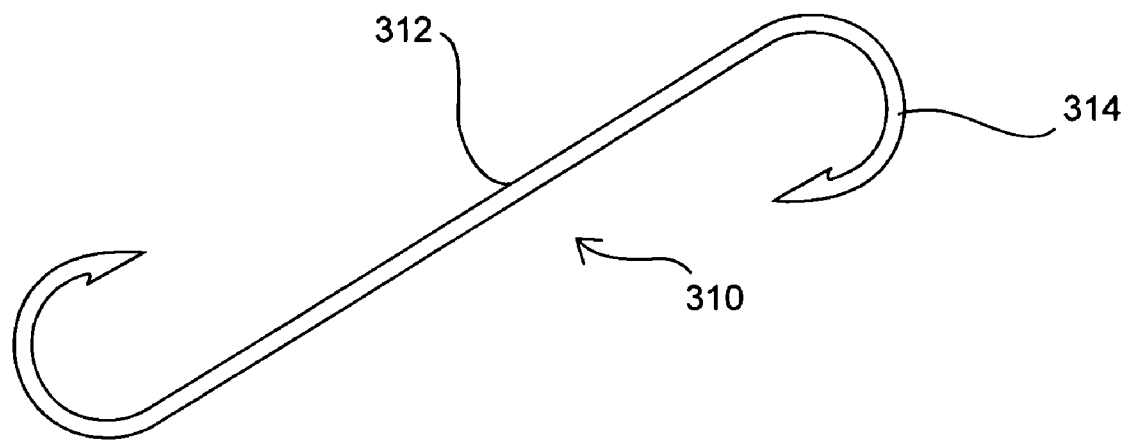
FIG. 32A illustrates another augmentation device of the present invention.
Figure 32B:
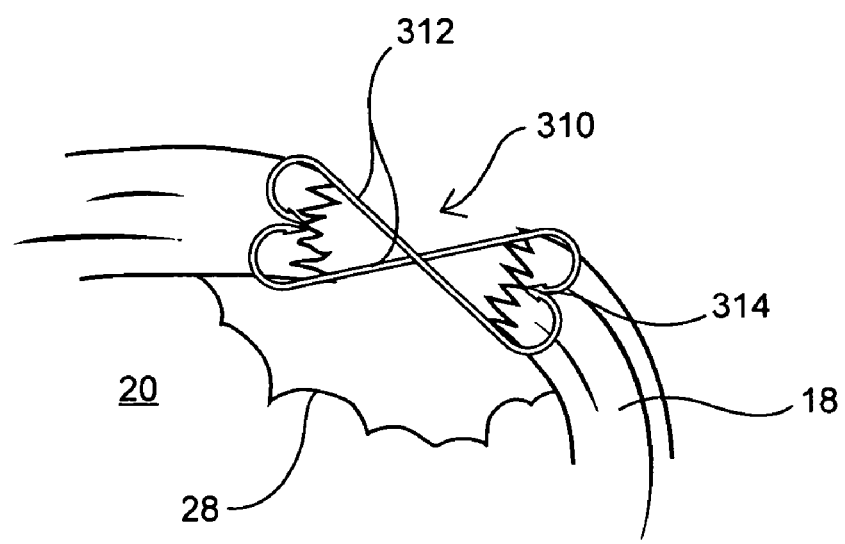
FIG. 32B illustrates a pair of the augmentation devices of FIG. 31A operatively implanted within an intervertebral disc.

FIG. 32A illustrates another embodiment of an implantable device 310 which may be used alone or in tandem with one other of the same device to augment an intervertebral disc. Device 310 includes an elongated member 312 having hooked ends 314. Hooks 314 may be oppositely oriented to provide an "S" shape (as shown) or may be oriented towards the same side of member 312 or in any other orientation. In use, with the configuration of FIG. 32A, one hook 314 is placed through an outer aspect of annulus 18 on one side of a defect 28 and the other hook 314 is placed in an inner aspect of the other side of defect 28, as illustrated in FIG. 32B. FIG. 32B shows two such devices 310 employed in tandem and placed conversely of each other with members 312 crossing centrally within void 28 to provide a scaffolding which bridges the void.

Figure 33:
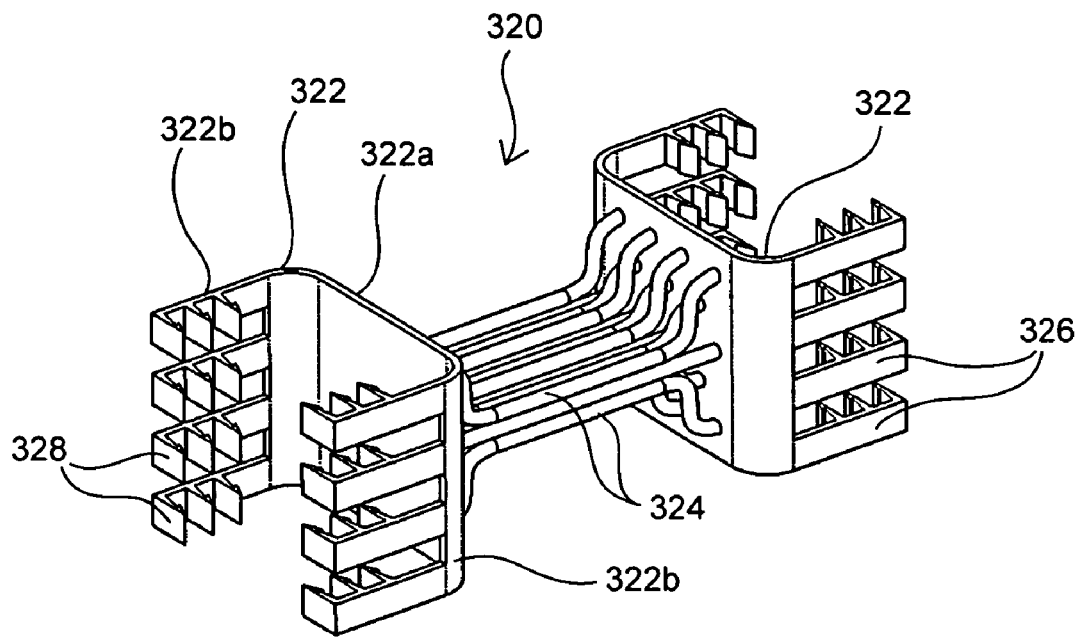
FIG. 33 a clamp-type disc augmentation device of the present invention.

FIG. 33 illustrates an implantable clamp device 320 of the present invention for augmenting an intervertebral disc. Implant 320 includes oppositely facing clamps 322, each defined by a back plate 322a and two opposing sidewalls 322b, 322c, and a plurality of parallel chords 324 extending transversely between back plates 322a. Clamps 322 each have a plurality of fingers 326 formed in sidewalls 322b, 322c having inwardly extending teeth 328 for anchoring into tissue.

Figure 34:
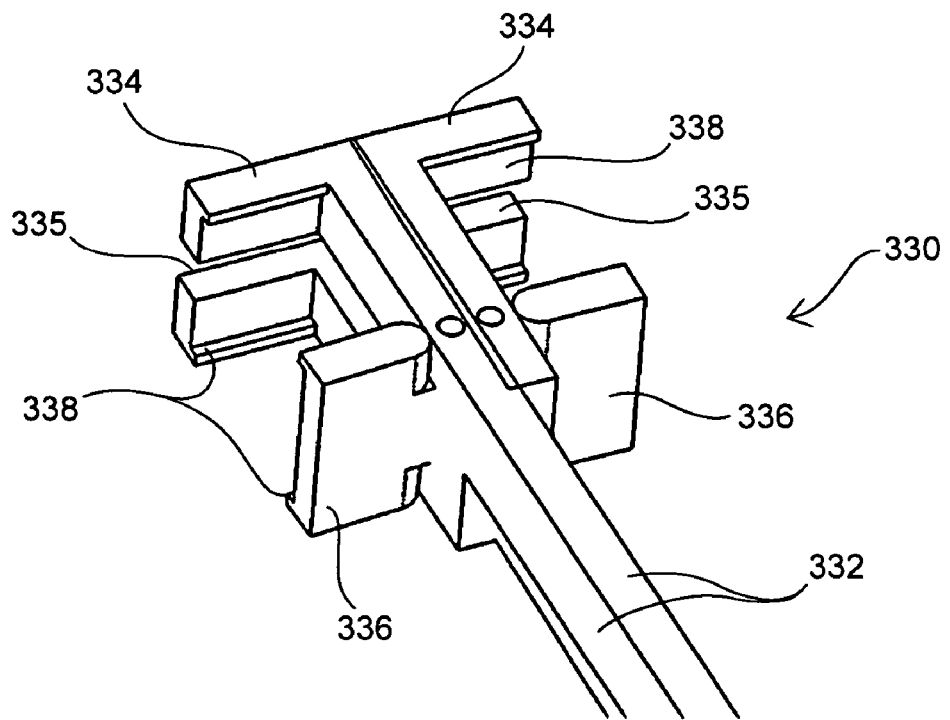
FIG. 34 a distal portion of a delivery tool for implanting the device of FIG. 33.
Figure 35A:
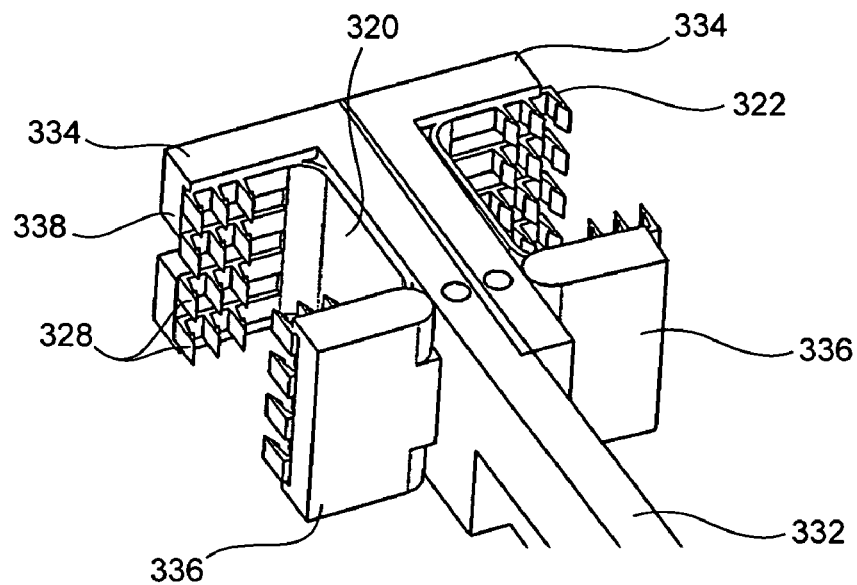
FIGS. 35A-35H illustrate various steps for implanting the disc augmentation device of FIG. 33 utilizing the delivery tool of FIG. 34 and for implanting a prosthetic material according to the methods of the present invention.

FIG. 34 illustrates the distal end of an insertion tool 330 for use in delivering the device of 320 into a defect within a disc. Tool 330 has opposing arms 332 which are pivotally coupled to a handle and operate in a scissor-like fashion with respect to each other. The distal end 334 of each arm 332 has a laterally extending distal foot defining an L-shaped configuration and has a slot 335 extending centrally along the length of distal end 334 for receiving chords 324 of clamp device 320. Proximally positioned of distal feet 334 are laterally extending feet 336 which are pivotally coupled to arms 332. The facing surfaces of distal and proximal feet have top and bottom lip edges 338 to engage against sidewalls 322b, 322c of clamp device 320 to retain the device upon loading within tool 330, as illustrated in FIG. 35A.

Figure 35B:
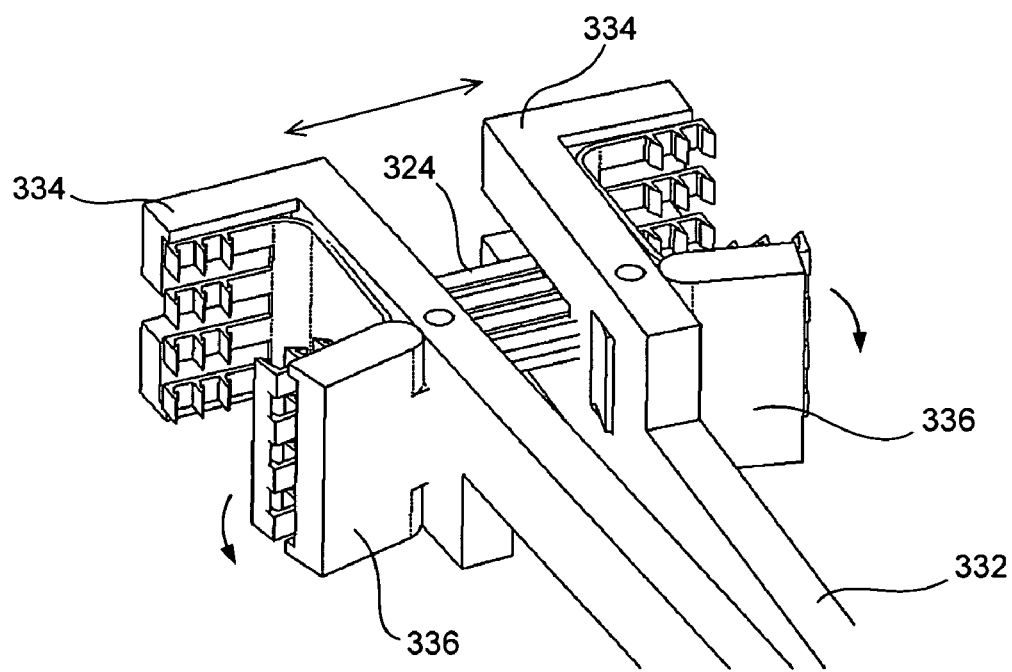
Figure 35C:
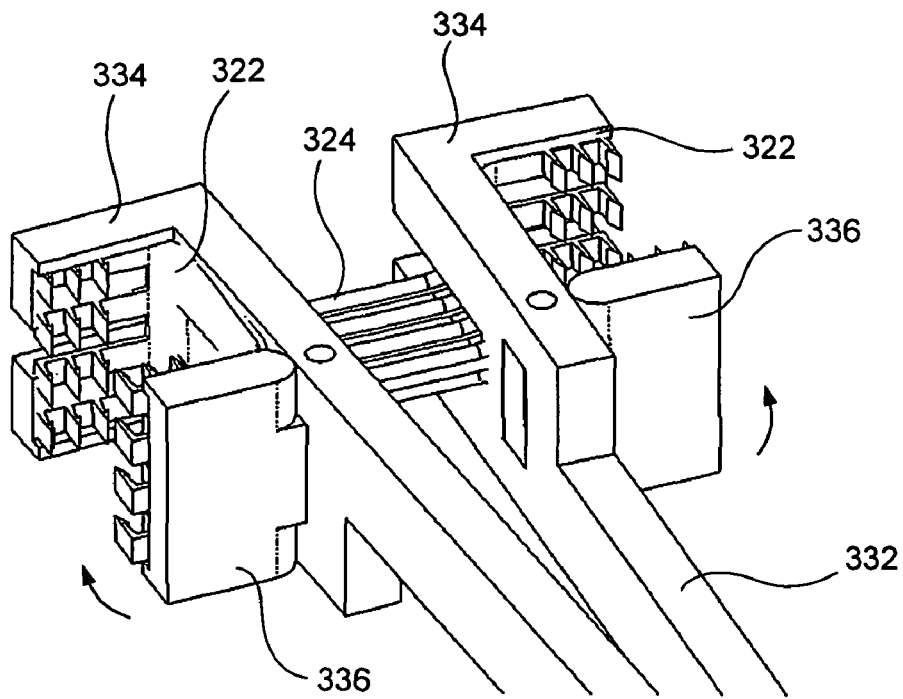
Figure 35D:
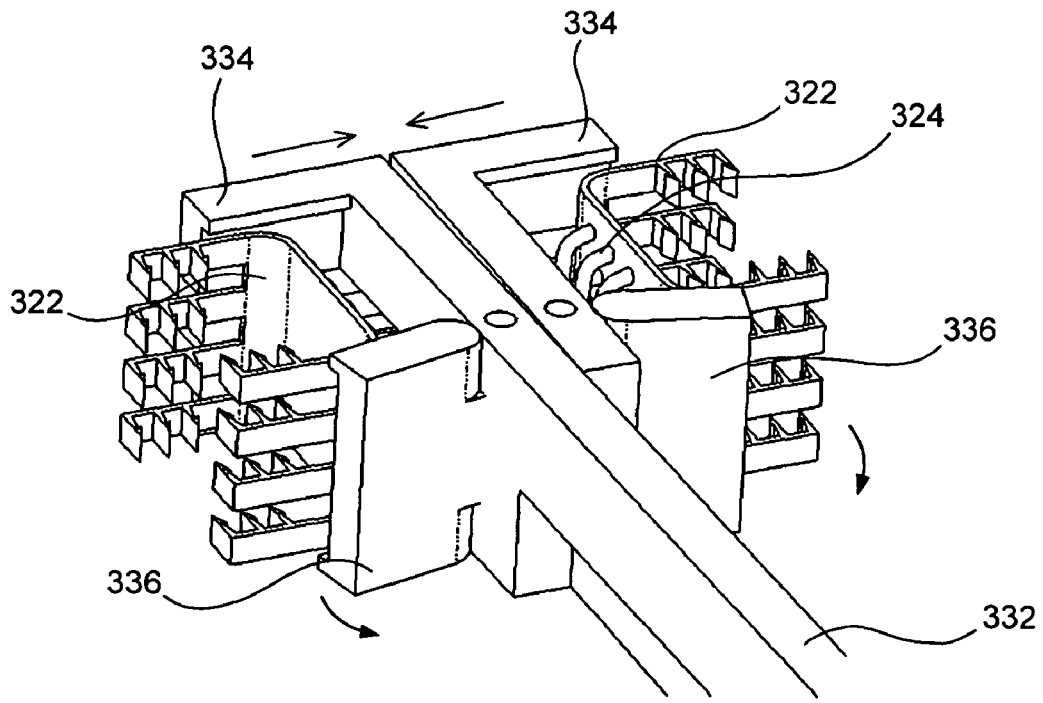
Figure 35E:
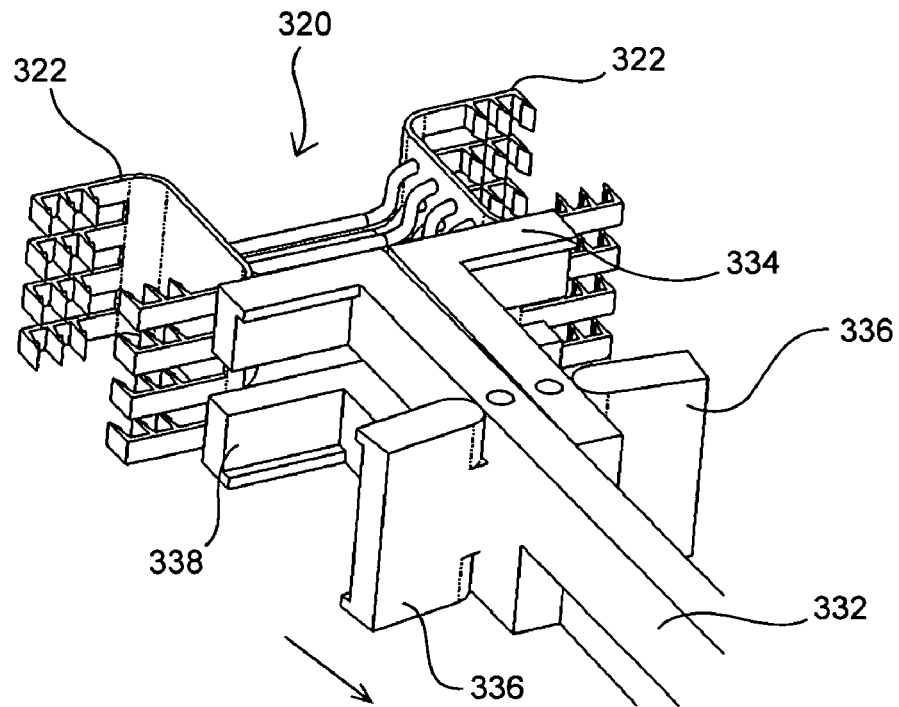
Figure 35F:
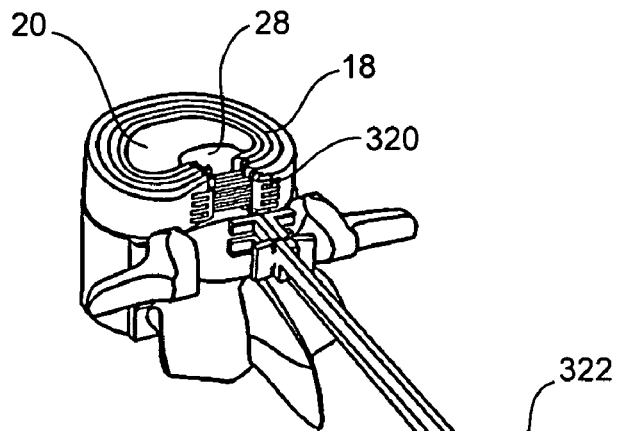

Upon positioning the pre-loaded distal end of tool 330 within a void within a disc annulus (tool is shown outside implant site for clarity in illustration), arms 332 are spread apart thereby stretching or extending chords 324 of implant 320, as illustrated in FIG. 35B. At the same time, proximal feet 336 may be pivoted proximally or backwards so as to facilitate positioning of the free ends of the annulus within clamp members 322. Next, as illustrated in FIG. 35C, proximal feet 336 are pivoted distally or forward to compress sidewalls 322b and 322c together thereby anchoring clamp members 322 within the respective annulus ends. Proximal feet 336 are then pivoted backwards again to release the clamp members, while arms 332 are closed to the extent that the back plates 322a are cleared, as illustrated in FIG. 35D. Tool 330 is then pulled from the access site, leaving device 320 behind within the annulus, as illustrated in FIGS. 35E and 35F.

Figure 35G:
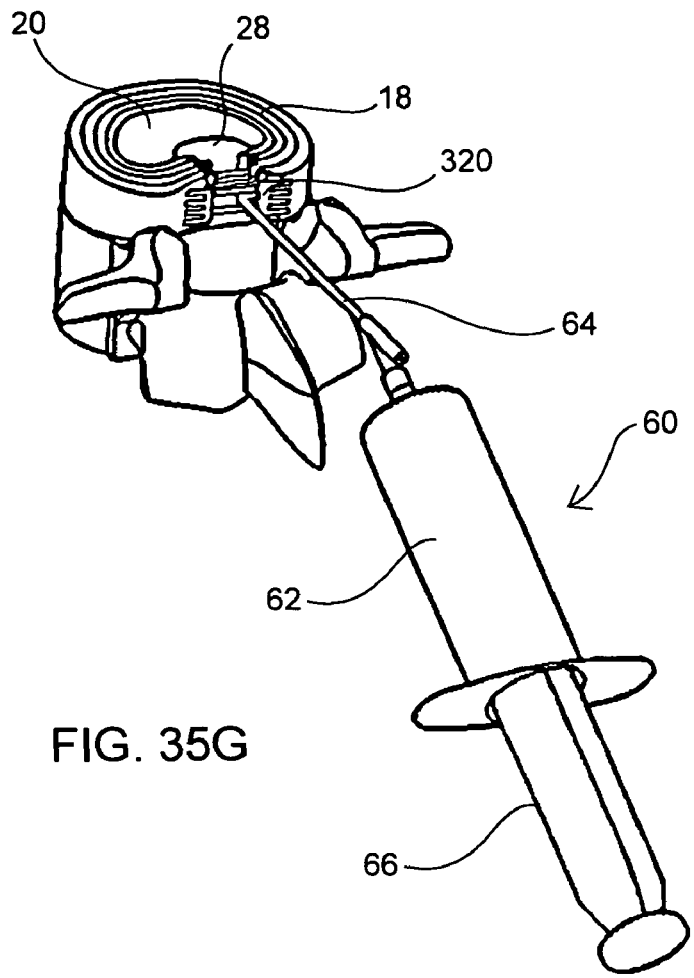
Figure 35H:
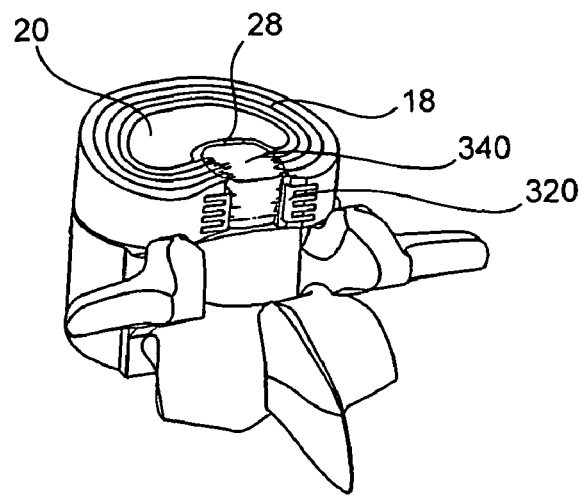

In a manner similar to that described various times above, an injector device 60 is then used to inject or extrude prosthetic material within void 28, as illustrated in FIG. 35G. The spacing between the chords 324 of device 320 is sufficient to provide a fluid pathway and allow filling of the intra-annular space with prosthetic material 340 as shown in FIG. 35H.

Figure 36A:
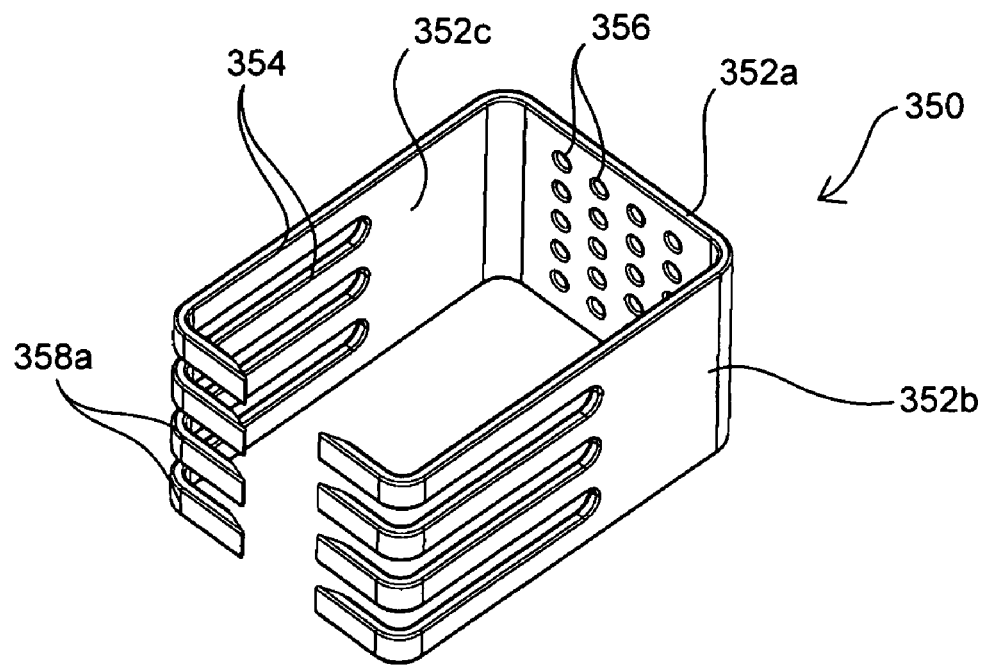
FIGS. 36A and 36B illustrate alternate clamp designs for disc augmentation devices of the present invention.
Figure 36B:
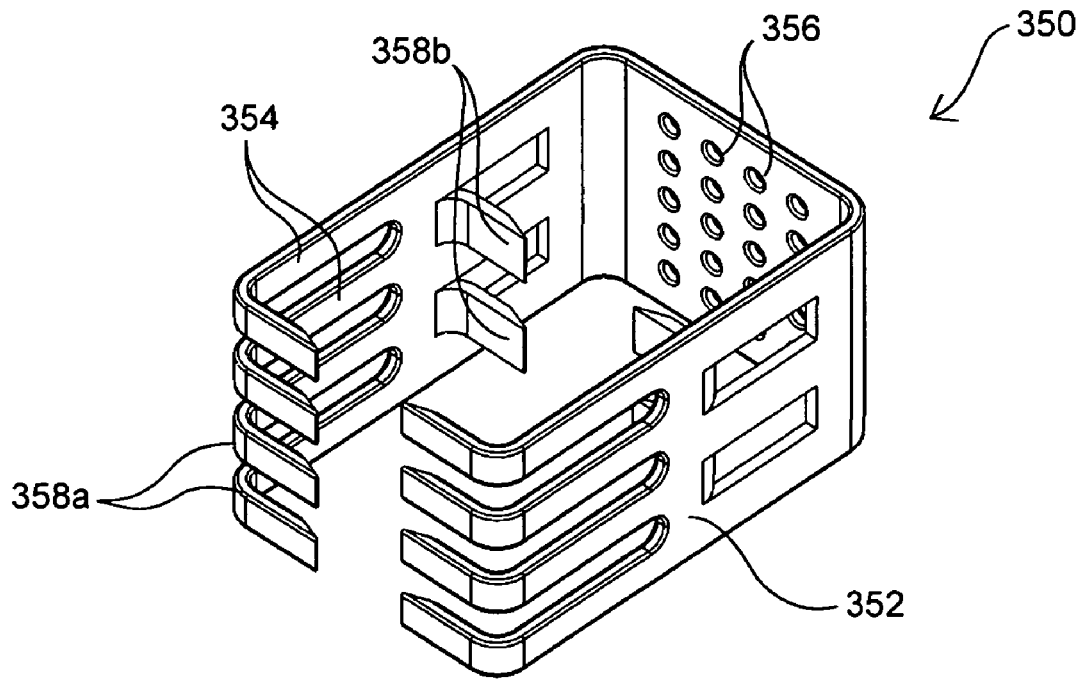
Figure 37:
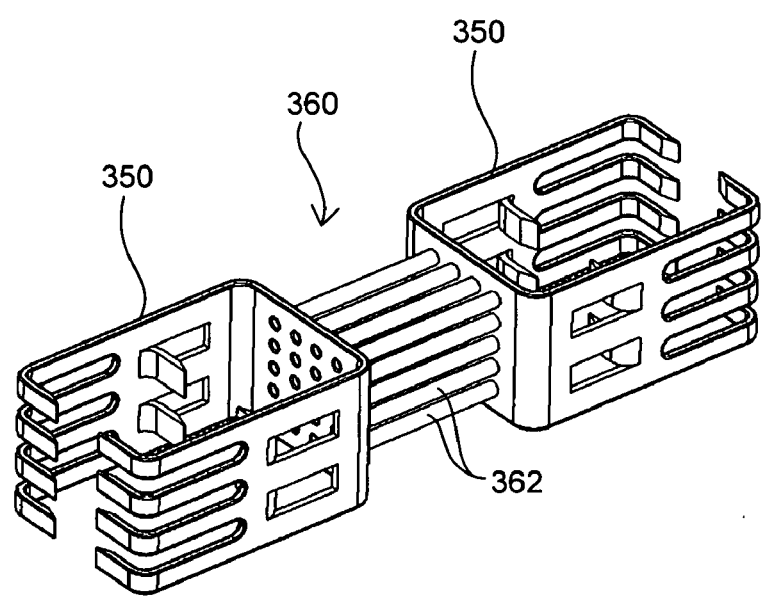
FIG. 37 illustrates another clamp-type disc augmentation device employing the clamp design of FIG. 36B.

Alternate clamp designs that are usable for clamp-type augmentation devices of the present invention are illustrated in FIGS. 36A and 36B. Clamp 350 includes a frame 352 having back plate 352a having apertures 356 for receiving chord ends and sidewalls 352b, 352c terminating in fingers 354 having inwardly extending anchors 358a. As shown in FIG. 36B, additional anchors 358b may be provided to ensure retention of the clamps on the annulus. FIG. 37 illustrates a clamp device 360 employing clamp mechanisms 350 of FIG. 36B interconnected by chords 362.

Figure 38A:
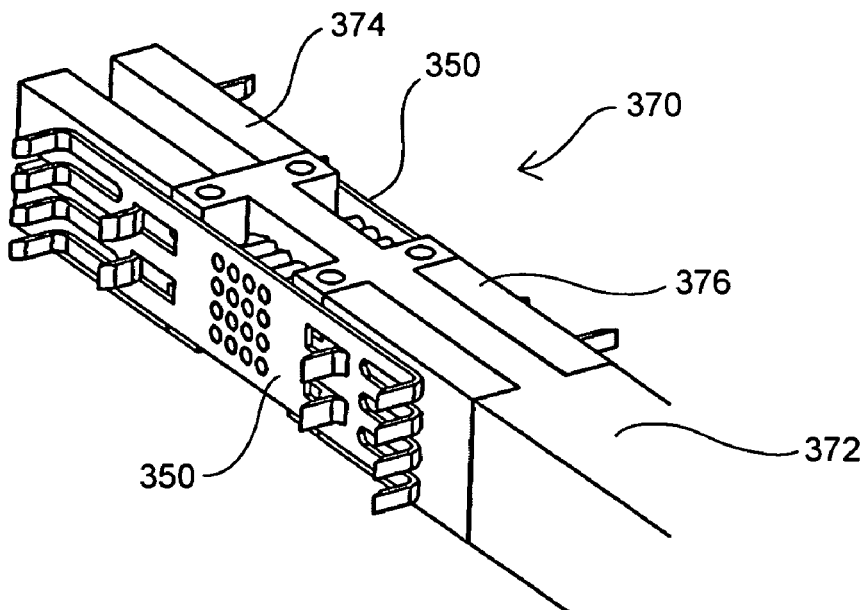
FIGS. 38A-38F illustrate various steps for implanting the disc augmentation device of FIG. 37 and for implanting a prosthetic material according to the methods of the present invention.
Figure 38A:
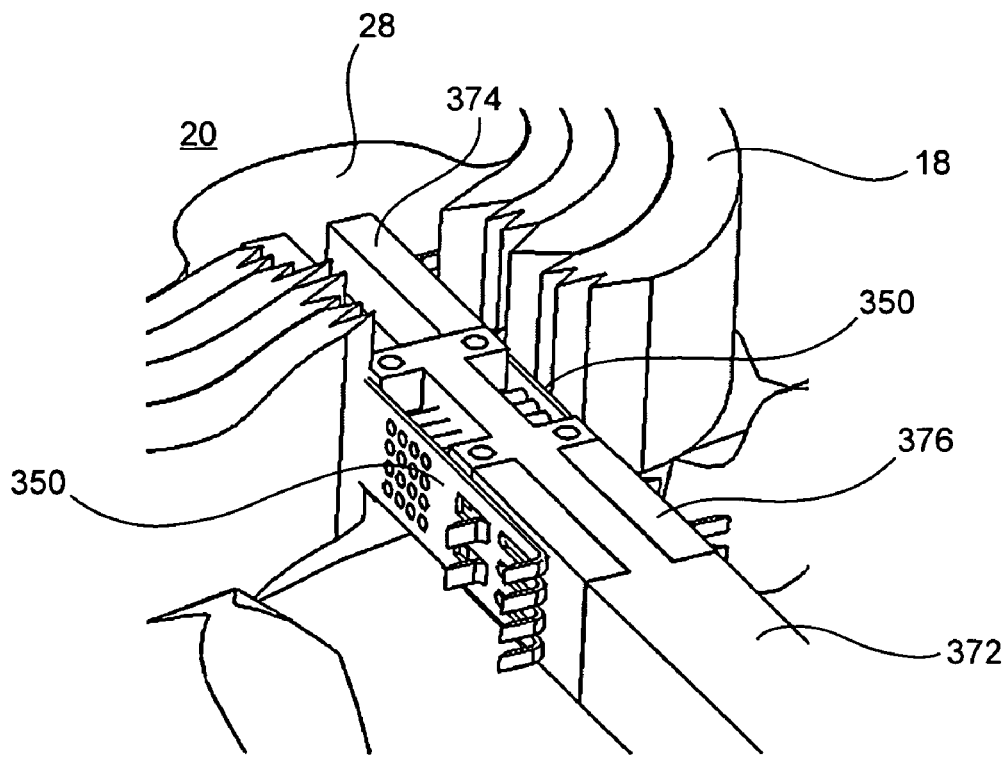
Figure 38B:
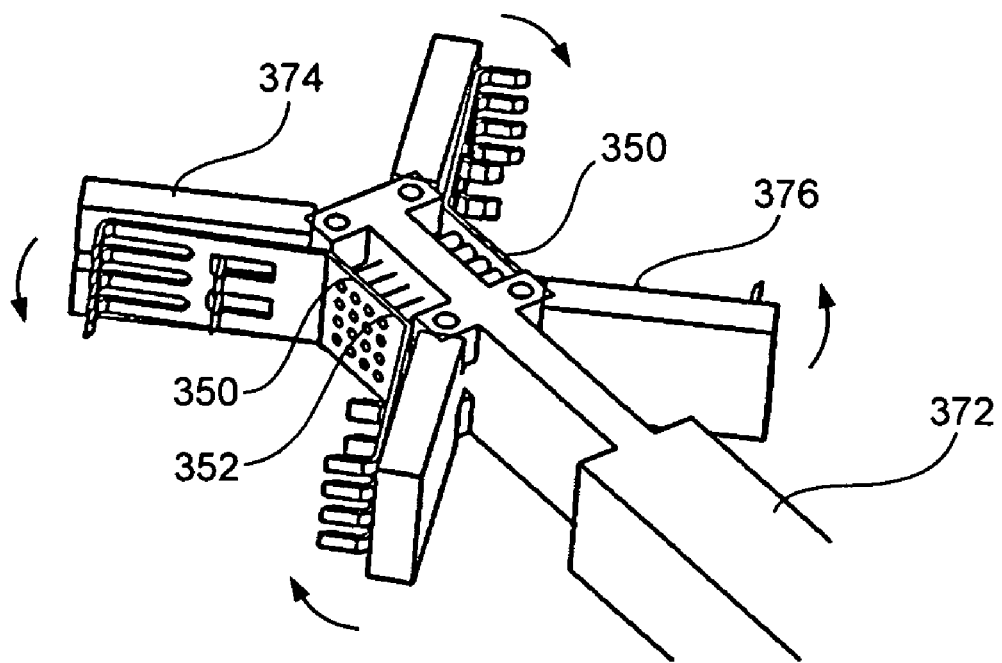
Figure 38B:
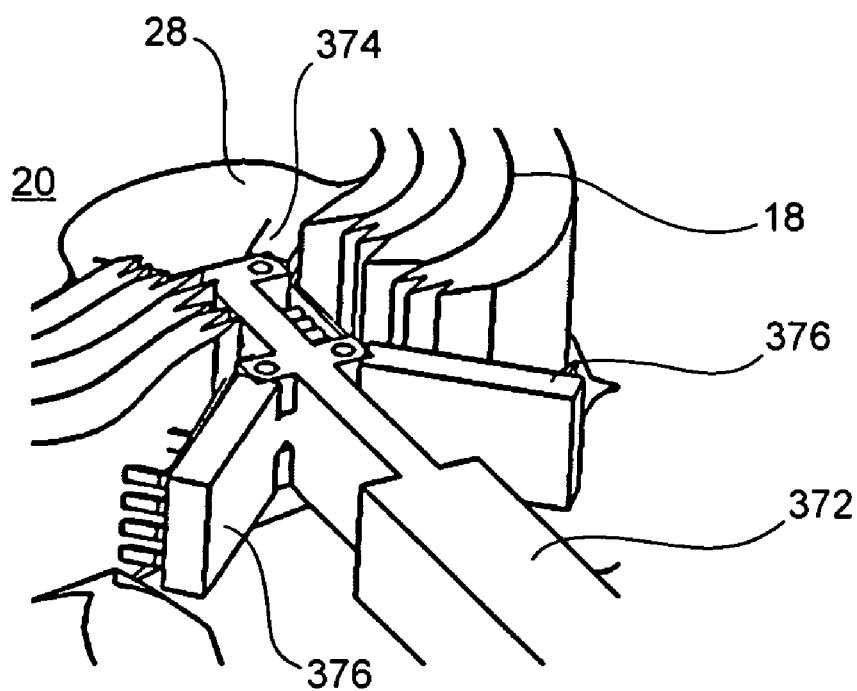
Figure 38C:
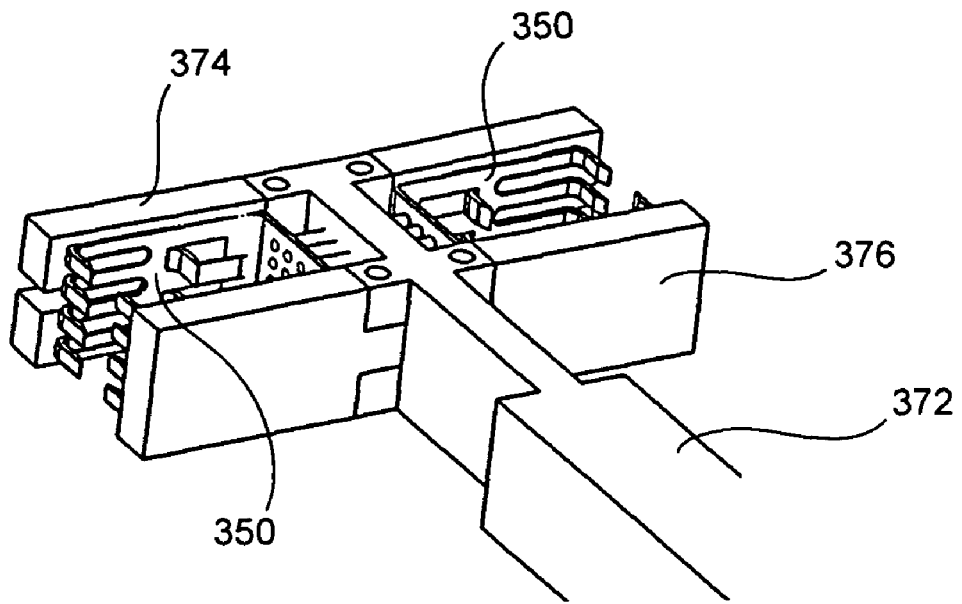
Figure 38C:
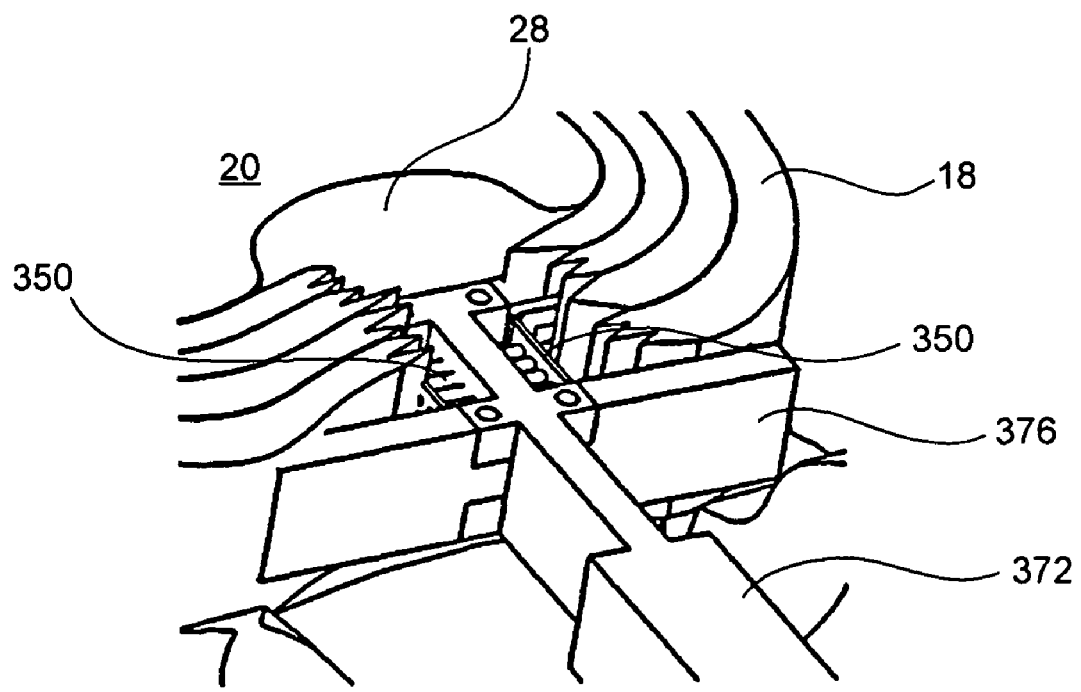
Figure 38D:
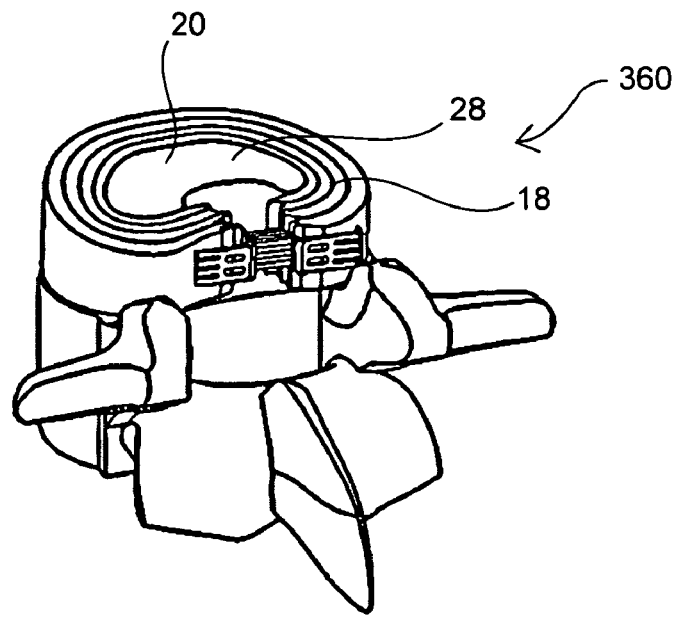

As illustrated in FIG. 38A, the corners interconnecting the sidewalls with the back plate of clamp members 350 may be flexible, deformable or hinged to allow for straightening of frame 322 (or if originally provided in a straightened configuration, then for bending or folding frame 322 to form the configurations illustrated in FIG. 37) for pre-loading onto a delivery tool 372 in a low-profile state. Tool 372 is similar to tool 330 of FIG. 34 but having pivoting distal fee 374 in addition to pivoting proximal feet 376. A slot (not visible) is provided within distal feet 374 for receiving chords 362 of device 360. The low-profile state facilitates minimally invasive delivery into an annular defect 28, as illustrated in FIG. 38A'. Upon proper alignment of device 360 within annulus 18, both sets of feet 374, 376 are pivoted inward thereby bending sidewalls 352b, 352c of frames 352 to close upon the free ends of annulus 18, as illustrated in FIGS. 38B and 38B'. Feet 374, 376 are further advanced toward each other thereby penetrating anchors 358a, 358b into the annulus tissue as illustrated in FIGS. 38C and 38C'. All feet are then pivoted apart to release the clamp members 350, and tool 372 is then pulled from the access site, leaving device 360 behind within the annulus, as illustrated in FIG. 38D.

Figure 38E:
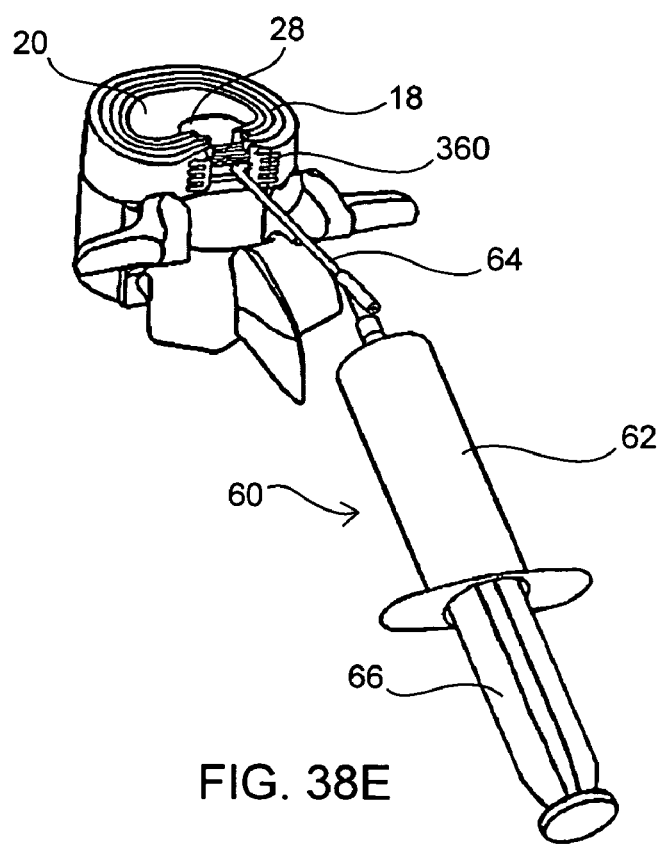
Figure 38F:
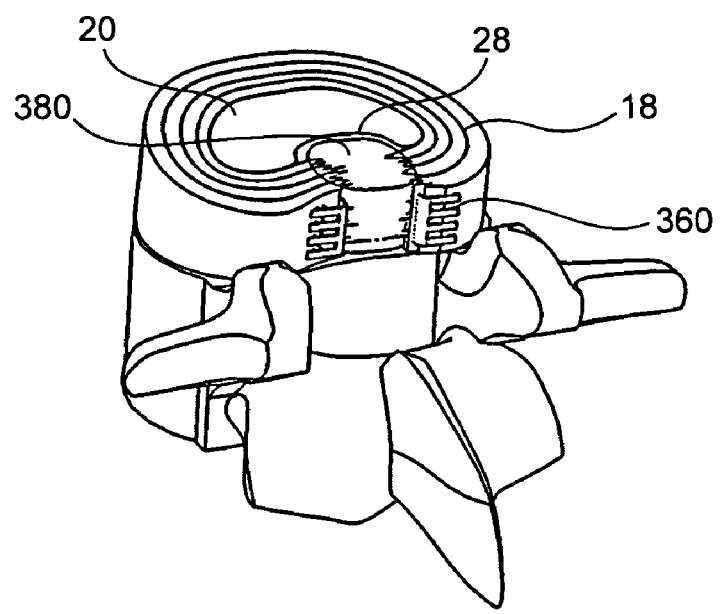

In a manner similar to that described above, an injector device 60 is then used to inject or extrude prosthetic material 360 within void 28, as illustrated in FIG. 38E. The spacing between the chords 324 of device 320 is sufficient to provide a fluid pathway and allow filling of the intra-annular space with prosthetic material 340 as shown in FIG. 38F.

Figure 39A:
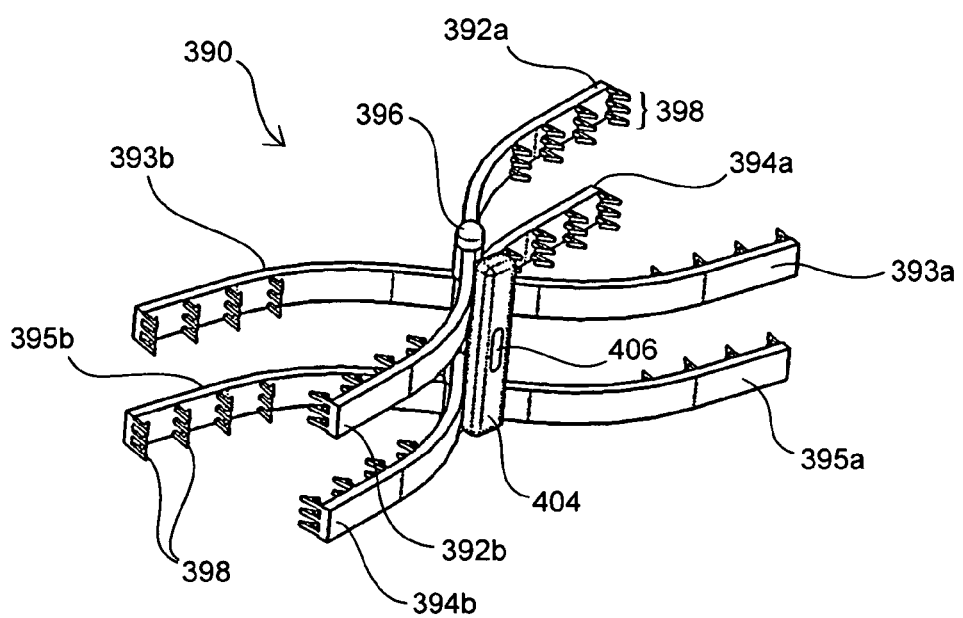
FIG. 39A-39C show perspective and top views of a clip-type embodiment of an augmentation device of the present invention.
Figure 39C:
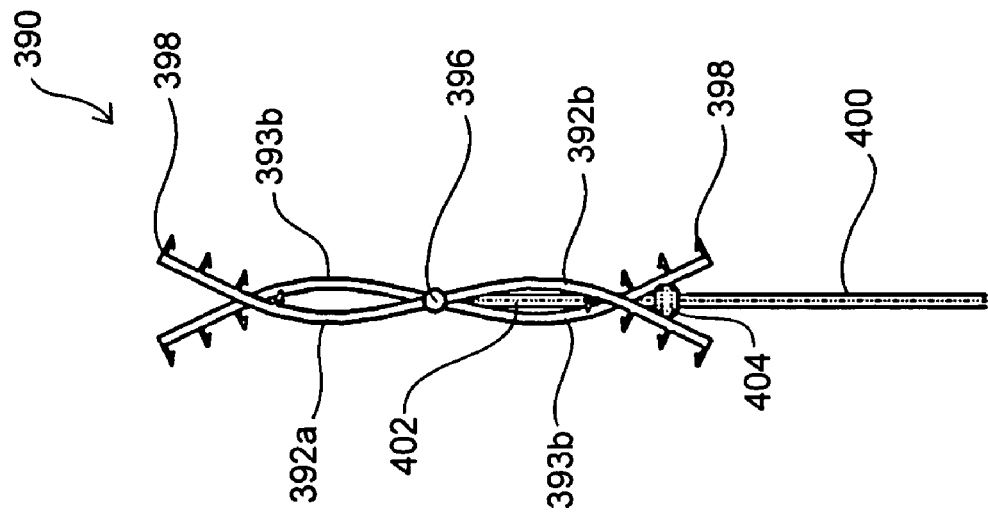
Figure 39B:
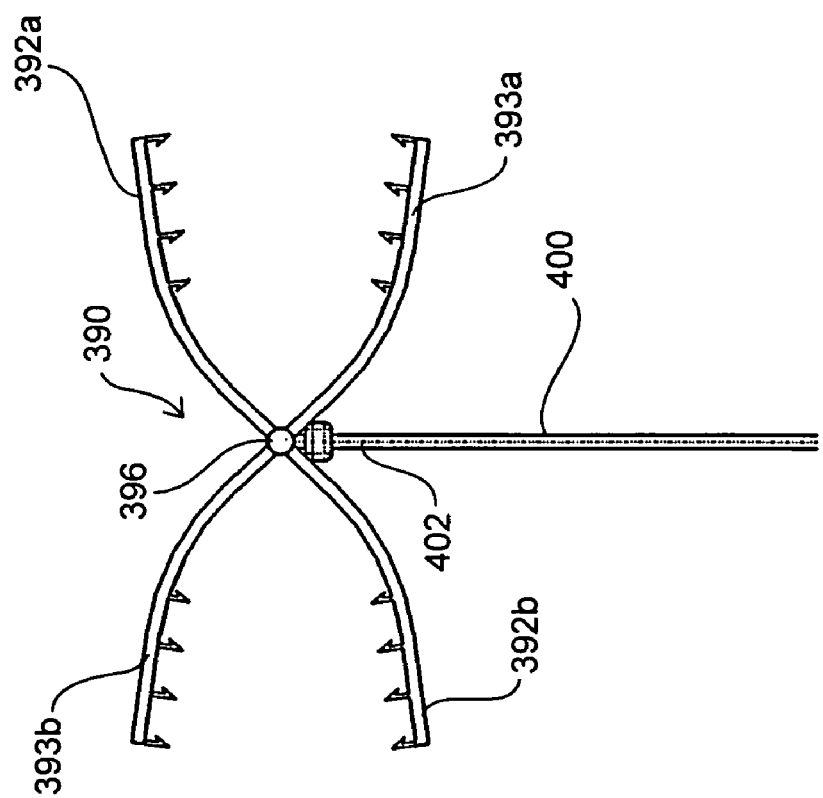

FIG. 39A-39C illustrates another disc augmentation device 390 having a clip configuration. Device 390 has a plurality of laterally extending arm pairs 392-395, each arm pair being pivotable about a central vertical core 396 between open (FIGS. 39A and 39BA) and closed (FIG. 39C) positions. The arms on each side of clip 390 may be independently movable of the arms on the opposite side, or may be collectively movable as illustrated. Each arm may be directly opposed to another arm on the same side such that they appose each other when closed, or they may be interdigitated as illustrated such that they cross when closed (see FIG. 39C), resulting in a stacked arrangement on each side (i.e., from top to bottom: 392a, 393a, 394a, 395a and 392b, 393b, 394b, 395b). The inner sides of the arms may be provided with teeth 398 for penetrating into engaged or captured tissue, e.g.; the annulus, held between the arms.

Figure 40A:
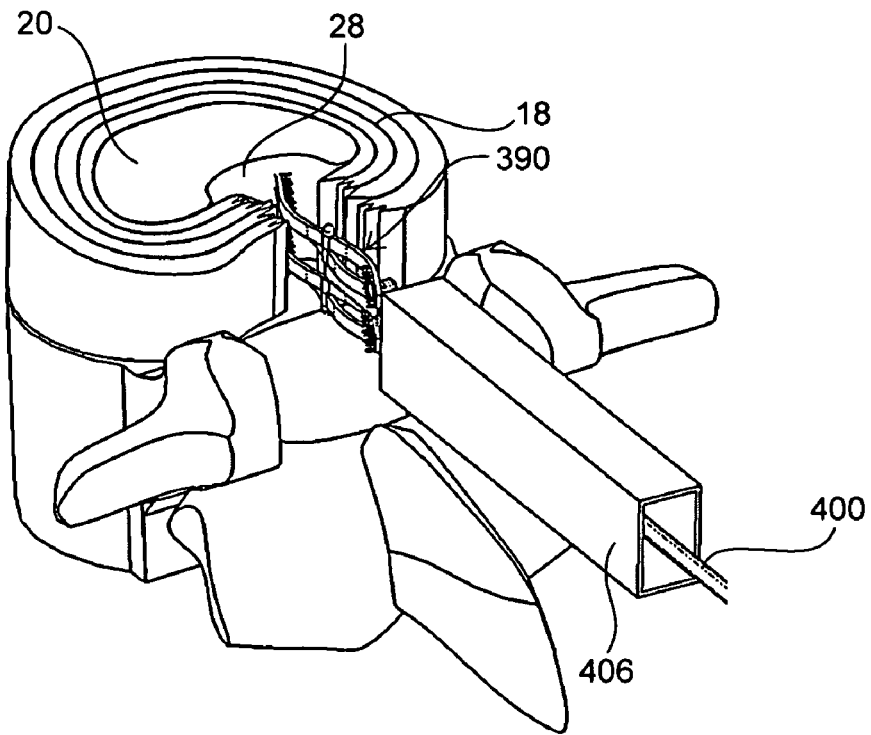
FIGS. 40A-40D illustrate various steps for implanting the disc augmentation device of FIGS. 39A-39C and for implanting a prosthetic material according to methods of the present invention.
Figure 40B:
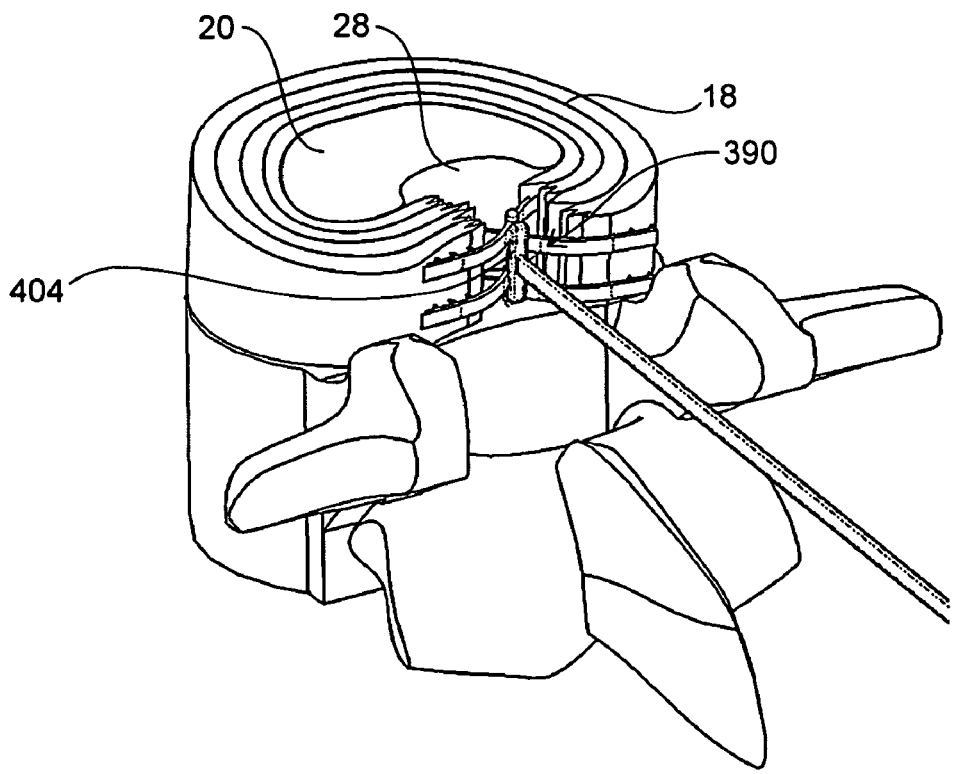

In FIGS. 39B and 39C, disc augmentation device is operatively coupled to the distal end 402 of actuator rod 400 which controls the motion of the arms. In an open configuration, clip 390 has a low profile relative to the axis of actuator rod for easy delivery through delivery sheath 406, as illustrated in FIG. 40A. Clip 390 is operatively positioned within the intervertebral disc when its core 396 is substantially centrally positioned within and along the lamellar planes of annulus 18 and the arms straddle the opening across the entire thickness of the annulus. A pusher mechanism 402, having a slot 408 for slidable translation over actuator rod 400 in a transverse relationship, is advanced distally against the outer surfaces of proximal arms 392b, 393a, 394b, 395a, which may be biased open, thereby forcing the arms closed and clamping or sandwiching the cut or bisected ends of annulus 18 therebetween, as illustrated in FIG. 40B. The arms may be configured to lock upon achieving a sufficiently closed position or may be locked in place by means of pusher mechanism 404 which is left coupled to implanted clip 390.

Figure 40C:
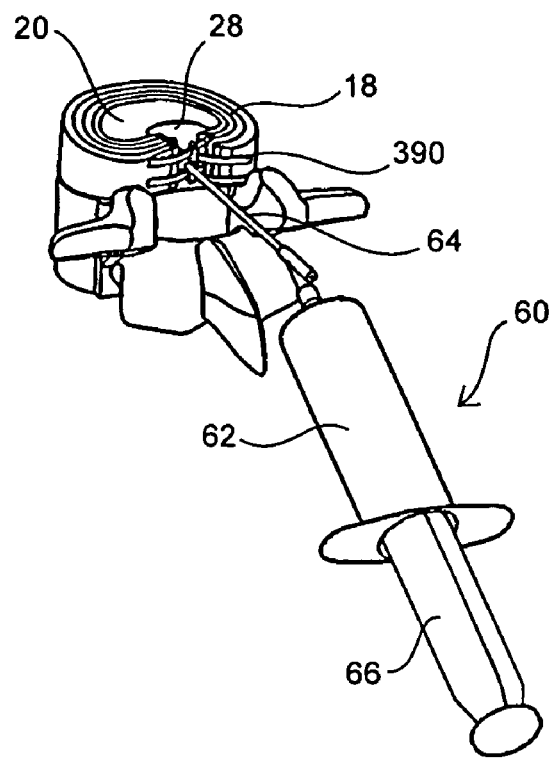
Figure 40D:
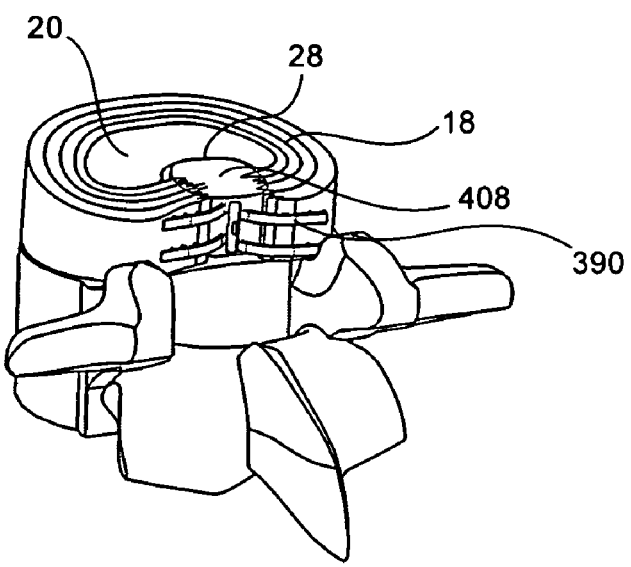

In a manner similar to that described above, an injector device 60 is then used to inject or extrude a prosthetic material 408 within void 28, as illustrated in FIG. 40C. The transverse and axial spacing between the arms of clip 390 is sufficient to provide a fluid pathway and allow filling of the intra-annular space with prosthetic material 408 as shown in FIG. 40D.

Figure 41:
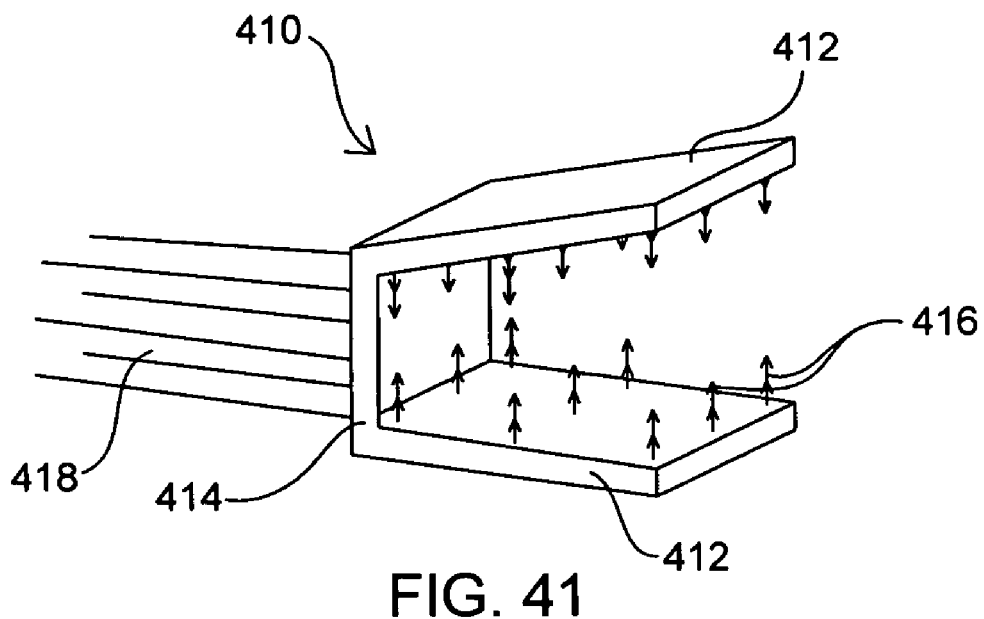
FIG. 41 illustrates another clamp embodiment of an augmentation device of the present invention.

FIG. 41 illustrates another clamp type disc augmentation device 410 which is an integrated variation of the tandem use of device 260 of FIG. 27. Device 410 has an endplate 414 and transversely positioned side plates 412 which collectively form a U-shaped configuration. A plurality of strands, sutures or filaments 418 extends from the outer side of endplate 414 and a plurality of barbed anchors 264 extend from the inside, facing surfaces of sidewalls 412. The delivery tool 270 of FIGS. 28A and 28B may also be used to implant device 410.

Figure 42A:
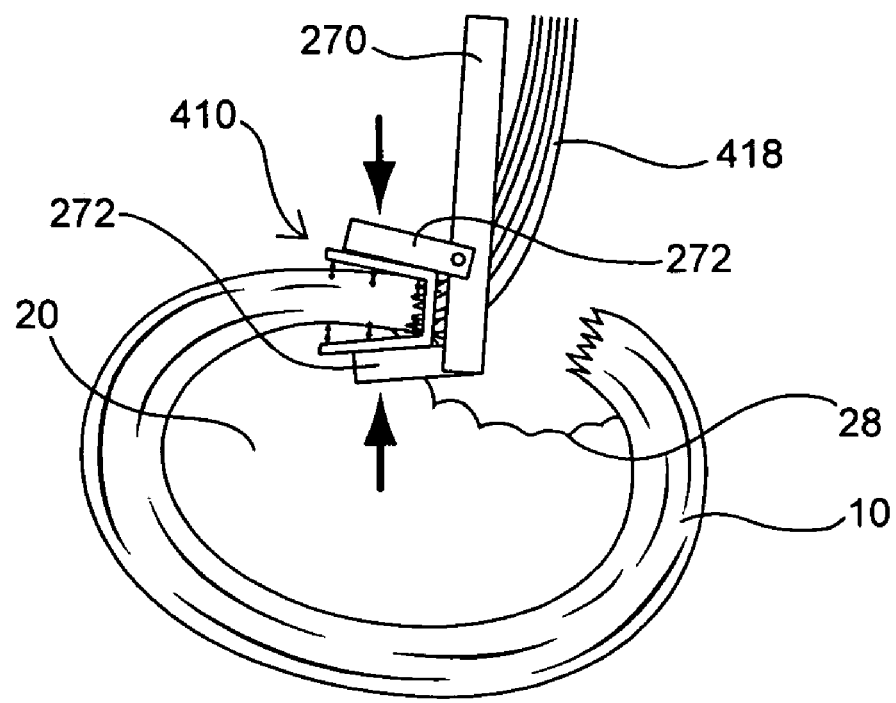
FIGS. 42A-42F illustrate various steps for implanting the disc augmentation device of FIG. 41 and for implanting a prosthetic material according to methods of the present invention.
Figure 42B:
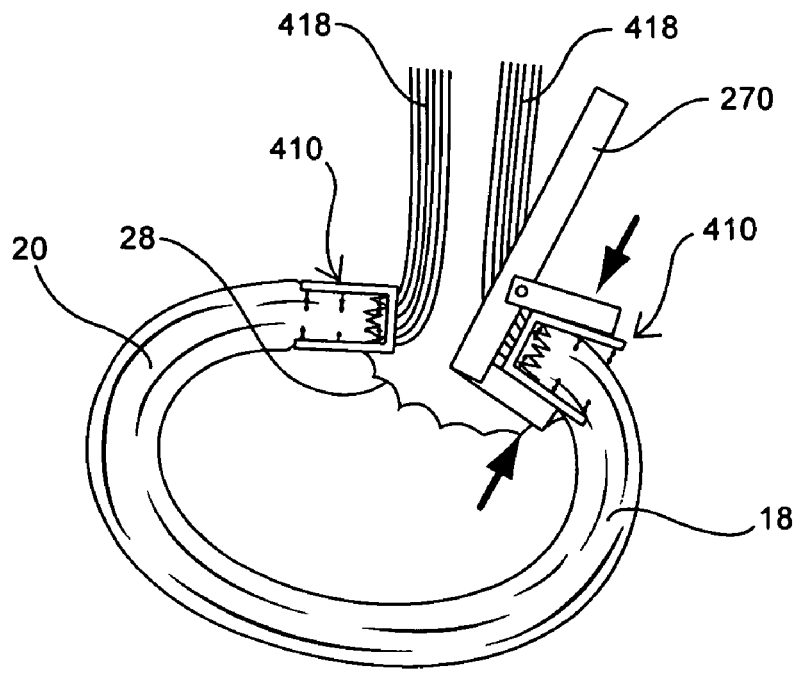
Figure 42C:
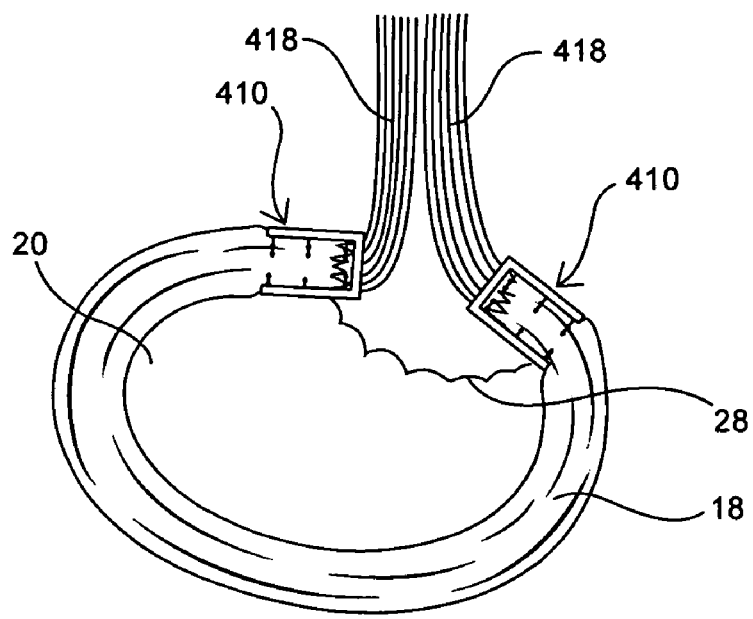
Figure 42D:
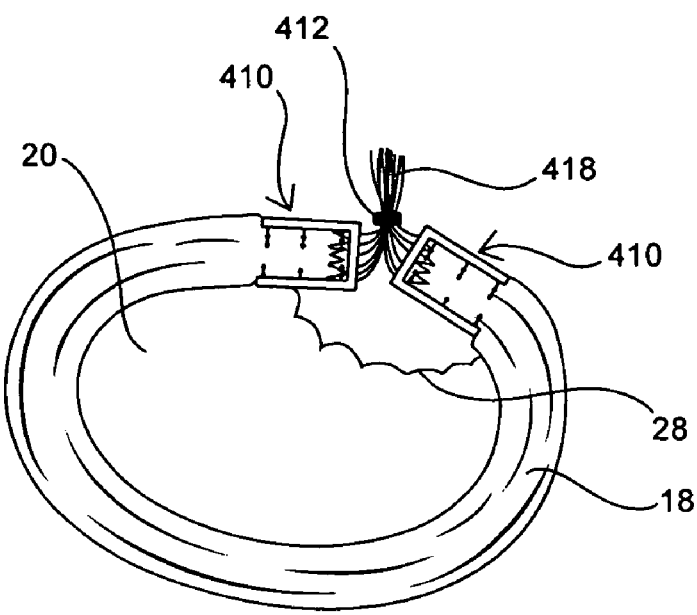
Figure 42E:
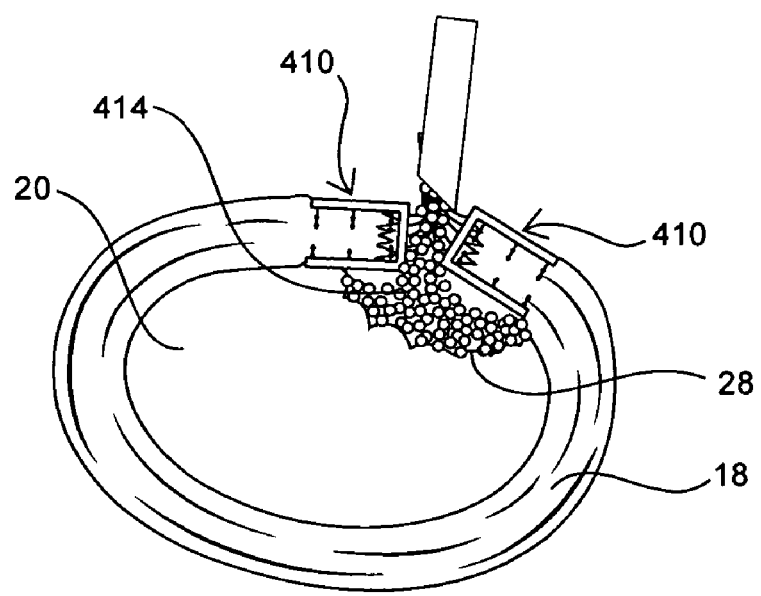
Figure 42F:
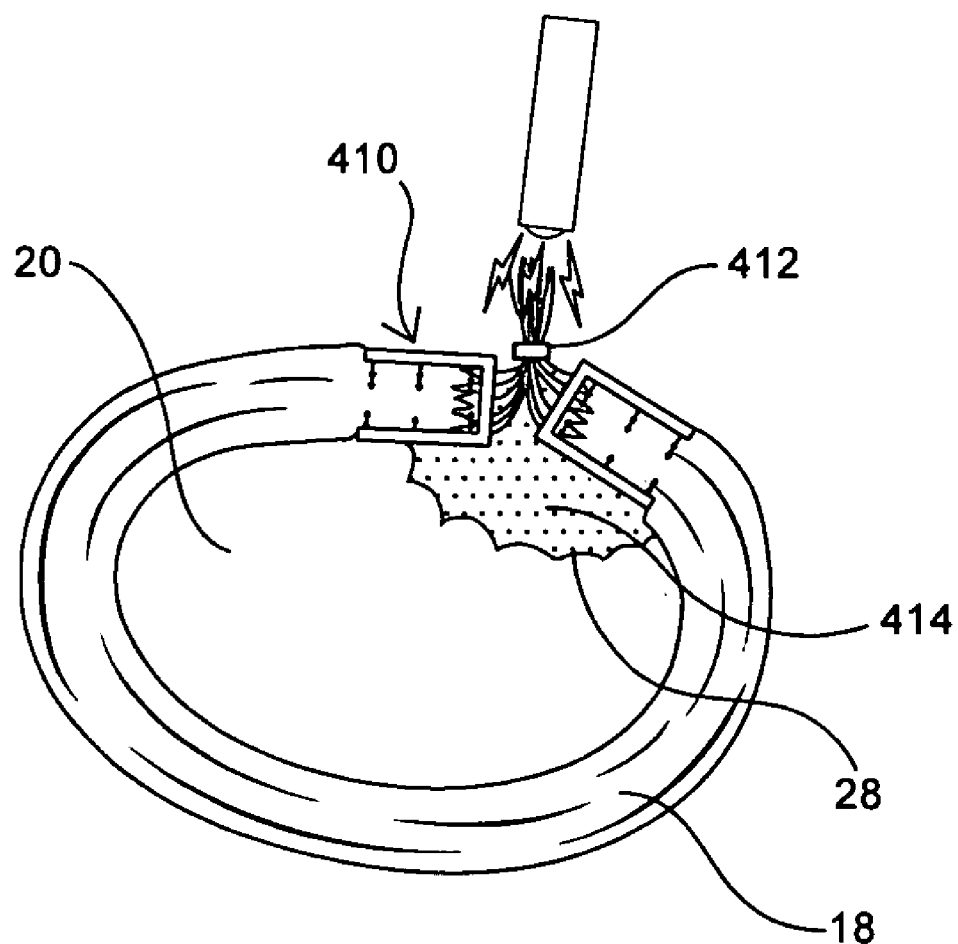

Referring to FIG. 42A, with device 410 seated between jaws 272, the distal end of tool 270 is positioned within defect 28 within annulus 18 such that a cut or free end of the annulus is sandwiched between sidewalls 412. Upon proper positioning, the jaws are compressed thereby driving anchors 416 transversely into the layers of the annulus 18. The process is repeated with a second device 410 being clamped to the opposing free end of annulus 18, as illustrated in FIGS. 42A and 42B. The trailing suture ends 418 of both devices 410 are synched and tied together by knot mechanism 412, thereby forming a scaffolding between implants 412, as illustrated in FIG. 42D. As described above, the scaffolding serves to augment the annulus and allows for passage of a prosthetic material 414 to within and throughout defect 28, as illustrated in FIG. 42E. After filling void 28, which may extend into nucleus 20, prosthetic material 414 is cured, as illustrated in FIG. 42F.

Figure 43A:
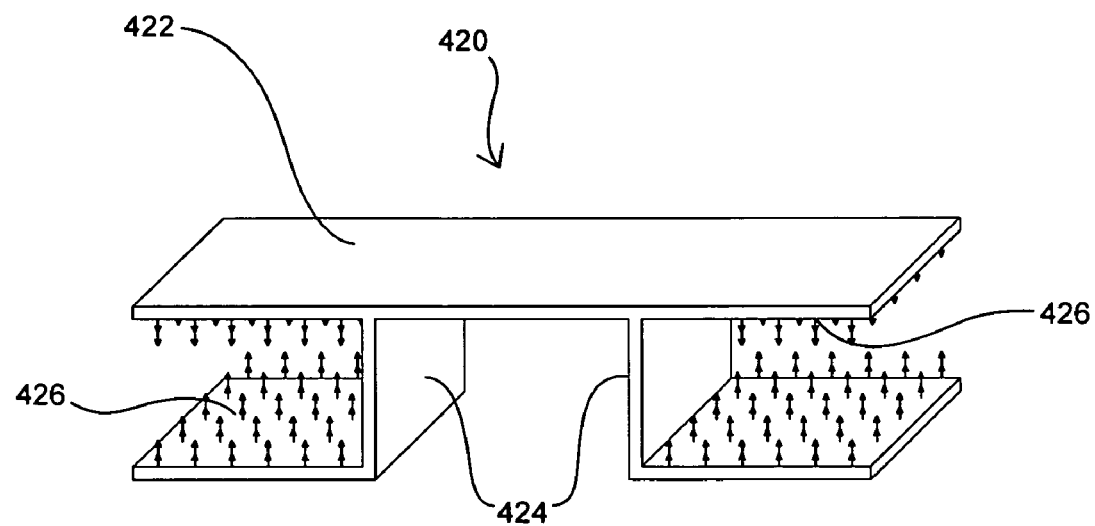
FIG. 43A illustrates another augmentation device of the present invention.
Figure 43B:
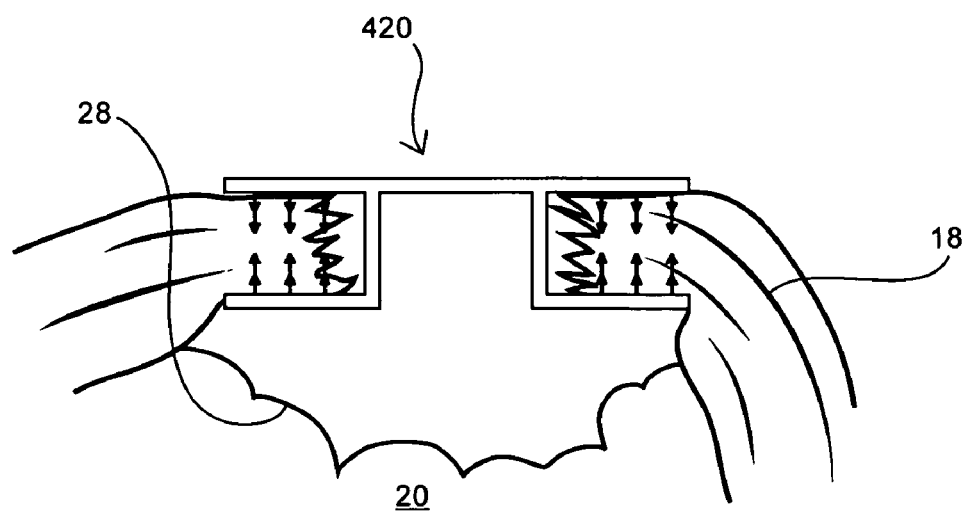
FIG. 43B illustrates the augmentation device of FIG. 43A operatively implanted within an intervertebral disc.

FIG. 43A illustrates another clamp embodiment of an implantable device 420 which includes bi-lateral integrated clamps 424 having U-shaped configurations (each similar to the clamp member of FIG. 41) which are bridged together on one side by bridge member 422. A plurality of barbed anchors 426 extend from the inwardly facing surfaces of the respective clamps 424. FIG. 43B illustrates device 420 operatively implanted within a disc defect 28 and bridging across the portion of the defect within annulus 18.

Figure 44A:
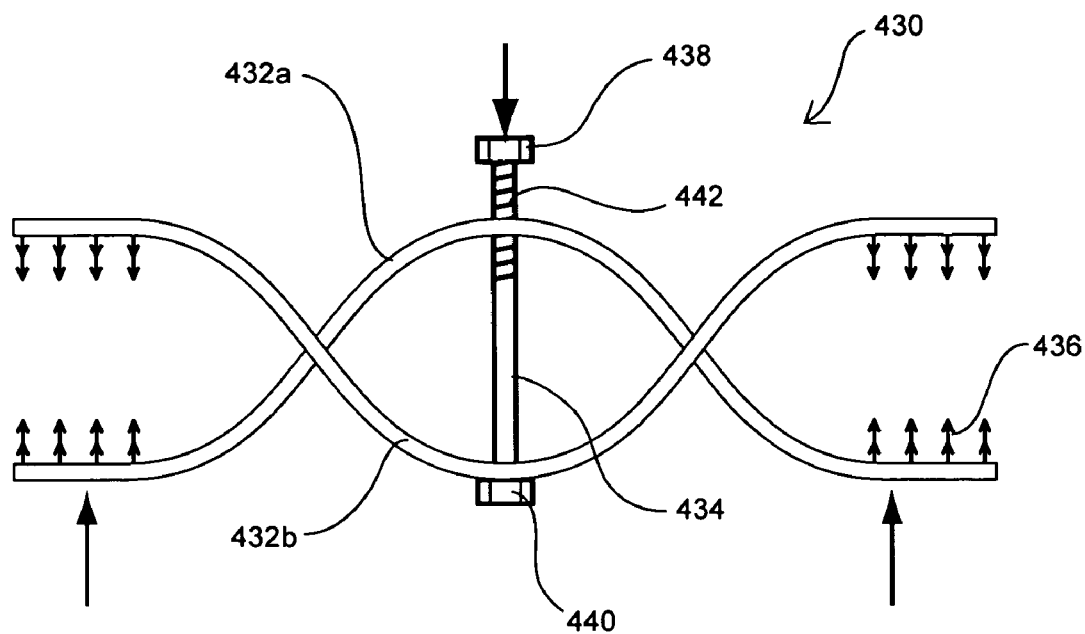
FIG. 44A illustrates another augmentation device of the present invention.
Figure 44B:
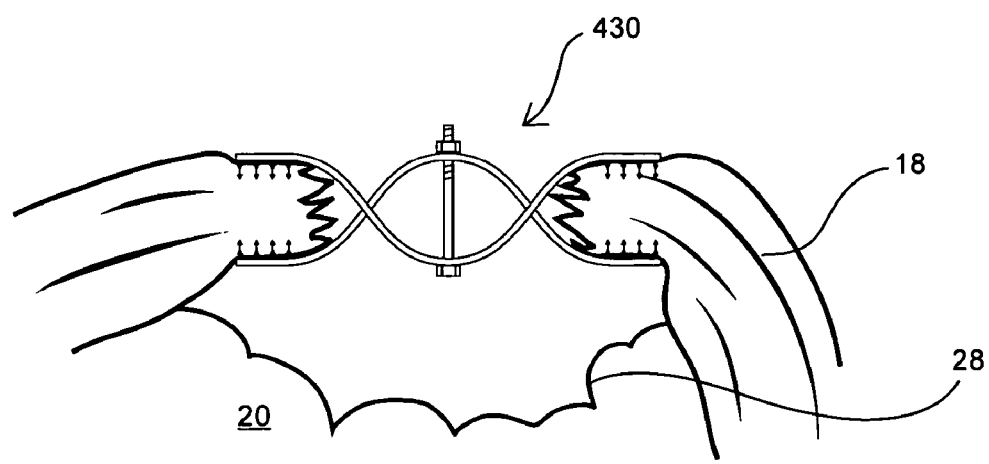
FIG. 44B illustrates the augmentation device of FIG. 44A operatively implanted within an intervertebral disc.

FIG. 44A illustrates another clamp embodiment of an implantable device 430 having two bowed plates 432a, 432b which are interlocked with each other by a core member 434 extending centrally between plates 432. The internally facing surfaces of the ends of plates 432 have barbed anchors 436. A fixed hub or nut 440 is mounted on the distal side of core member 434 and abuts the outside surface of plate 432. At the opposite end of core member 434 is a threaded hub or nut 438 which can be threaded along a threaded proximal portion 442 of core member 434. As hub 440 is threaded against plate 432a, the plates compress together. FIG. 44B illustrates device 430 operatively implanted within a disc defect 28 and bridging across the portion of the defect within annulus 18.

Figure 45A:
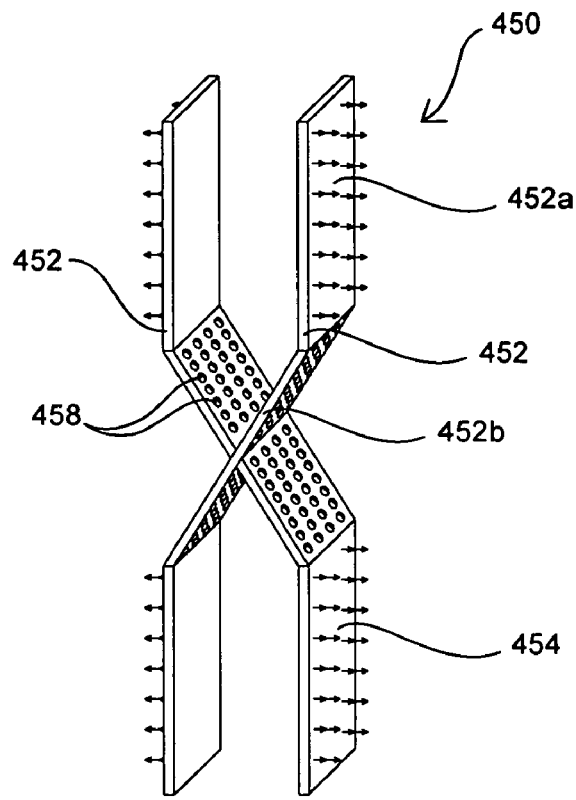
FIGS. 45A and 45B illustrate another clamp type augmentation device of the present invention in undeployed and deployed states, respectively.
Figure 45B:
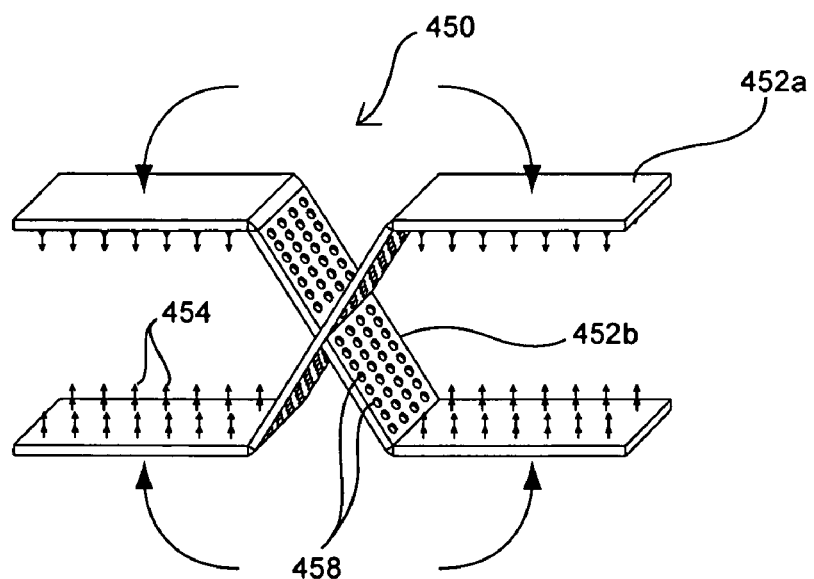

FIGS. 45A and 45B illustrate another clamp type embodiment of an augmentation device 450 which is self-clamping upon deployment. Device 450 includes two intersecting plates 452 each of which has two displaced parallel end portions 452a and a central portion 452b angled therebetween. Opposing sides of end portions 452a have a plurality of barbed anchors 454 extending therefrom and central portions 452b optionally have a plurality of apertures formed therein. Plates 452 are preferably made of a superelastic memory material whereby they can be inverted from a naturally biased or deployed state (FIG. 45B) to a spring-loaded or undeployed state (FIG. 45A) where device 450 obtains a low profile for minimally invasive delivery.

Figure 46C:
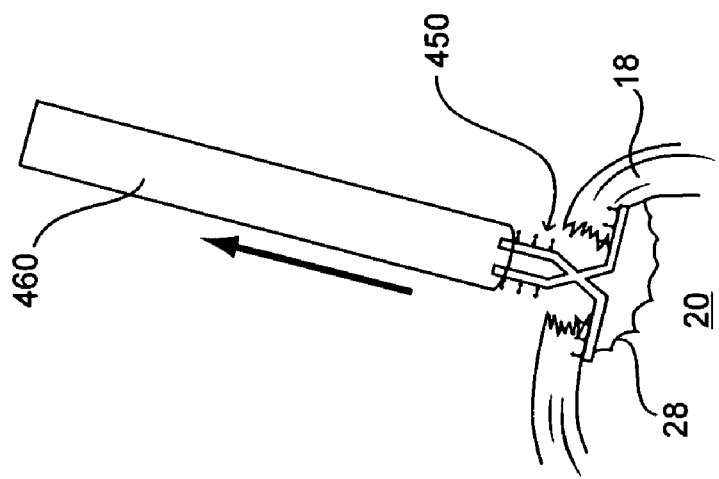
FIGS. 46A-46F illustrate various steps for implanting the disc augmentation device of FIGS. 45A and 45B and for implanting a prosthetic material according to methods of the present invention.
Figure 46B:
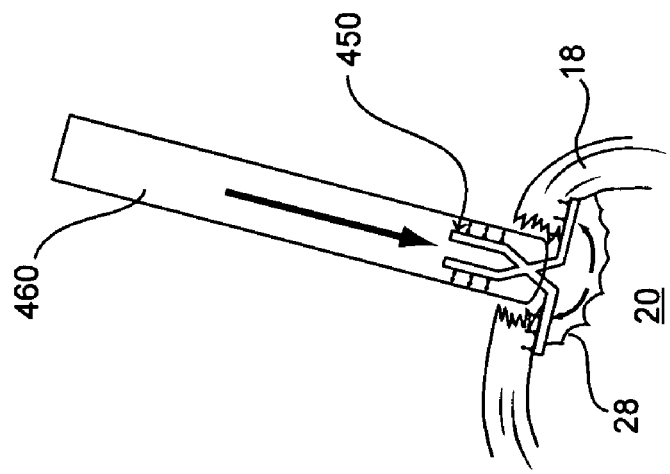
Figure 46A:
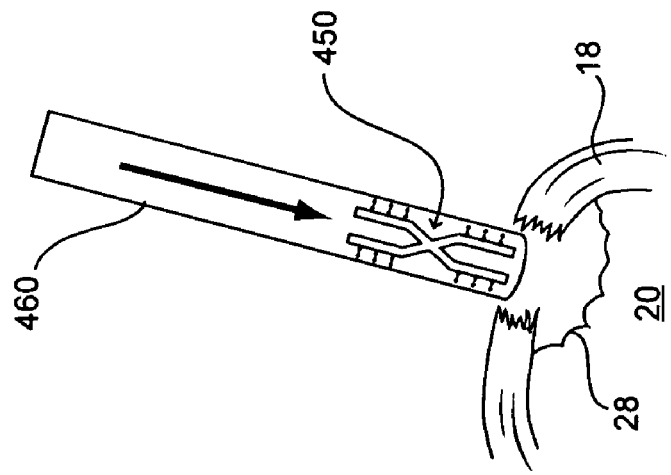
Figure 46F:
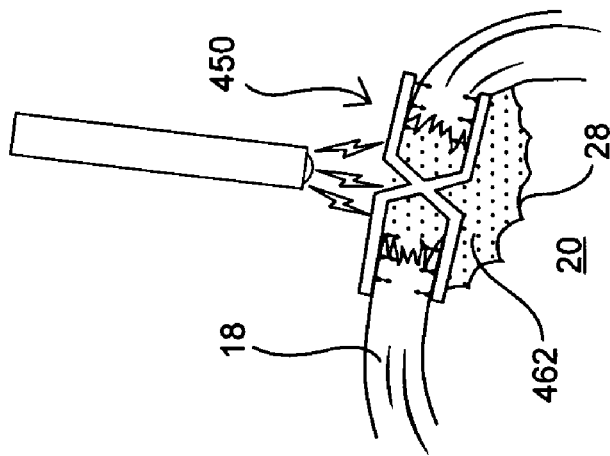
Figure 46E:
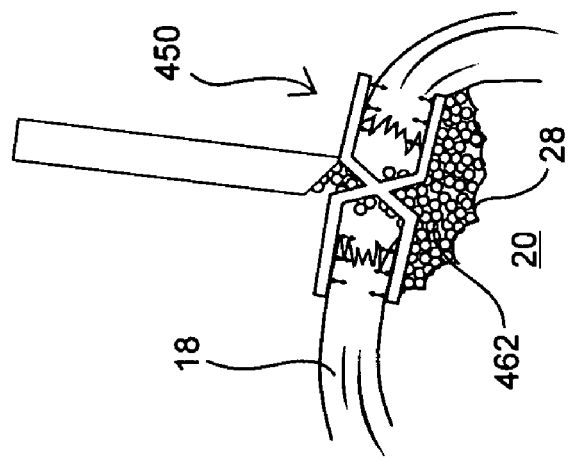
Figure 46D:
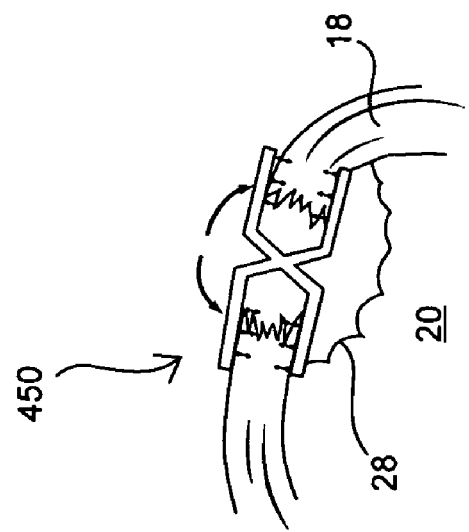

As illustrated in FIGS. 45A and 46A, in an inverted, low profile state, device 450 is deliverable through a cannula 460 to within a void or defect 28 within the annulus wall 18 anchors 454. As the distal end or pair of end portions 452b are advanced beyond the distal end of cannula 460, the spring-load of the inverted device forces distal end portions to spring apart from each other, as illustrated in FIG. 46B, and impinge upon the inner aspect of annulus 18, forcing anchors 454 to penetrate into the annulus wall. Cannula 460 is then removed from the site, as illustrated in FIG. 46C, thereby releasing the proximal end portions of device 450 which in turn allows them to impinge upon the outer aspect of annulus 18, as illustrated in FIG. 46D. The porous central portions 452b of device 450 allow for passage of a flowable prosthetic material 462 to within and throughout defect 28, as illustrated in FIG. 46E. After filling void 28, which may extend into nucleus 20, prosthetic material 462 is cured, as illustrated in FIG. 46F.

Figure 47A:
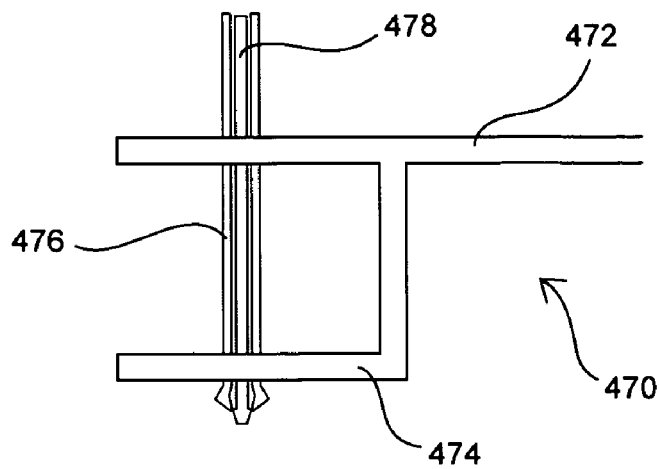
FIGS. 47A-47D illustrate another clamp type augmentation device of the present invention.
Figures 47B, 47C:
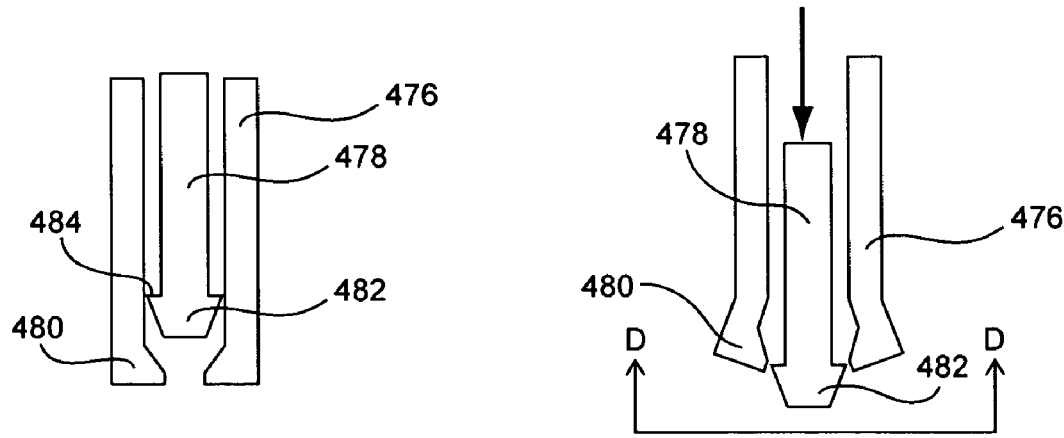
Figure 47D:
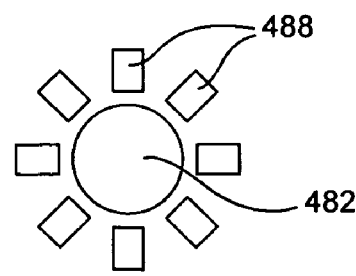

FIGS. 47A-47D illustrate another clamp type augmentation device 470 having annulus receiving portions or clamps 474 (only one side is shown) extending from a bridging portion 472. While clamp portion 474 may be deformable or compressible, it need not be as the clamp has holes (not shown) within its sidewalls for receiving a pin member transversely therethrough, as illustrated in FIG. 47A, by which to secure the device to tissue received within clamp portion 472. Pin member includes an outer sheath 476 and inner core 478 which is slidable within the lumen of sheath 476. The outer diameter of sheath 476 is sufficient such that it is receivable within the holes of the sidewalls of clamps 474 and the inner diameter of sheath 476 is tapered at a distal end 480 thereof. Inner core 478 has an enlarged distal end 482 which has a diameter which is equal to or less than the inner diameter of sheath 476 except at the tapered distal end 480, where the diameter of end 482 is greater than that of the inner diameter of the tapered distal end portion 480. Outer sheath 476 is splittable at one or more circumferential locations along at least a distal portion of its length against the outward radial force exerted on the distal portion when inner core is driven therethrough. Here, sheath 476 is splittable into a plurality of petals 488 as illustrated in the end view of FIG. 47D. Enlarged distal end 482 has a proximal shoulder 484 which engages against petals 488 to resists against removal of core 478 from outer sheath 476.

Figure 48:
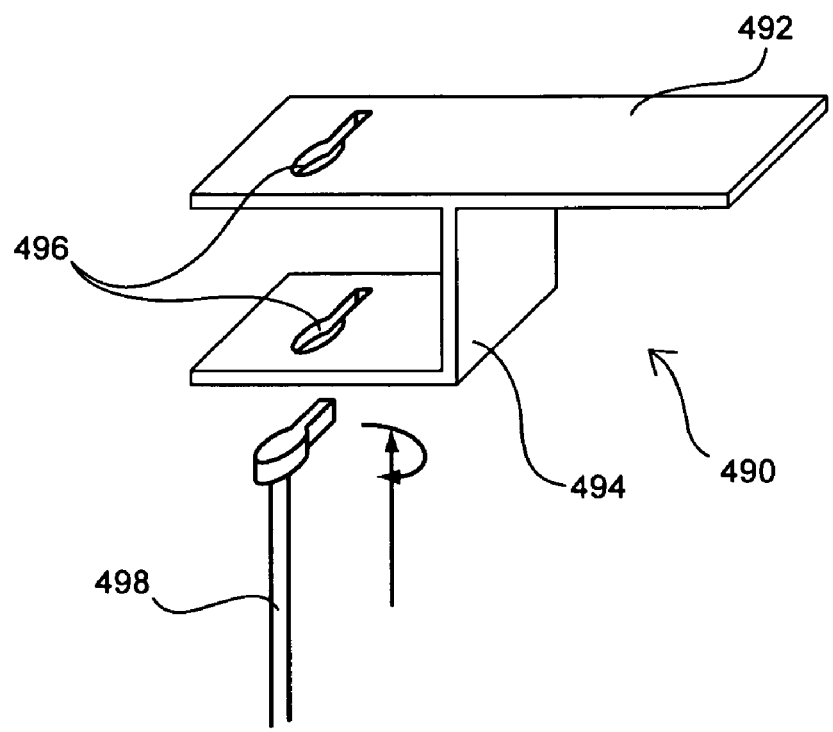
FIG. 48 illustrates yet another clamp type augmentation device of the present invention.

The augmentation device 490 of FIG. 48 has a configuration similar to that of device 470 of FIGS. 47A-47D with the difference being that the apertures 496 within the sidewalls of clamp portion 494 have a keyed configuration which correspond to the profile of a key 498. After passage of key 498 through the second sidewall, it can be turned about its axis and locked against the outer surface of the side wall.

Figure 49A:
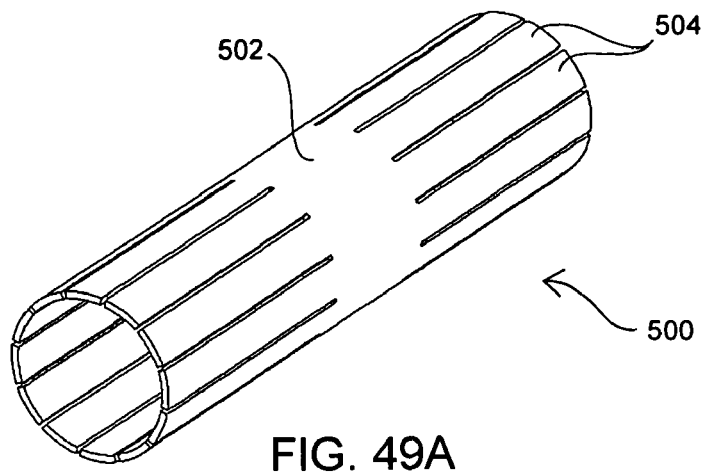
FIGS. 49A-49C illustrate several cylindrical clip type augmentation devices of the present invention.
Figure 49B:
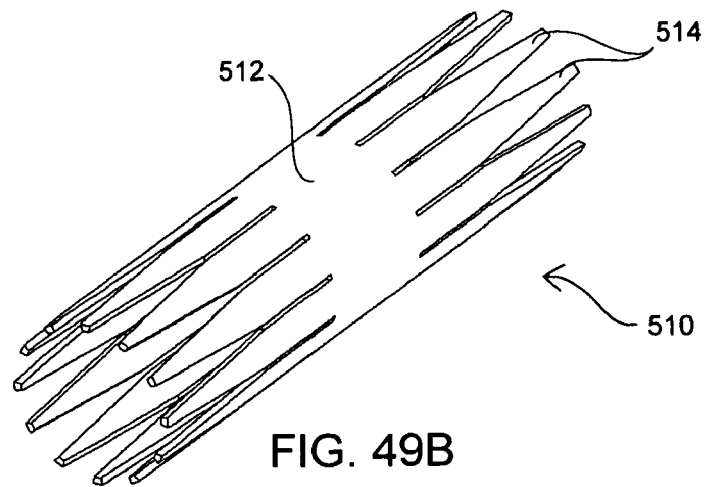
Figure 49C:
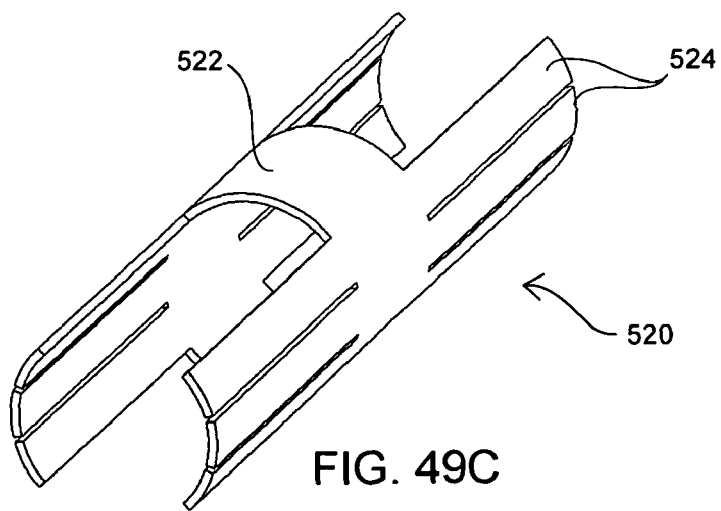

FIGS. 49A-49C illustrate other embodiments of augmentation devices 500, 510 and 520, respectively, of the present invention having a cylindrical or tubular configuration. Each device has a central portion 502, 512 and 522, respectively, from which a plurality of deformable or flexible fingers or petals 504, 514 and 524, respectively, extend on both sides of the central portion. Petals 504 of device 500 extend about its entire circumference, each having a rectangular configuration. Petals 514 of device 510 also extend about the entire circumference of device 510; however, the petals have a tapered tip. Petals 524 have a rectangular configuration and extend around only about half of the circumference of device 520 where about half of the plurality of petals is positioned opposite the other half.

Figure 50A:
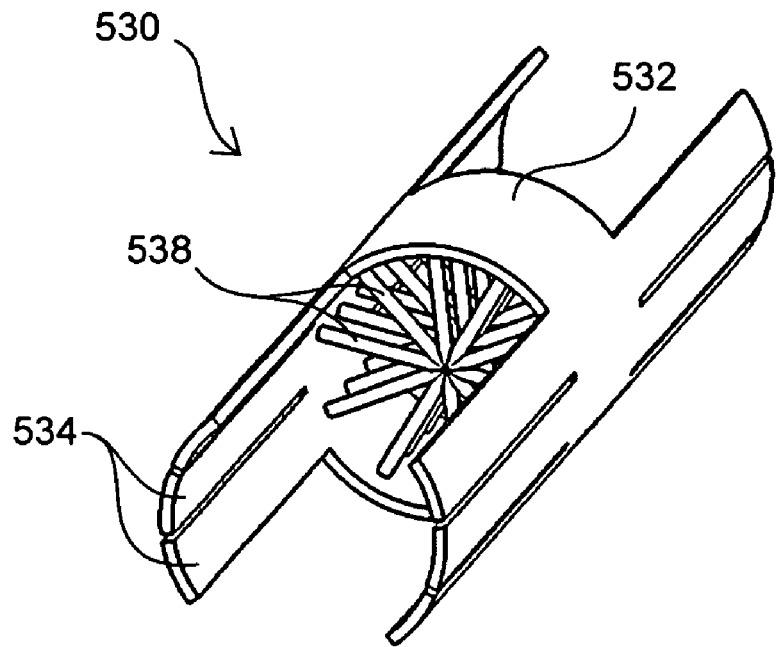
FIGS. 50A and 50B illustrate perspective and end views, respectively, of another cylindrical clip type augmentation device of the present invention.
Figure 50B:
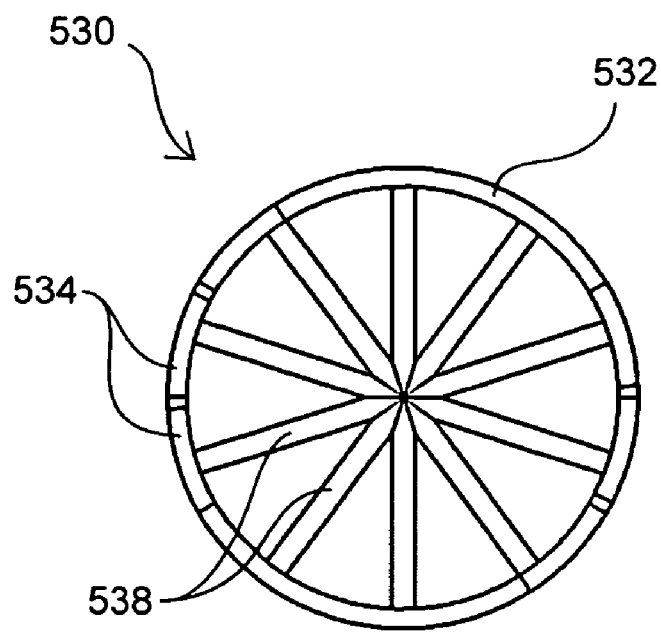

FIGS. 50A and 50B illustrate another cylindrical embodiment of an augmentation device 530 having a similar configuration to that of device 530 of FIG. 49C, i.e., a central portion 532 and a plurality of deformable or flexible fingers or petals 534 in two oppositely positioned sets. Additionally, device 530 includes a scaffolding structure within the lumen defined by central portion 532. Scaffolding structure includes one or more layers of a plurality of diametrically extending members or struts 538, but may have any configuration including any of the scaffolding configurations, e.g.; a plate with apertures, as described above.

Figure 51A:
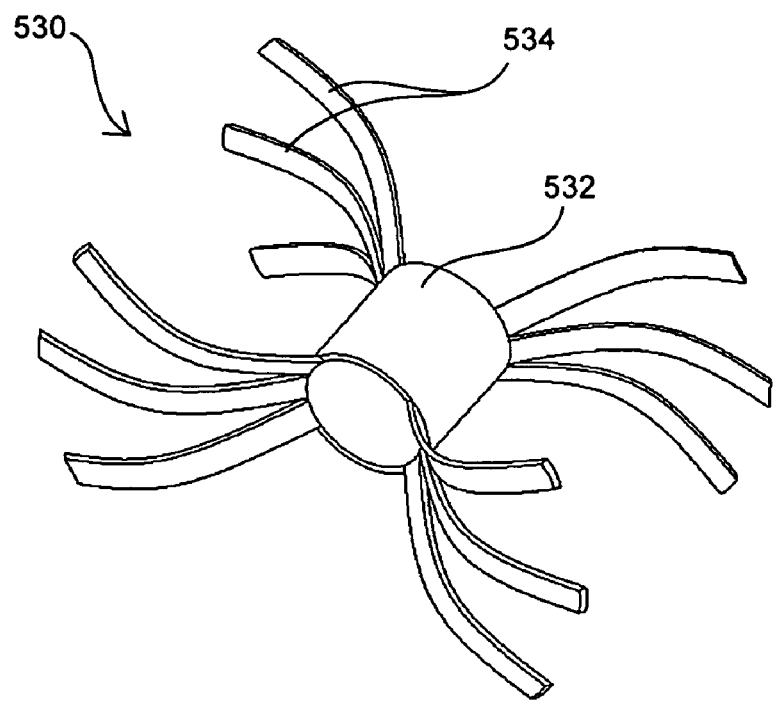
FIGS. 51A and 51B illustrate operative deformation of the device of FIGS. 50A and 50B upon implantation.
Figure 51B:
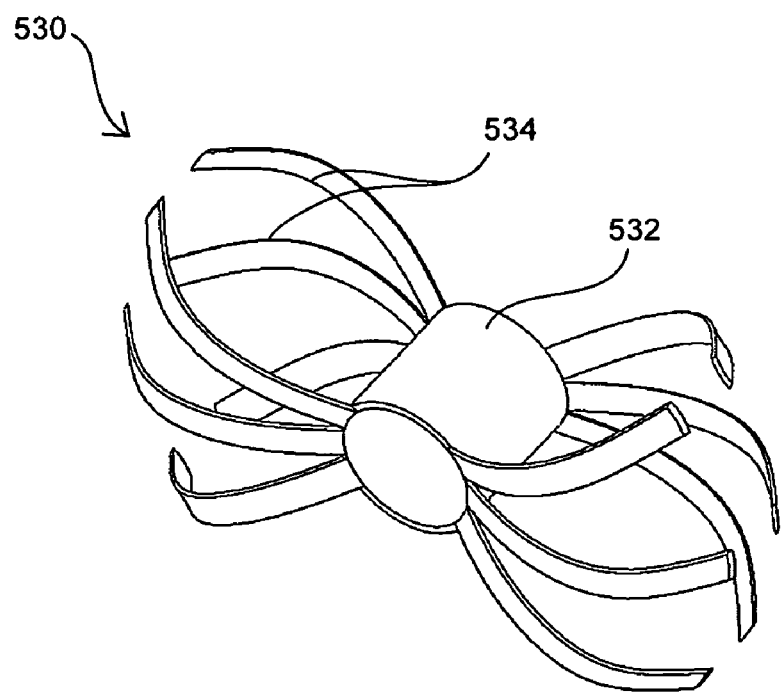

As illustrated in FIGS. 51A and 51B with respect to device 530, but which is also exemplary of each of the illustrated cylindrical clip embodiments, each set of petals 534 is deformable or malleable radially outward from central portion 532 towards the set of petals positioned at the opposite but same side of central portion 532.

Figure 52A:
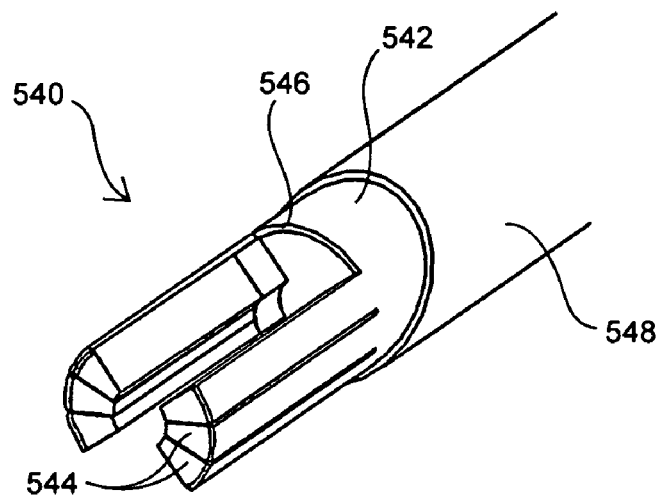
FIGS. 52A-52G illustrate various steps for implanting another cylindrical type disc augmentation device of the present invention.
Figure 52A:
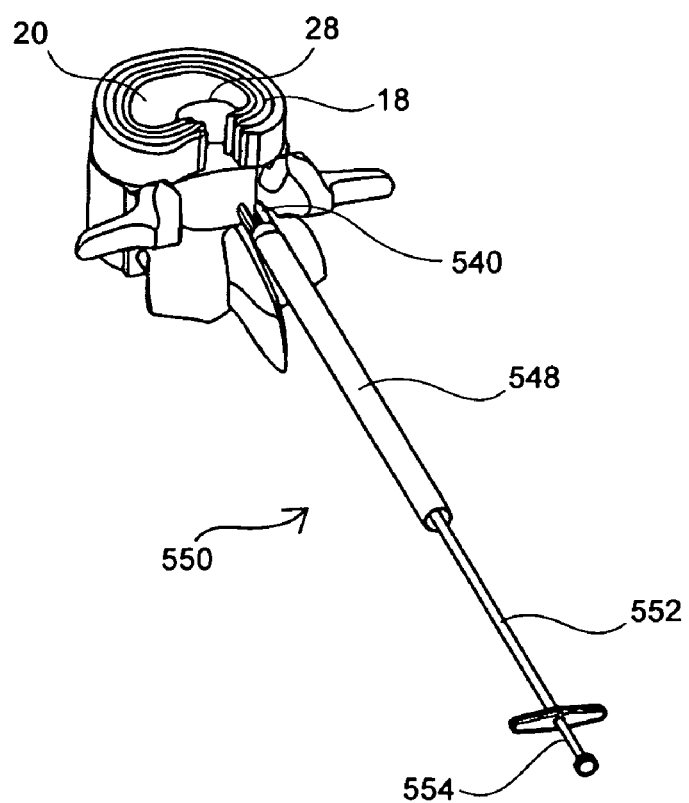
Figure 52B:
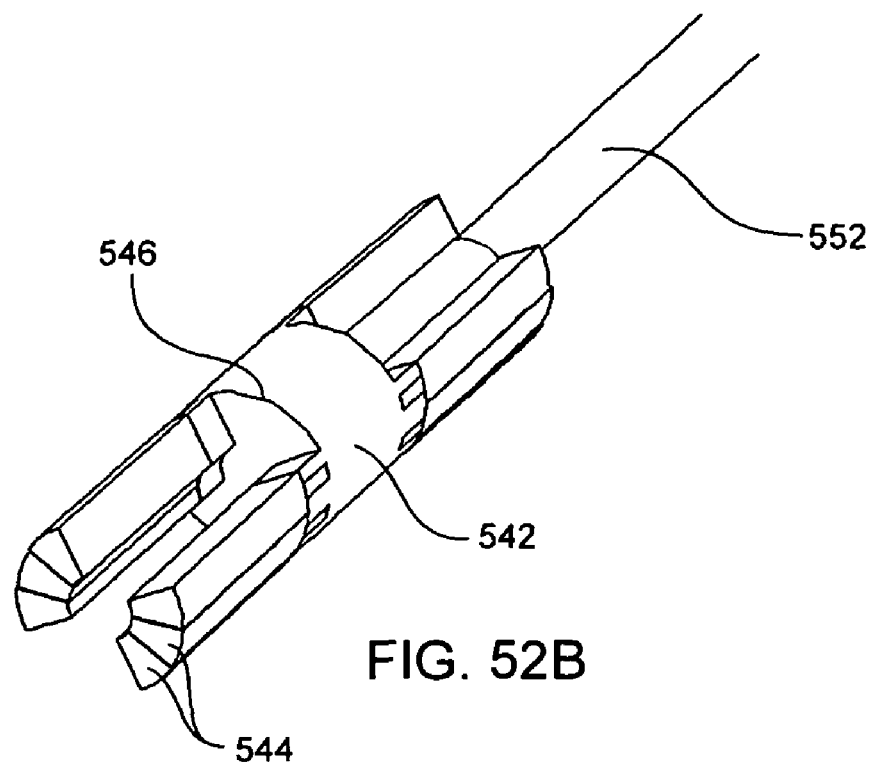
Figure 52B:
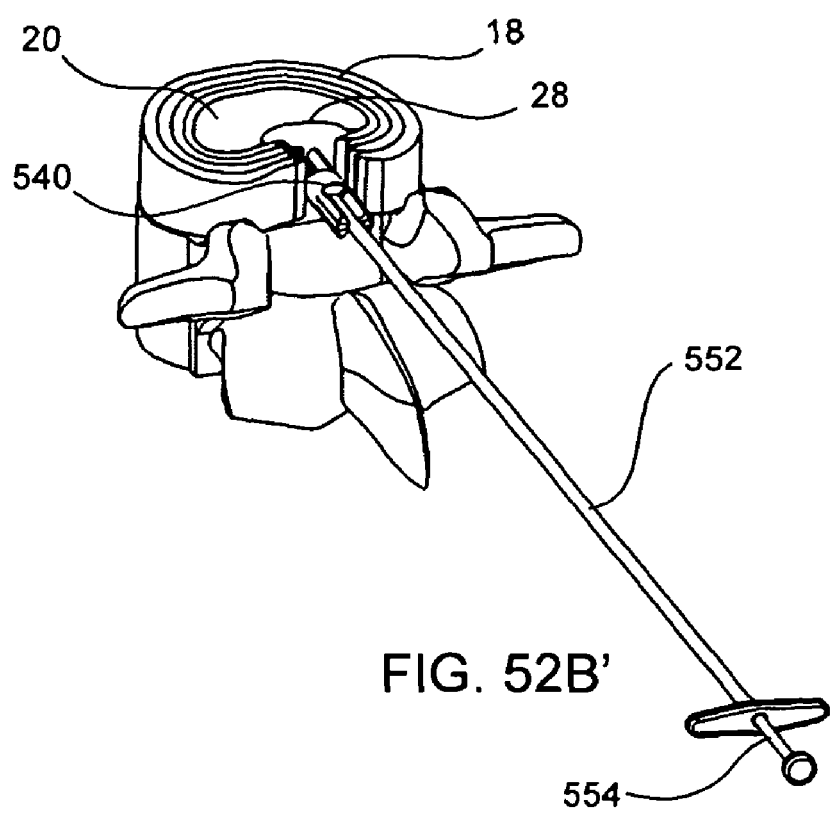
Figure 52C:
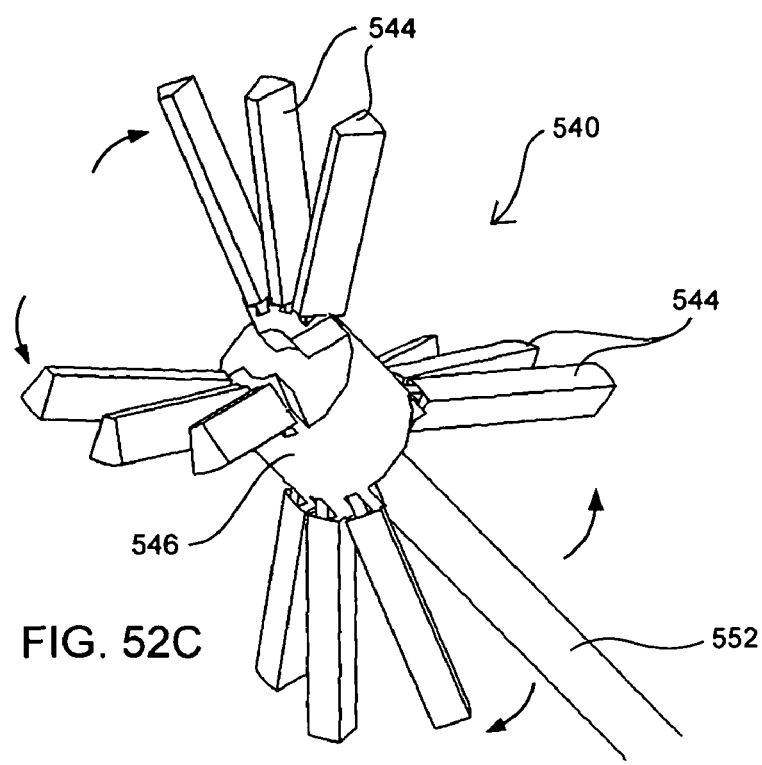
Figure 52C:
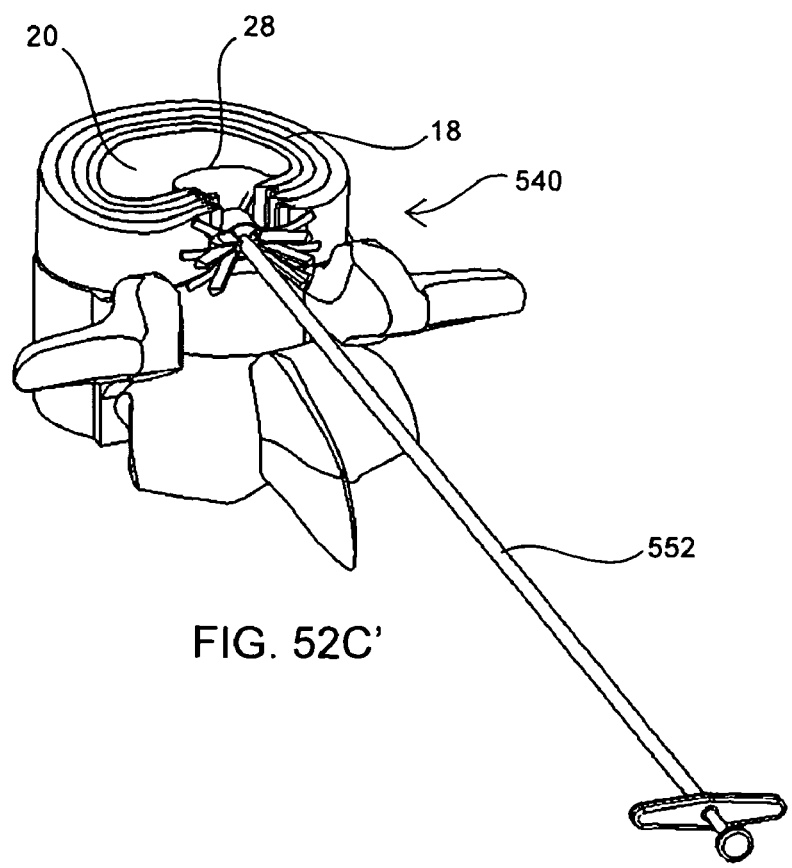
Figure 52D:
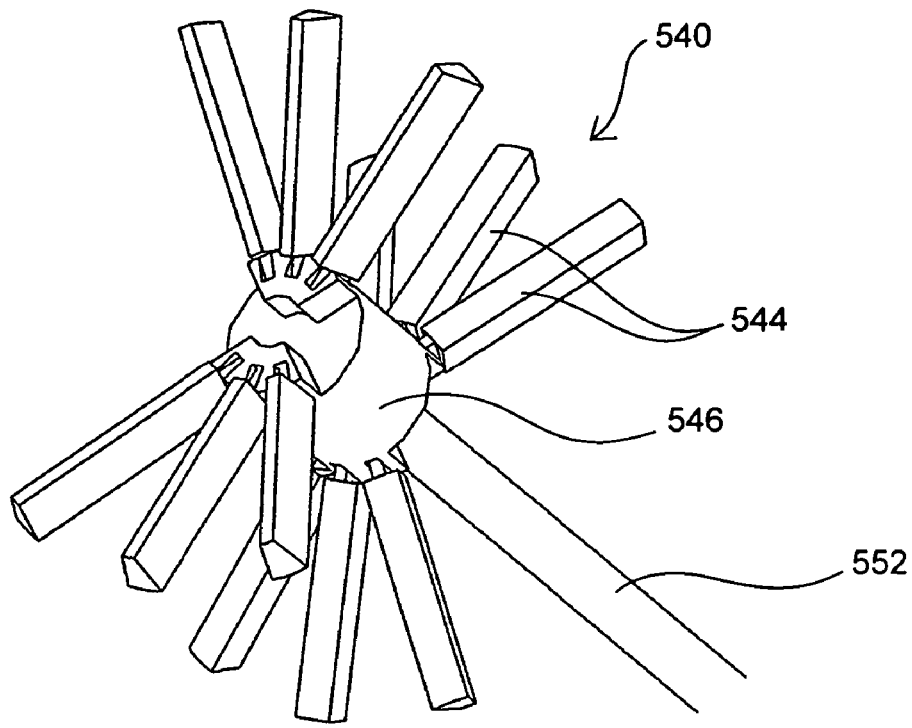
Figure 52D:
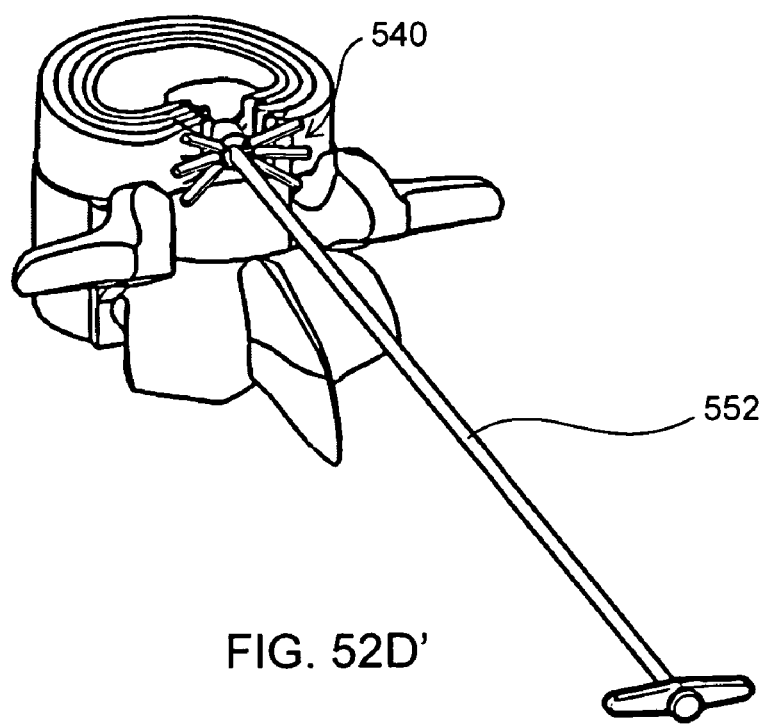
Figure 52E:
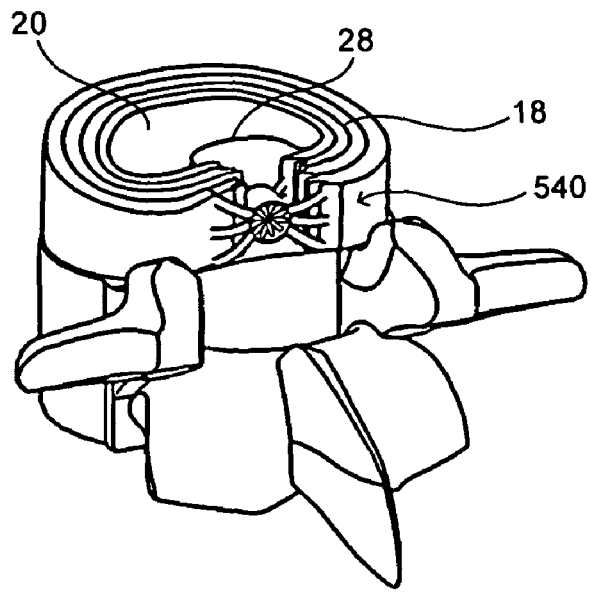
Figure 52F:
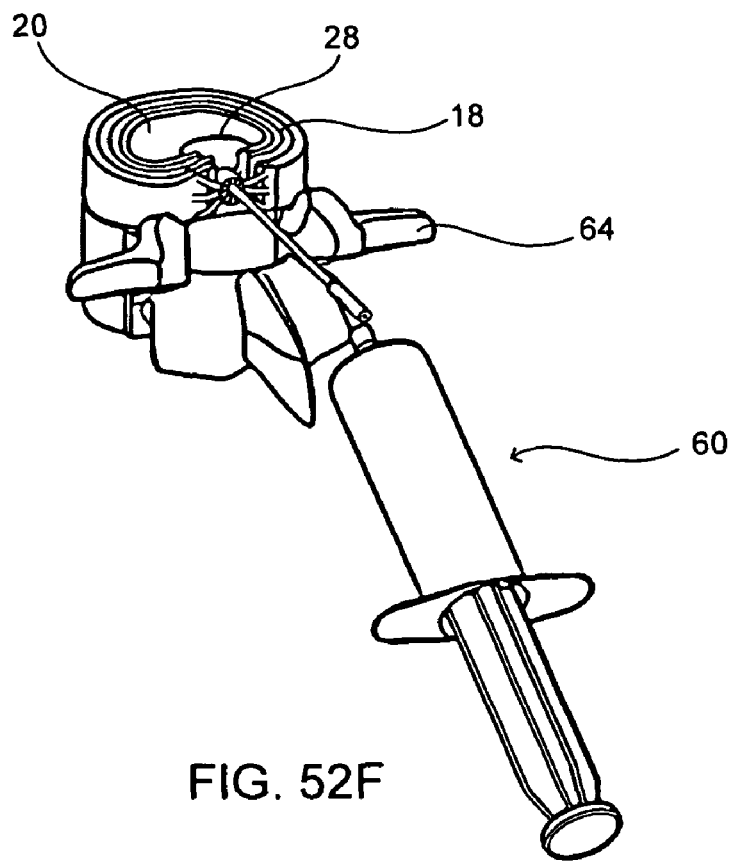
Figure 52G:
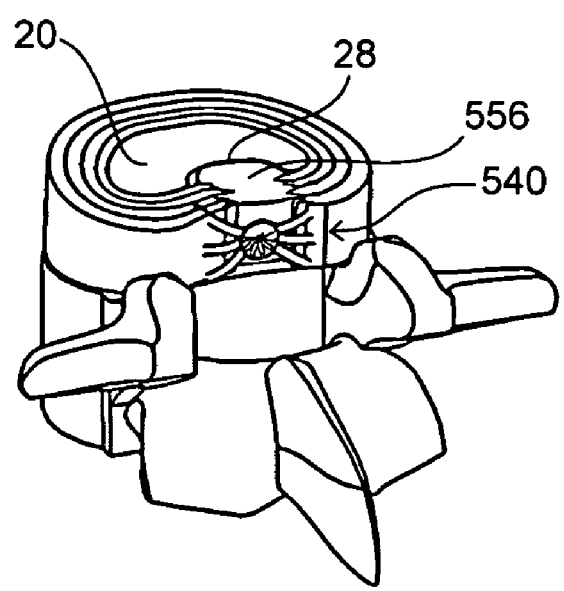

A step-by-step implantation procedure of another cylindrical augmentation device 540 of the present invention is provided in FIGS. 52A-52F. Device 540 has a configuration similar to that of device 530, having central portion 542 and two sets of a plurality of fingers 544 separated by spaces 546. As illustrated in FIGS. 52A and 52A', in an undeployed, low profile state, device 540 is advancable to an implant site through a cannula 548 by a detachable pusher member 552. Extending within pusher 552 is a finger deployment actuator rod 554. Upon positioning device 540 within the implant site, i.e., void 28 within annulus 18, cannula 548 may be removed, as illustrated in FIGS. 52B and 52B'. Actuator rod 554 is then actuated to commence deployment of fingers 554, as illustrated in FIGS. 52C and 52C', and continue deployment until fingers 554 achieve a locked position and fully embrace both free ends of annulus 18 therebetween, as illustrated in FIGS. 52D and 52D'. Upon full deployment, pusher mechanism 552 is released from core 542 leaving device 540 within the disc defect, as illustrated in FIG. 52E. As described above, an injector tube 64 is positioned within the scaffolding within device 540 and prosthetic material 558 is injected therein and subsequently cured as illustrated in FIGS. 52F and 52G.

Figure 53A:
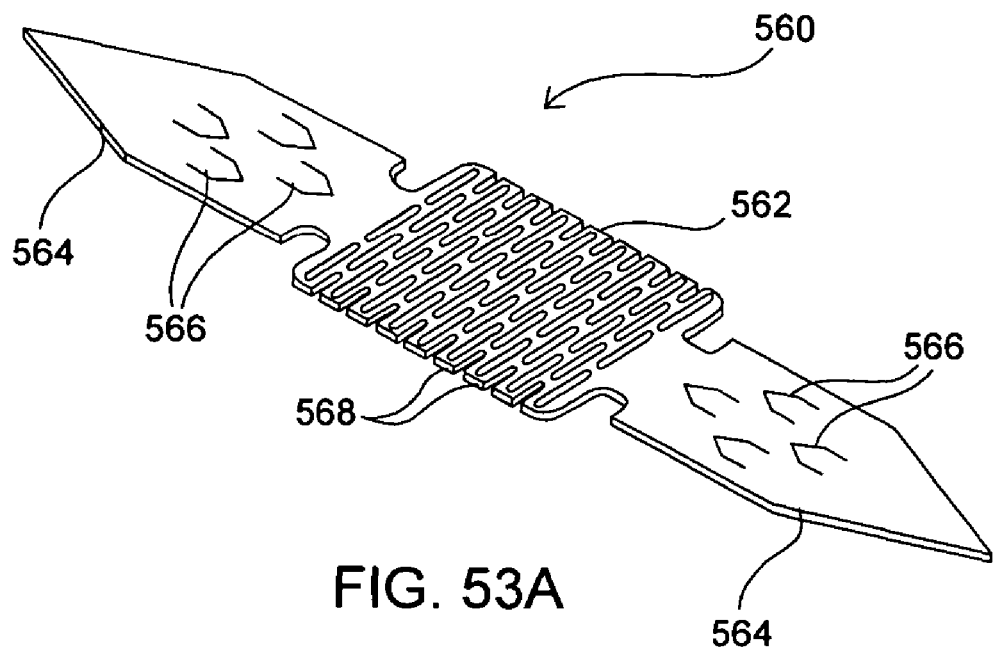
FIGS. 53A and 53B illustrate two other disc augmentation devices of the present invention which can be made of a super elastic or shape memory material in order to undergo a change in configuration upon implantation.
Figure 53B:
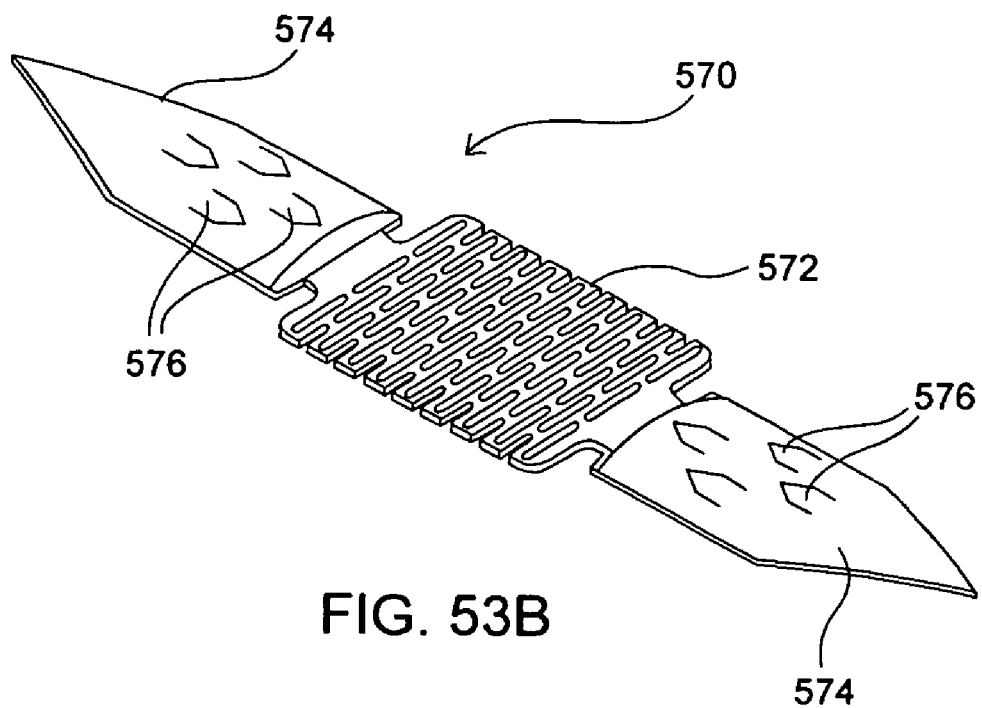

FIGS. 53A and 53B illustrate two other disc augmentation devices of the present invention configured for implantation within an intra-annular space which are similar in structure to the device of FIGS. 3A-3D and may be made of the same or similar materials (e.g., shape memory or super elastic) and fabricated in the same or similar manner. Devices 560 and 570 of FIGS. 53A and 53B, respectively, each have a thin planar structure having a central portion 562, 572 flanked by end portions 564, 574. The central portions have a grid or screen or other fenestrated configuration having a plurality of openings or apertures 568, 578. Alternatively, the central portion may have an open cell construction where one or more filaments are used to create such. The openings are sized to facilitate in growth of tissue and the passage of native fluids therethrough and/or to allow for the passage of a flowable implant material as mentioned above, yet able to retain an implant material within the nucleus, i.e., upon curing of a flowable material or immediately with a solid or highly viscous material. As such, the opening sizes may be in the ranted from about 0.1 to about 1.6 mm or may be greater or smaller depending on the viscosity and/or size of the implant material. Further, in addition to being bendable (due to shape memory characteristics), the central portions may be somewhat compliant or flexible such that they "give" a bit (i.e., radially) under normal physiological and physical conditions undergone by an intervertebral disc.

Each end portion 564, 574 has one or more laterally extendable anchors 566, 576 as described above and tapered or sharpened ends to facilitate atraumatic entry between lamellae within the annulus. The end portions 564 of device 560 of FIG. 53A have a flat configuration while end portions 574 of device 570 of FIG. 53B have slightly raised rounded, domed or convex surfaces on the side of the device which is to face outward when implanted into a disc annulus so as to provide a more conforming fit within the annulus as well as to enhance the stiffness of the end portions to facilitate their penetration into the annular implant site. In some embodiments, both sides of the end portions may have such a raised configuration.

Figure 54A:
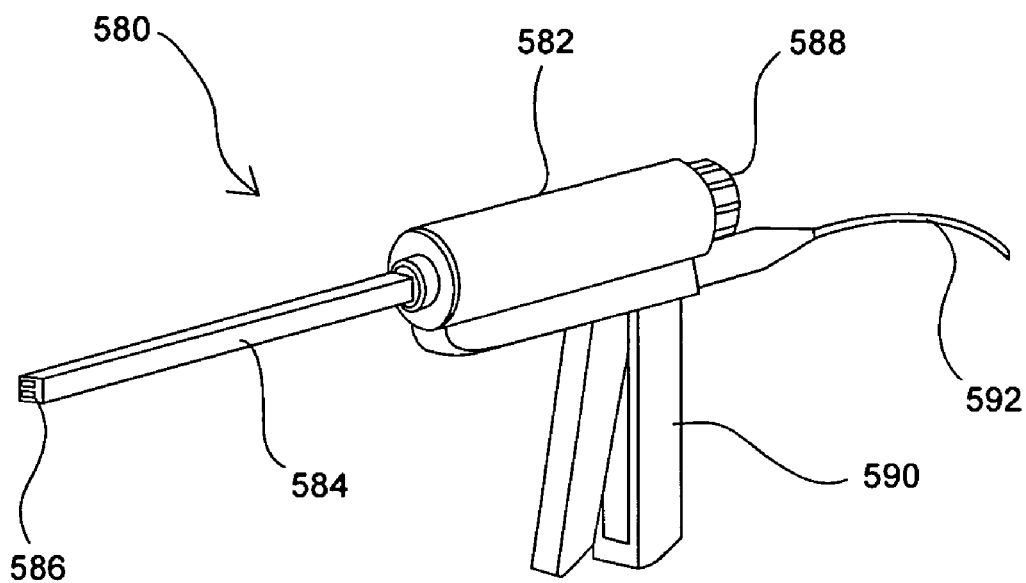
FIGS. 54A-54D illustrate a tool for the delivery and implantation of certain augmentation devices of the present invention which devices can be provided within a preloaded cartridge for use with the tool.
Figure 54B:
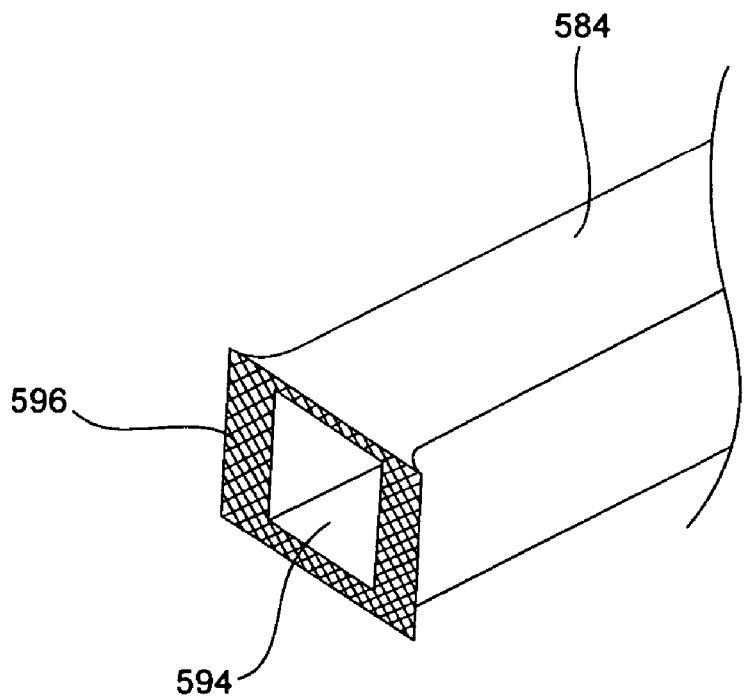
Figure 54C:
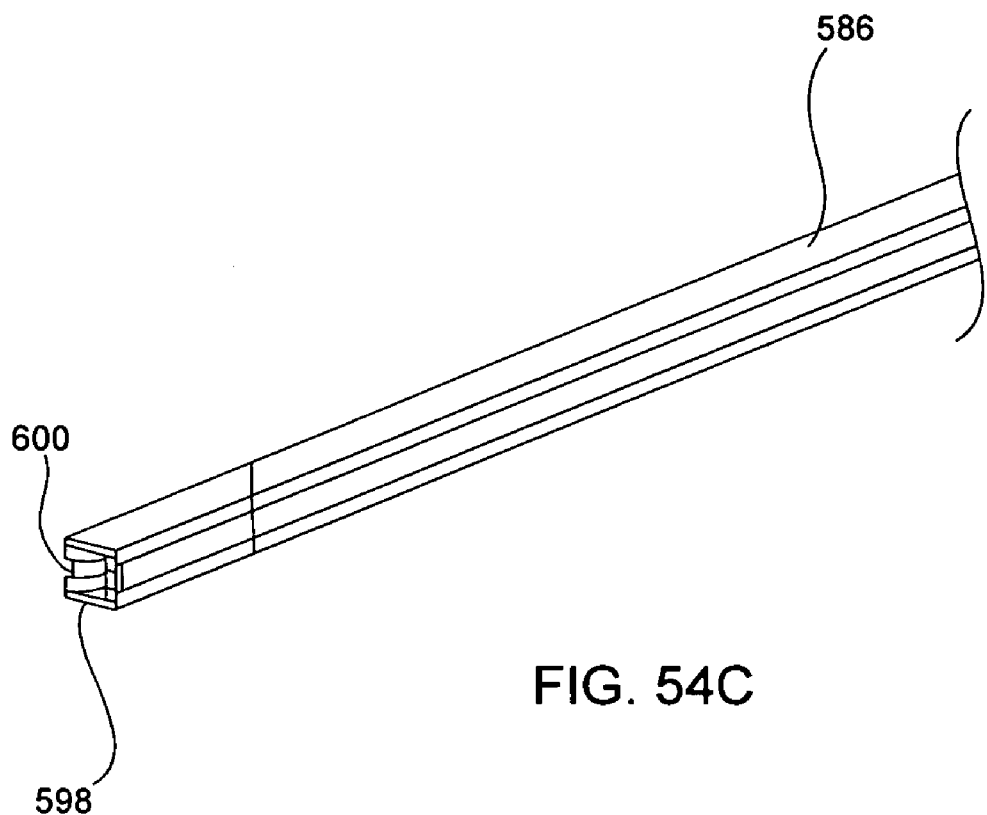
Figure 54D:
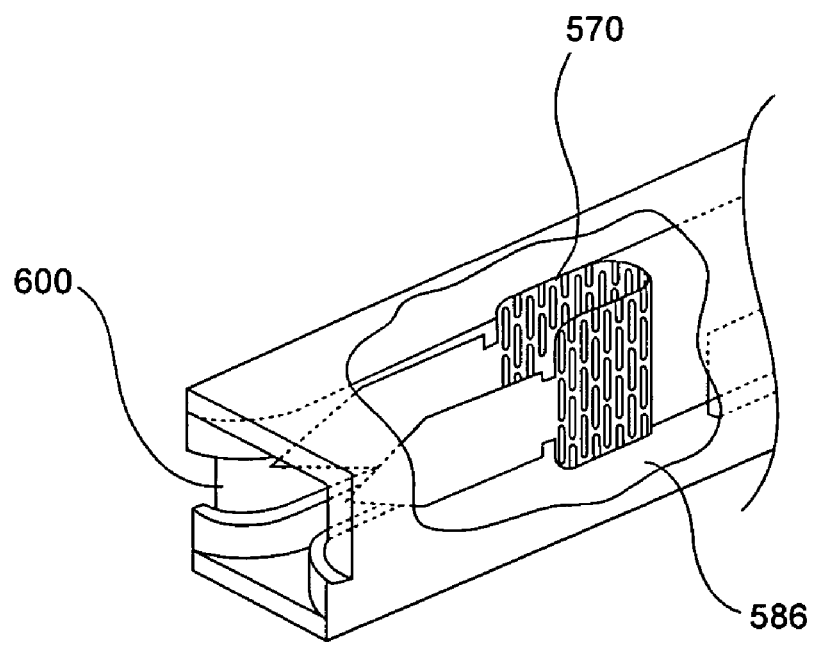

The just described implantable disc augmentation devices as well as certain other embodiments of the augmentation devices (such as those described with respect to FIGS. 3A-3D and 5A and 5B) are deployable within an intervertebral disc with the delivery tool 580 of FIGS. 54A-54D. Tool 580 has a body portion 582 and an elongated sheath 584 extending distally therefrom. Elongated sheath 584 defines an open lumen 594 for receiving a magazine or cartridge 586 of preloaded augmentation devices 570 provided in a stacked or sequential arrangement. The distal end 596 of sheath 584 may have a flared configuration to provide footing against the outer surface of the annulus and thereby stabilize the tool during use. At least the distal portion of the internal side walls of cartridge 586, as best illustrated in FIG. 54D, may be configured, e.g., grooved, to facilitate the tracking of each augmentation device 570 therethrough. The distal portion 600 of the internal side walls are preferably ramped or flared to facilitate transition of augmentation device 570 from a compressed low profile (as shown in FIG. 54B) to an expanded configuration upon implant.

Body portion 582 houses mechanical components and gear mechanisms for effecting manually actuated actions, e.g., the turning of knob 588 for securing cartridge 586 within shaft 584 and the pumping of handle mechanism 590 for advancing the one or more preloaded augmentation devices through cartridge 586, such as by a rod 610 (see FIGS. 56B and 56C), and expelling them therefrom. Of course, delivery tool 580 may be equipped with any number of mechanisms for effecting mechanical actions. Additionally, tool 580 may be adapted to provide heat energy, such RF energy, by way of a connection 592 to an energy supply. In this way, the tool can be used to heat the annulus tissue into which the augmentation device is implanted for purposes of denervating the tissue and/or shrinking the collagen within the tissue about the implant so as to ensure its placement therein as well as to facilitate closure of the defect. Further or alternatively, the heat energy may be used to heat the temperature of the implanted augmentation devices or portions thereof, such as the end portions, to transition them to their preshaped configuration which, in certain embodiments, will cause them to bend radially inward (or outward if desired) and penetrate the annulus tissue thereby preventing migration from the implant site.

Prior to implantation of one or more intra-lamellar devices 570 (or the like), the depth or thickness of the annulus may be measured to determine an optimal depth for implanting the device(s), as well as the number of devices if more than one is being used. While in many circumstances, one device 570 is sufficient to achieve the desired augmentation and repair of the disc defect, any number of such devices may be used. For example, the thicker the annulus, the more devices that may be required.

Figure 55A:
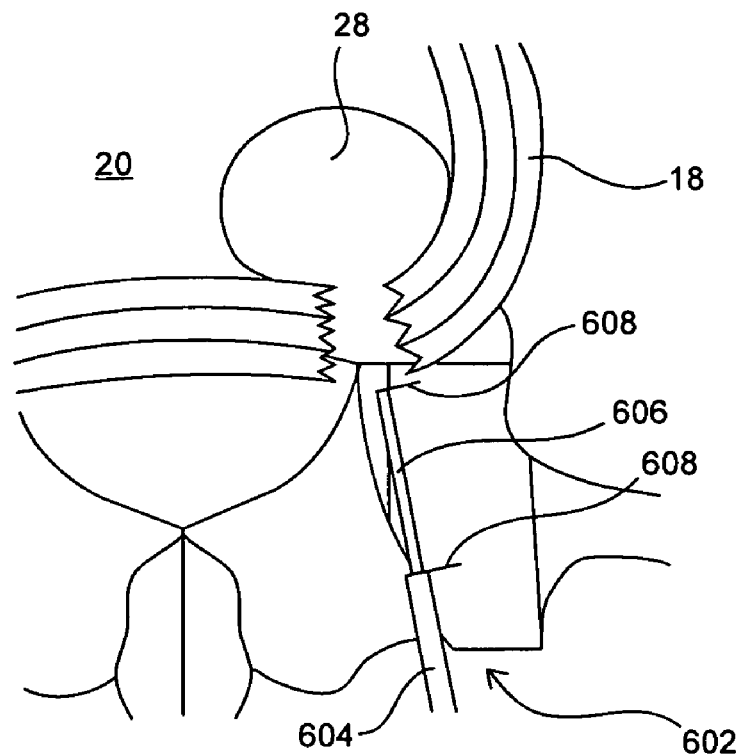
FIGS. 55A and 55B illustrate a tool which may be used in conjunction with the present invention to measure the depth or thickness of a disc's annulus.
Figure 55B:
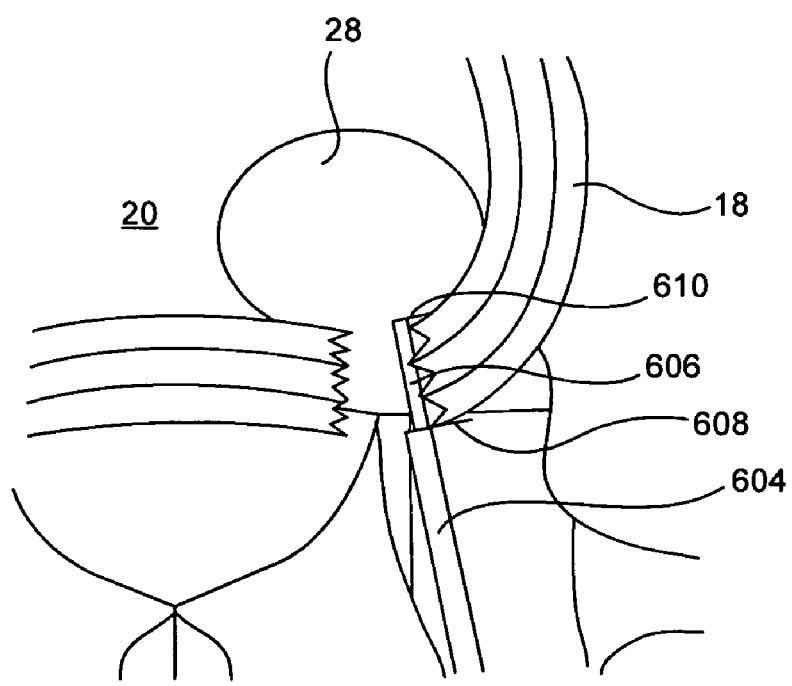

To this end, a measurement tool 602 of FIGS. 55A and 55B, having an outer shaft 604 and an inner shaft 606 slidably movable within outer shaft 604, is advanced to the disc defect 28 after surgical access is made. The distal end of each of the outer and inner shafts has a transversely extending foot 608, 610, respectively, which are preferably aligned parallel with each other. The inner shaft 606 is extended from the distal end of outer shaft 604 and through the defect opening within annulus 18 until far enough into the defect such that inner shaft foot 610 is able to be engaged against the inner wall of annulus 18. Outer shaft 604 is than distally advanced over inner shaft 606 until foot 608 engages against the outer wall of annulus 18. The distance between the feet indicates the thickness of annulus 18. Inner shaft 606 may have measurement markings on its outer surface to facilitate such measurement.

Figure 56A:
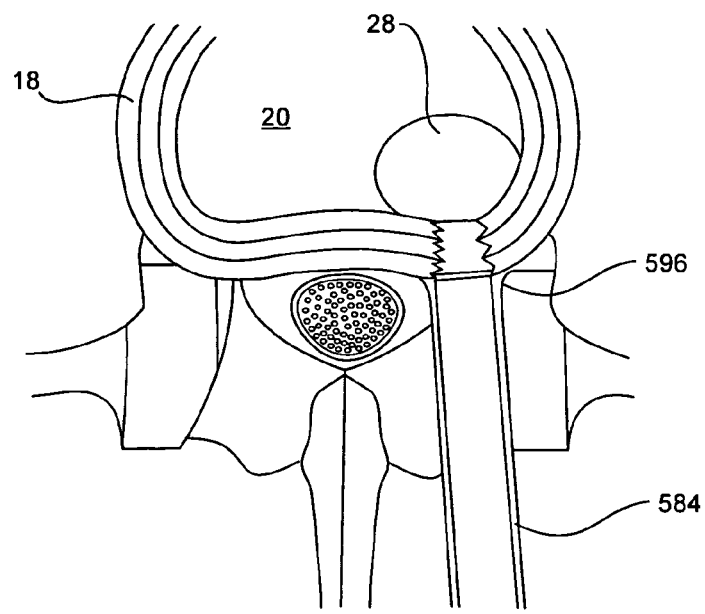
FIGS. 56A-56E illustrate a method of implanting the disc augmentation device of FIGS. 53A and 53B using the delivery tool of FIGS. 54A-54D.
Figure 56B:
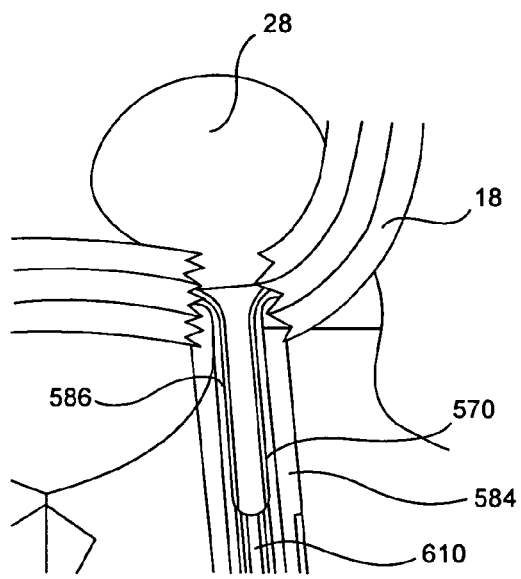
Figure 56C:
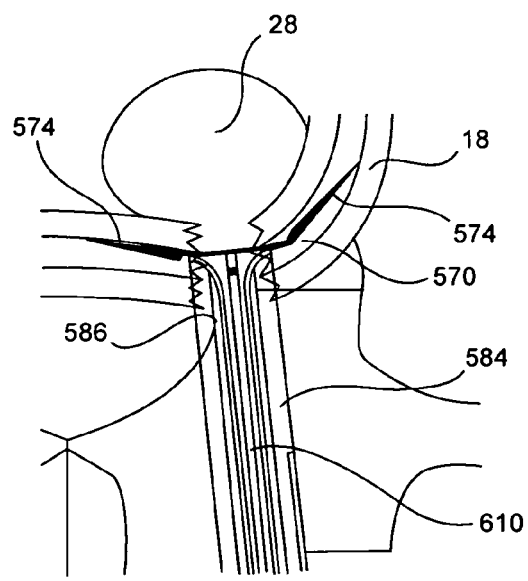
Figure 56D:
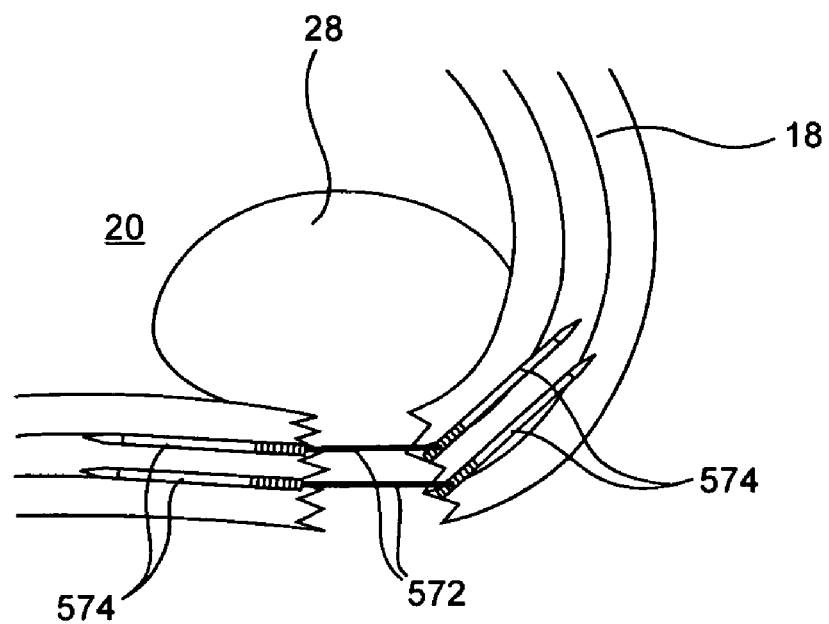
Figure 56E:
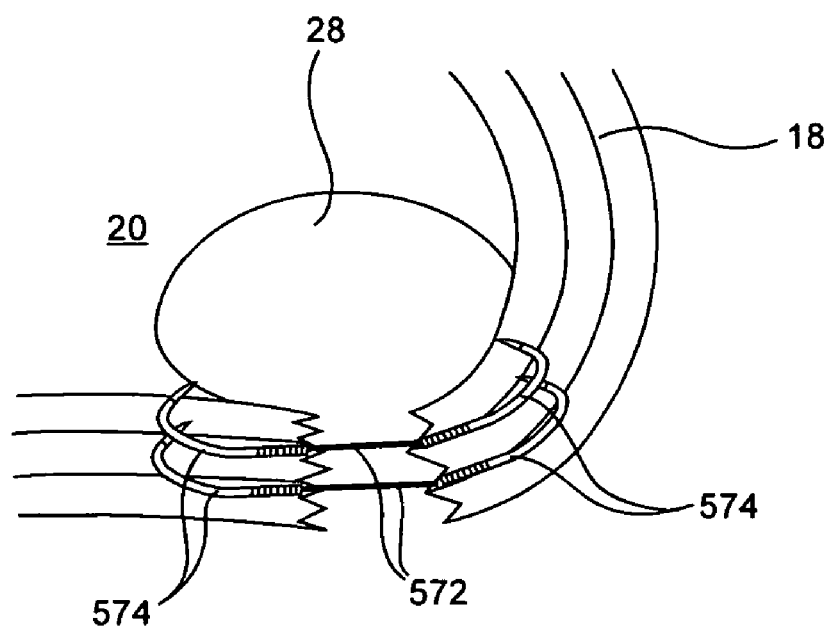

Referring now to FIGS. 56A-56D, various acts or steps for implanting an augmentation device 570 using tool 580 are illustrated. As illustrated in FIG. 56A, the distal end of outer shaft 584 is positioned within or at the outer aspect of disc void 28. Then, as illustrated in FIG. 56B, the distal end of inner shaft or cartridge 586 is extended distally to within the void until reaching a location where the innermost augmentation device (if more than one) is to be implanted. A rod 610 positioned within the lumen of inner shaft 586 is then advanced distally, such as by actuation of handle mechanism 590, to engage at least the most distally positioned augmentation device 570 within cartridge 586. The distal end of rod 610 may be curved or U-shaped to match that of the folded central portion of implant 570. Augmentation device 570 is then advanced into the annulus void to the level (i.e., intra-lamellar layer) at which the augmentation device is to be implanted, as illustrated in FIG. 56C, whereby its end portions 574 are guided by the internal rails to project radially outward and substantially transverse to the direction of advancement through cartridge 586 upon exiting from the distal end of the cartridge, as illustrated in FIG. 56C. Upon completely clearing the distal end of cartridge 586, device 570 is allowed to unfold and expand to its deployed configuration, as illustrated in FIG. 56D. With augmentation devices made of shape memory materials having a composition which is subject to achieving their preshaped condition upon exposure to body temperature, each device will individually and independently achieve its preshaped configuration upon reaching the selected temperature, as illustrated in FIG. 56E.

Alternatively, with augmentation devices having a composition which transforms to a preshaped condition at temperatures higher than body temperature, heat energy may then be applied to the device either with tool 580 or with another heating instrument. The above process is repeated as necessary for the selected number of augmentation devices 570 to be implanted, with each successive augmentation device inserted in an inter-lamellar layer that is more proximal (towards the outer circumference of the annulus) than the one before. Where the augmentation devices require other than body temperature to achieve their preshaped configuration, heat energy may be applied to all of the devices simultaneously subsequent to implantation of the last device.

FIGS. 57A-57E illustrate another tool 620 of the present invention for delivering and implanting certain of the augmentation devices of the present invention. Where only a single augmentation device, e.g., device 560 of FIG. 53A, is to be implanted within an annulus defect, tool 620 may be particularly useful. Tool 620 includes an outer sheath or tube 622 and an inner core or rod 624 which is translatable through outer sheath 622. The tube and core have cross-sectional dimensions such that they are deliverable through a defect within a disc annulus to be treated and such that a spacing or gap 632 exists between the two where the gap is dimensioned to the thickness of augmentation device 560. A diametric slit 626 is provided in the distal portion of the walls of outer sheath 622 and a diametric slit 630 is provided in the distal portion of inner core 634.

Figure 57C:
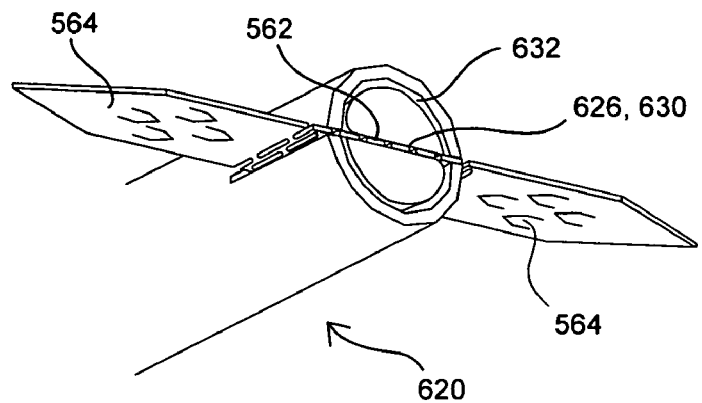
Figure 57D:
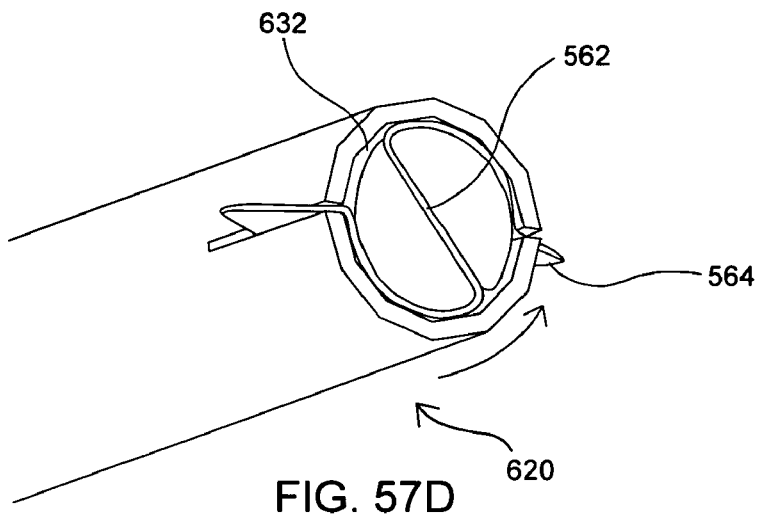
Figure 57E:
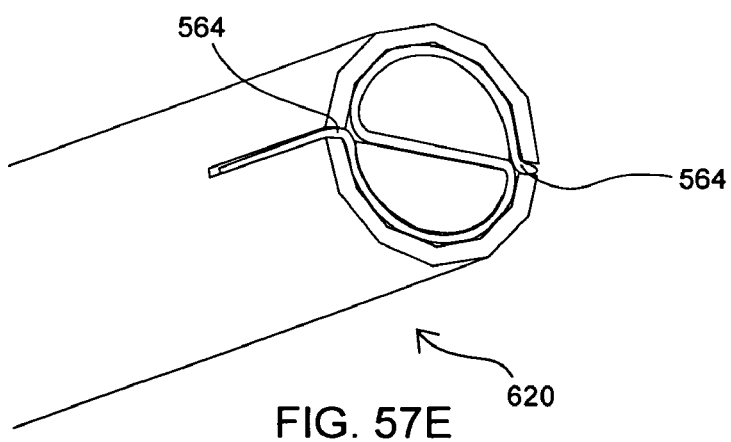

When slits 626 and 630 are longitudinally and radially aligned, as shown in FIG. 57B, they are positioned to receive a central portion 562 of augmentation device 560 such that length of device 560 is positioned transversely to that of device 620, as illustrated in FIG. 57C. Rotation of either outer tube 622 or inner core 624 relative to the other causes end portions 564 of device 560 to be folded into spacing 632 and around inner core 624, as illustrated in FIG. 57D. The rotation is continued until the distal ends of the distal ends of end portions 564 are positioned within wall slits 626 of outer tube 622, as illustrated in FIG. 57E. The distal end of tool 620 with preloaded augmentation device 560 is then inserted into the annulus defect to the level at which device 580 is to be deployed. Tool 620 is then reversely rotated such that end portions 564 are fully radially extended from tool 620 and device 560 is in a fully deployed or straightened condition. Tool 620 is then removed from the annulus, leaving implanted device 560 behind within the vertebral disc.

Figure 58:
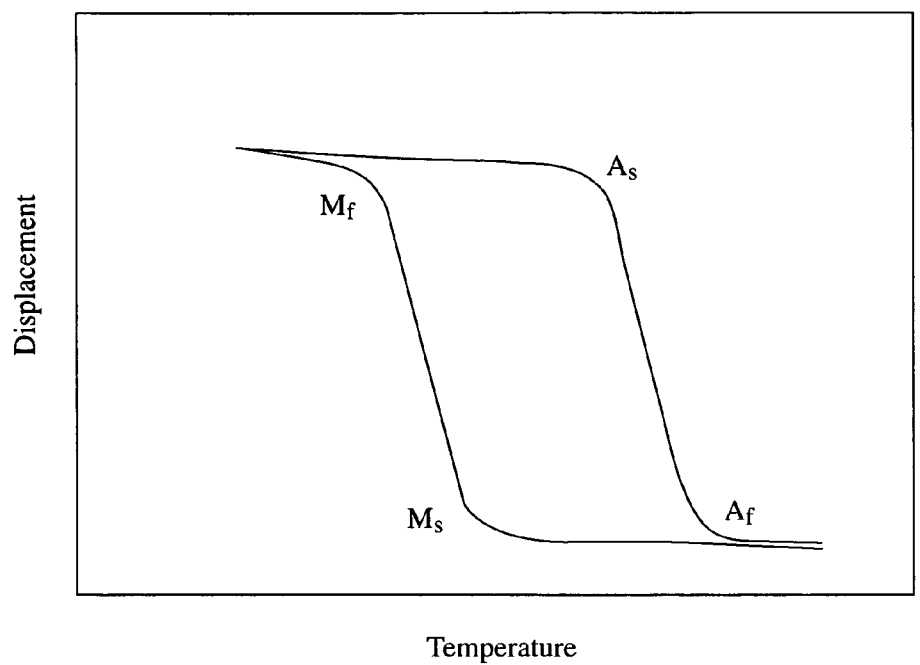
FIG. 58 is a hysteresis loop of shape memory alloys.

As mentioned above, certain of the implantable devices and components or portions thereof (e.g., anchors, tabs, pins, etc.), are made from one or more materials of the shape-memory alloy family. A shape memory alloy (SMA) (also known as memory metal or smart wire) is a metal having an original or initial geometry which is deformable into a second geometry, and is then able to regain its original geometry by heating (one-way effect) or, at higher ambient temperatures, simply during unloading (pseudo-elasticity). These properties are due to a temperature-dependent phase transformation from a low-symmetry to a highly symmetric crystallographic structure known as martensite and austenite, respectively. The two main types of SMA are the copper-zinc-aluminium alloys, and nickel-titanium (NiTi) alloys. NiTi alloys possess superior mechanical properties when compared to copper-based SMAs. While the temperatures at which the SMA changes its crystallographic structure are characteristic of the alloy, and can be tuned by varying the elemental ratios, the typical hysteresis curve or loop of SMAs is illustrated in the graph of FIG. 58. Ms denotes the temperature at which the SMA structure starts to change from austenite to martensite upon cooling; Mf is the temperature at which this transition is finished. Accordingly, As and Af are the temperatures at which the reverse transformation from martensite to austenite start and finish, respectively.

A subset of the SMA materials, namely superelastic alloys, may also be suitable for fabricating the subject devices or components thereof. When mechanically loaded, a superelastic alloy deforms reversibly to very high strains—up to 10%—by the creation of a stress-induced phase. When the load is removed, the new phase becomes unstable and the material regains its original shape. Unlike shape-memory alloys, no change in temperature is needed for the alloy to recover its initial shape.

As such, the augmentation devices of the present invention may be made of more than one shape memory alloy composition to effect the desired delivery and implant configurations. For example, the central portion of an augmentation device may be of a super elastic material and the end portions made of a temperature-sensitive shape memory material. As such, the central portion is bendable to a reduced profile for minimally invasive delivery, but not subject to shape changes upon exposure to heightened temperatures; while the end portions (which may not require or undergo any stress-related shape changes) or portions thereof, e.g., their distal ends and/or anchor tabs, are subject to changing configurations upon exposure to heat, e.g., body temperature or RF energy.

It should be noted that any of the above-described acts, steps or procedures, including but not limited to cannulation of the target area, removal of the affected portion of the disc, implantation of the subject implants within the target implant site, adjustment or readjustment of the implant, denervation or shrinkage of disc tissue, delivery of the prosthetic implant material and curing of the same may be facilitated by way of a scope delivered through a lumen of the delivery catheter and/or by way of various visualization techniques including but not limited to real time fluoroscopy, CT scanning or MR imaging, or a combination of preoperative CT or MR images superimposed onto a real time image tracking device, which are well known in the surgical arts.

Further, it is understood that the subject methods may all comprise the act of providing a suitable device. Such provision may be performed by the end user. In other words, the "providing" (e.g., a disc augmentation device) merely requires the end user obtain, access, approach, position, set-up, activate, power-up or otherwise act to provide the requisite device in the subject method. Methods recited herein may be carried out in any order of the recited events which is logically possible, as well as in the recited order of events.

The subject devices and systems may be provided in the form of a kit which includes at least one augmentation device of the present invention. A plurality of such devices may be provided where the devices have the same or varying sizes and shapes and are made of the same or varying materials. The kits may further include instruments and tools for implanting the subject devices, including but not limited to those described above as well as cannulas, trocars, scopes, sheaths, etc. Instructions for implanting the subject systems and devices and for using the above-described instrumentation may also be provided with the kits.

It must be noted that as used herein and in the appended claims, the singular forms "a", "an", and "the" include plural referents unless the context clearly dictates otherwise. Thus, for example, reference to "a device" may include a plurality of such devices and reference to "the prosthetic material" includes reference to one or more prosthetic materials and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An implantable intervertebral disc augmentation device wherein the intervertebral disc has a nucleus and an annulus, the device comprising:
    at least one planar structure sized for implantation within the annulus, the planar structure having a central portion and opposing end portions, the central portion having a fenestrated configuration and the end portions configured to secure the planar structure between two adjacent lamellae upon implantation therein, wherein at least one end portion includes an anchor formed as a cut out of the end portion and wherein the anchor and cut out are wholly enclosed by a solid section of the planar structure, the anchor adapted to extend outwardly into one of the lamellae subsequent to implantation to secure the planar structure between the two lamellae.

2. The intervertebral disc augmentation device of claim 1 comprising a plurality of said planar structures within a single structure.

3. The intervertebral disc augmentation device of claim 1, wherein at least a portion of the at least one planar structure comprises a shape memory material.

4. The intervertebral disc augmentation device of claim 3, wherein the central portion is made of a shape memory material.

5. The intervertebral disc augmentation device of claim 4, wherein the shape memory material is a super elastic material.

6. The intervertebral disc augmentation device of claim 3, wherein the end portions are made of a shape memory material.

7. The intervertebral disc augmentation device of claim 6, wherein the shape memory material is temperature responsive.

8. The intervertebral disc augmentation device of claim 7, wherein the shape memory material is responsive to body temperature.

9. The intervertebral disc augmentation device of claim 7, wherein the shape memory material is responsive to temperature greater than body temperature.

10. The intervertebral disc augmentation device of claim 7, wherein the device conducts heat energy from a source external to the body.

11. The intervertebral disc augmentation device of claim 10, wherein the heat energy is RF energy.

12. The intervertebral disc implant of claim 1, wherein the at least one planar structure has an undeployed configuration and a deployed configuration.

13. The intervertebral disc implant of claim 1, wherein the anchor is self-deployed upon implantation.

14. The intervertebral disc implant of claim 1, wherein the anchor is actively deployed upon implantation.

15. The implantable intervertebral disc augmentation device of claim 1, wherein the anchor is adapted to be deployed from a first position wherein the anchor extends substantially parallel to the at least one planar surface prior to implantation to a second position wherein the anchor extends outwardly from the at least one planar structure subsequent to implantation.

16. The implantable intervertebral disc augmentation device of claim 1, wherein the anchor is adapted to extend outwardly from the at least one planar structure before and after implantation.

17. The implantable intervertebral disc augmentation device of claim 1, wherein the anchor is an integral part of the at least one planar structure so as to form a hinge to enable the anchor to extend outwardly from the planar structure in a flared condition subsequent to implantation.

18. The implantable intervertebral disc augmentation device of claim 1, wherein the at least one end portion and anchor are made of a single construction.

19. A system for treating an intervertebral disc having a nucleus and an annulus, the system comprising:

an implantable intervertebral disc augmentation device, the device comprising at least one planar structure sized for implantation within the annulus, the planar structure having a central portion and opposing end portions, the central portion having a fenestrated configuration and the end portions configured to secure the planar structure between two adjacent lamellae upon implantation therein, wherein at least one end portion includes an anchor formed as a cut out of the end portion and wherein the anchor and cut out are wholly enclosed by a solid section of the planar structure, the anchor adapted to extend outwardly into one of the lamellae subsequent to implantation to secure the planar structure between the two lamellae; and a material configured for delivery into the nucleus, wherein the fenestrated central portion of the at least one planar structure of the device is configured to retain the material within the nucleus upon implantation within the annulus.

20. The system of claim 19, wherein the nuclear material comprises polyurethane.

21. The system of claim 19, wherein the nuclear material is in the form of a cord.

22. The system of claim 21, wherein the cord is truncatable to a selected length, wherein a volume of the truncated cord is sufficient to fill a void within the nucleus.

23. A method of treating an implantable intervertebral disc augmentation device wherein the intervertebral disc has a nucleus and an annulus, the device comprising at least one planar structure sized for implantation within the annulus, the planar structure having a central portion and opposing end portions, the central portion having a fenestrated configuration and the end portions configured to secure the planar structure between two adjacent lamellae upon implantation therein, wherein at least one end portion includes an anchor formed as a cut out of the end portion and wherein the anchor and cut out are wholly enclosed by a solid section of the planar structure, the anchor adapted to extend outwardly into one of the lamellae subsequent to implantation to secure the planar structure between the two lamellae, the method comprising:

delivering a material into the nucleus through a void in the annulus; and implanting the at least one planar structure within the annulus.

24. The method of claim 23, wherein the material is in the form of a cord and the act of delivering material into the nucleus comprises placing a length of the cord within the nucleus.

25. The method of claim 24 further comprising cutting a selected length of cord sufficient to fill a void within the nucleus.

26. The method of claim 23, wherein the act of implanting the at least one planar structure within the annulus comprises positioning the at least one structure between two adjacent lamellae of the annulus.

27. The method of claim 23, further comprising causing the end portions of the at least one planar structure to change configurations so as to anchor into the annulus.

28. The method of claim 27, wherein the act of causing the end portions to change configurations comprises exposing the end portions to heat.

29. The method of claim 28, wherein the heat is body temperature.

30. The method of claim 28, wherein the heat is greater than body temperature.

31. The method of claim 23, wherein the act of implanting the at least one planar structure comprises:
   providing the at least one planar structure preloaded within a tool having a proximal end and a distal end; inserting the distal end of the tool within the annulus; and
   ejecting the at least one planar structure from the distal end of the tool.

32. The method of claim 23, wherein implanting the at least one planar structure comprises delivering the at least one planar structure in a low profile condition and expanding the at least one planar structure along a length dimension.

33. The method of claim 23, further comprising measuring a thickness of the annulus.

34. An implantable intervertebral disc augmentation device wherein the intervertebral disc has a nucleus and an annulus, the device comprising:
   a planar structure sized for implantation within the annulus, the planar structure having a central portion and opposing end portions, the central portion having a fenestrated configuration and the end portions configured to secure the planar structure between two adjacent lamellae upon implantation therein, wherein the opposing end portions each have an anchor that is formed as a cut out of the end portion and wherein each anchor and cut out are wholly enclosed by a solid section of the planar structure, each anchor being adapted to extend outwardly from the planar structure in a flared condition and into one of the lamellae subsequent to implantation to secure the planar structure between the two lamellae.

35. An implantable intervertebral disc augmentation device wherein the intervertebral disc has a nucleus and an annulus, the device comprising:
   a plurality of planar structures, each planar structure of the plurality of planar structures sized for implantation within the annulus and each having a central portion with a fenestrated configuration and opposing end portions configured to secure the planar structure within the annulus upon implantation therein,
   wherein at least one end portion of a planar structure of the plurality of planar structures includes an anchor that is formed as a cut out of the planar structure and wherein the anchor and cut out are wholly enclosed by a solid section of the planar structure, the anchor adapted to extend outwardly into one of the lamellae subsequent to implantation to secure the planar structure between the two lamellae; and
   a bracket positioned about the central portions of the plurality of planar structures to hold and maintain the plurality of planar structures in place.

36. The implantable intervertebral disc augmentation device of claim 35 wherein the bracket is positioned about the central portions of the plurality of structures to hold and maintain the plurality of planar structures in substantially parallel, spaced relationship.

* * * * *